US008916691B2

(12) United States Patent
Boden et al.

(10) Patent No.: US 8,916,691 B2
(45) Date of Patent: Dec. 23, 2014

(54) METHODS OF EXPRESSING LIM MINERALIZATION PROTEIN

(75) Inventors: Scott D. Boden, Atlanta, GA (US); Sreedhara Sangadala, Dallas, GA (US); F. Louisa Titus, Atlanta, GA (US); William F. McKay, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1779 days.

(21) Appl. No.: 11/545,349

(22) Filed: Oct. 10, 2006

(65) Prior Publication Data

US 2007/0099176 A1 May 3, 2007

Related U.S. Application Data

(63) Continuation-in-part of application No. 10/292,951, filed on Nov. 13, 2002.

(60) Provisional application No. 60/331,321, filed on Nov. 14, 2001.

(51) Int. Cl.

| | |
|---|---|
| ***C07K 1/36*** | (2006.01) |
| ***C07K 1/22*** | (2006.01) |
| ***C07K 14/435*** | (2006.01) |
| ***C07K 16/18*** | (2006.01) |
| ***C07K 14/78*** | (2006.01) |
| ***A61L 27/38*** | (2006.01) |
| ***C07K 14/47*** | (2006.01) |
| *A61K 48/00* | (2006.01) |
| *A61K 35/12* | (2006.01) |
| *A61K 35/00* | (2006.01) |

(52) U.S. Cl.

CPC ............. *A61L 27/3856* (2013.01); *C07K 16/18* (2013.01); *C07K 14/78* (2013.01); *A61K 2121/00* (2013.01); *A61K 48/00* (2013.01); *A61K 35/12* (2013.01); *C07K 14/47* (2013.01); *A61K 35/13* (2013.01); *C12N 2799/022* (2013.01)

USPC ........................... 530/413; 435/69.1; 530/412

(58) Field of Classification Search

USPC ................................. 435/69.1; 530/412, 413

See application file for complete search history.

(56) References Cited

U.S. PATENT DOCUMENTS

| | | | |
|---|---|---|---|
| 4,800,159 | A | 1/1989 | Mullis et al. |
| 5,504,192 | A | 4/1996 | Gill et al. |
| 5,580,775 | A | 12/1996 | Fremeau, Jr. et al. |
| 6,300,127 | B1 | 10/2001 | Hair et al. |
| 7,045,614 | B1 | 5/2006 | Boden et al. |
| 2003/0180266 | A1 | 9/2003 | McKay et al. |

FOREIGN PATENT DOCUMENTS

| | | | |
|---|---|---|---|
| WO | 2000/066178 | * 11/2000 | ............. A61K 48/00 |
| WO | 2003042358 A | 5/2003 | |
| WO | 2008064094 A | 5/2008 | |

OTHER PUBLICATIONS

Apweiler et al, Biochim. et Biophys. Acta 1473(1):4-8, 1999.*

Jamry et al, Int. J. Biochem. Cell Biol. 27(4):415-423, 1995.*

Boden et al, Endocrinology 139(12):5125-5134, 1998.*

Hainfeld et al, J. Structural Biology 127:185-198, 1999.*

Brown, "Hybridization Analysis of DNA Blots" in Current Protocols in Molecular Biology John Wiley & Sons, Inc., 2003.*

Minamide et al, J. Bone Joint Surg. Am. 85-A(6):1030-1039, 2003.*

Amersham, Gel Filtration Principles and Methods, 2002; excerpted pages only, 13 pages total.*

Invitrogen, Ni-NTA Purification System User Manual, Version C, Aug. 7, 2006.*

Declerck et al, J. Biol. Chem. 263(30):15454-15461, 1988.*

Kotaro et al., "Adenovirus-mediated gene transfer to nucleus pulposus cells: implications for the treatment of inververtebral disc degeneration [Basic Science]", Spine, Nov. 1998, pp. 2437-2442, vol. 23.

Nanes et al., "Interferon-gamma inhibits 1,25-dihydroxyvitamin D3-stimulated synthesis of bone GLA protein in rat osteosarcoma cells by a pretranslational mechanism", Endocrinology, 1990, pp. 588-594, vol. 127, No. 2.

Alden et al, "Bone morphogenetic protein gene therapy for the induction of spinal arthrodesis", AANS Scientific Journals, Nerosurg Focus 4 (2): Article3 12, 1998

Boden et al., "Glucocorticoid-induced differentiation of fetal rat calvarial osteoblasts is mediated by bone morphogenetic protein-6", Endocrinology, 1997, pp. 2820-2828, vol. 138, No. 7.

Boden et al., "Differential effects and glucocorticoid potentiation of bone morphogenetic protein action during rat osteoblast differentiation in vitro", Endocrinology, 1996, pp. 3401-3407, vol. 137, No. 8.

* cited by examiner

*Primary Examiner* — Kevin Hill

(74) *Attorney, Agent, or Firm* — Sorell, Lenna & Schmidt, LLP

(57) ABSTRACT

Methods of expressing LIM mineralization protein in mammalian cells are described. Methods of expressing LIM mineralization protein and assessing glycosylation of the LIM mineralization protein in prokaryotic and non-mammalian eukaryotic cells are also described. The methods involve transfecting the cells with an isolated nucleic acid comprising a nucleotide sequence encoding a LIM mineralization protein. Transfection may be accomplished in vitro, ex vivo or in vivo by direct injection of virus or naked DNA, or by a nonviral vector such as a plasmid.

26 Claims, 11 Drawing Sheets

METHODS OF EXPRESSING LIM MINERALIZATION PROTEIN

CROSS-REFERENCE TO RELATED APPLICATIONS

This application is a continuation-in-part and also claims priority from U.S. application Ser. No. 10/292,951 filed Nov. 13, 2002 which claims priority to the Provisional Application Ser. No. 60/331,321 filed Nov. 14, 2001. The entirety of that provisional application is incorporated herein by reference. This application is related to U.S. patent application Ser. No. 09/124,238, filed Jul. 29, 1998, now U.S. Pat. No. 6,300,127, and U.S. patent application Ser. No. 09/959,578, filed Apr. 28, 2000, pending. Each of these applications is incorporated by reference herein in its entirety.

FIELD OF THE INVENTION

The field of the invention relates generally to methods for expressing LIM mineralization proteins in non-osseous cells such as intervertebral disc cells or cells of the nucleus pulposus. More specifically, the field of the invention relates to transfecting non-osseous cells such as intervertebral disc cells with a nucleic acid encoding a LIM mineralization protein.

BACKGROUND OF THE INVENTION

Osteoblasts are thought to differentiate from pluripotent mesenchymal stem cells. The maturation of an osteoblast results in the secretion of an extracellular matrix which can mineralize and form bone. The regulation of this complex process is not well understood but is thought to involve a group of signaling glycoproteins known as bone morphogenetic proteins (BMPs). These proteins have been shown to be involved with embryonic dorsal-ventral patterning, limb bud development, and fracture repair in adult animals. B. L. Hogan, Genes & Develop., 10, 1580 (1996). This group of transforming growth factor-beta superfamily secreted proteins has a spectrum of activities in a variety of cell types at different stages of differentiation; differences in physiological activity between these closely related molecules have not been clarified. D. M. Kingsley, Trends Genet., 10, 16 (1994).

To better discern the unique physiological role of different BMP signaling proteins, we recently compared the potency of BMP-6 with that of BMP-2 and BMP-4, for inducing rat calvarial osteoblast differentiation. Boden, et al., Endocrinology, 137, 3401 (1996). We studied this process in first passage (secondary) cultures of fetal rat calvaria that require BMP or glucocorticoid for initiation of differentiation. In this model of membranous bone formation, glucocorticoid (GC) or a BMP will initiate differentiation to mineralized bone nodules capable of secreting osteocalcin, the osteoblast-specific protein. This secondary culture system is distinct from primary rat osteoblast cultures which undergo spontaneous differentiation. In this secondary system, glucocorticoid resulted in a ten-fold induction of BMP-6 mRNA and protein expression which was responsible for the enhancement of osteoblast differentiation. Boden, et al., Endocrinology, 138, 2920 (1997).

In addition to extracellular signals, such as the BMPs, intracellular signals or regulatory molecules may also play a role in the cascade of events leading to formation of new bone. One broad class of intracellular regulatory molecules are the LIM proteins, which are so named because they possess a characteristic structural motif known as the LIM domain. The LIM domain is a cysteine-rich structural motif composed of two special zinc fingers that are joined by a 2-amino acid spacer. Some proteins have only LIM domains, while others contain a variety of additional functional domains. LIM proteins form a diverse group, which includes transcription factors and cytoskeletal proteins. The primary role of LIM domains appears to be in mediating protein-protein interactions, through the formation of dimers with identical or different LIM domains, or by binding distinct proteins.

In LIM homeodomain proteins, that is, proteins having both LIM domains and a homeodomain sequence, the LIM domains function as negative regulatory elements. LIM homeodomain proteins are involved in the control of cell lineage determination and the regulation of differentiation, although LIM-only proteins may have similar roles. LIM-only proteins are also implicated in the control of cell proliferation since several genes encoding such proteins are associated with oncogenic chromosome translocations.

Humans and other mammalian species are prone to diseases or injuries that require the processes of bone repair and/or regeneration. For example, treatment of fractures would be improved by new treatment regimens that could stimulate the natural bone repair mechanisms, thereby reducing the time required for the fractured bone to heal. In another example, individuals afflicted with systemic bone disorders, such as osteoporosis, would benefit from treatment regimens that would result in systemic formation of new bone. Such treatment regimens would reduce the incidence of fractures arising from the loss of bone mass that is a characteristic of this disease.

For at least these reasons, extracellular factors, such as the BMPs, have been investigated for the purpose of using them to stimulate formation of new bone in vivo. Despite the early successes achieved with BMPs and other extracellular signalling molecules, their use entails a number of disadvantages. For example, relatively large doses of purified BMPs are required to enhance the production of new bone, thereby increasing the expense of such treatment methods. Furthermore, extracellular proteins are susceptible to degradation following their introduction into a host animal. In addition, because they are typically immunogenic, the possibility of stimulating an immune response to the administered proteins is ever present.

Due to such concerns, it would be desirable to have available treatment regimens that use an intracellular signaling molecule to induce new bone formation. Advances in the field of gene therapy now make it possible to introduce into osteogenic precursor cells, that is, cells involved in bone formation, or peripheral blood leukocytes, nucleotide fragments encoding intracellular signals that form part of the bone formation process. Gene therapy for bone formation offers a number of potential advantages: (1) lower production costs; (2) greater efficacy, compared to extracellular treatment regiment, due to the ability to achieve prolonged expression of the intracellular signal; (3) it would by-pass the possibility that treatment with extracellular signals might be hampered due to the presence of limiting numbers of receptors for those signals; (4) it permits the delivery of transfected potential osteoprogenitor cells directly to the site where localized bone formation is required; and (5) it would permit systemic bone formation, thereby providing a treatment regimen for osteoporosis and other metabolic bone diseases.

In addition to diseases of the bone, humans and other mammalian species are also subject to intervertebral disc degeneration, which is associated with, among other things, low back pain, disc herniations, and spinal stenosis. Disc degeneration is associated with a progressive loss of proteoglycan matrix. This may cause the disc to be more susceptible to bio-mechanical injury and degeneration. Accordingly, it would be desirable to have a method of stimulating proteoglycan and/or collagen synthesis by the appropriate cells, such as, for example, cells of the nucleous pulposus, cells of the annulus fibrosus, and cells of the intervertebral disc.

SUMMARY OF THE INVENTION

According to a first aspect of the invention, a method of expressing a LIM mineralization protein in a non-osseous mammalian cell is provided. According to this aspect of the invention, the method comprises transfecting the cell with an isolated nucleic acid comprising a nucleotide sequence encoding the LIM mineralization protein operably linked to a promoter. The cell can be a cell capable of producing proteoglycan and/or collagen such that the expression of the LIM mineralization protein stimulates proteoglycan and/or collagen synthesis in the cell. The isolated nucleic acid according to this aspect of the invention can be a nucleic acid which can hybridize under standard conditions to a nucleic acid molecule complementary to the full length of SEQ. ID NO: 25; and/or a nucleic acid molecule which can hybridize under highly stringent conditions to a nucleic acid molecule complementary to the full length of SEQ. ID NO: 26. The cell can be a stem cell, an intervertebral disc cell, a cell of the annulus fibrosus, or a cell of the nucleus pulposus.

According to a second aspect of the invention, a non-osseous mammalian cell comprising an isolated nucleic acid sequence encoding a LIM mineralization protein is provided. According to this aspect of the invention, the cell can be a stem cell, a cell of the nucleus pulposus, a cell of the annulus fibrosus, or an intervertebral disc cell.

According to a third aspect of the invention, a method of treating intervertebral disc injury or disease is provided. According to this aspect of the invention, the method comprises transfecting an isolated nucleic acid into a mammalian cell capable of producing proteoglycan and/or collagen. The isolated nucleic acid comprises a nucleotide sequence encoding a LIM mineralization protein operably linked to a promoter. The LIM mineralization protein stimulates proteoglycan and/or collagen synthesis in the cell.

According to a fourth aspect of the invention, an intervertebral disc implant is provided. According to this aspect of the invention, the implant comprises a carrier material and a plurality of mammalian cells comprising an isolated nucleic acid sequence encoding a LIM mineralization protein. Also according to this aspect of the invention, the carrier material comprises a porous matrix of biocompatible material and the mammalian cells are incorporated into the carrier material.

According to a fifth aspect of the invention, a system and a method is developed to meet the demands of proteomics for transient transfection-based mammalian expression. According to this aspect of the invention, a method is developed for identifying LMP-1 protein by internal sequencing and assessing post-translational glycosylation in a mammalian expression system wherein the method employs carbohydrate analysis of LMP-1 hydrolysates.

Furthermore, this aspect of the invention introduces a novel purification and detection methods wherein the skilled artisan is now able to purify the recombinant proteins to a level of homogeneity by means of (1) size fractionation of proteins prior to metal affinity chromatography to improve efficiency of affinity resin and (2) identification of tryptic fragments of purified protein.

According to a sixth aspect of the invention, a composition is prepared that comprises a LIM mineralization protein that is substantially free of any carbohydrate moiety.

BRIEF DESCRIPTION OF THE DRAWINGS

The present invention may be better understood with reference to the accompanying drawings in which:

In FIG. 4A, exogenous LMP-1 expression was induced with different doses (MOI) of the Ad-hLMP-1 virus and quantitated with realtime PCR. The data is normalized to HLMP-1 mRNA levels from Ad-LMP-1 MOI 5 for comparison purposes. No HLMP-1 was detected in negative control groups, the no-treatment ("NT") or Ad-LacZ treatment ("LacZ"). HLMP-1 mRNA levels in a dose dependent fashion to reach a plateau of approximately 8 fold with a MOI of 25 and 50.

In FIG. 4B, each result is expressed as mean with SD for three samples.

In FIG. 5, "**" indicates data points for which the P value is $<0.01$ versus the untreated control.

In FIGS. 6A and 6B, each data point is expressed as mean with SD for six samples. In FIGS. 6A and 6B, "**" indicates data points for which the P value is $P<0.01$.

In FIG. 8, "**" indicates data points for which the P value is <0.01 for infection with AdLMP-1 versus an untreated control.

FIG. 10 illustrates the effect of noggin (a BMP antagonist) on LMP-1 mediated increase in sGAG production. As seen in FIG. 10, infection of rat annulus cells with Ad-LMP-1 at a MOI of 25 led to a three fold increase in sGAG produced between day 3 and day 6. This increase was blocked by the addition of noggin (a BMP antagonist) at concentration of 3200 ng/ml and 800 ng/m. As shown in FIG. 10, however, noggin did not significantly alter sGAG production in uninfected cells. As can also be seen in FIG. 10, stimulation with rhBMP-2 at 100 ng/ml led to a 3 fold increase in sGAG production between day 3 and day 6 after addition of BMP-2. Noggin at 800 ng/ml also blocked this increase.

As shown in FIG. 11, LMP-1 with the CMV promoter when delivered by the AAV vector is also effective in stimulating glycosaminoglycan synthesis by rat disc cells in monolayer.

DETAILED DESCRIPTION OF THE PREFERRED EMBODIMENTS

Figure 1:
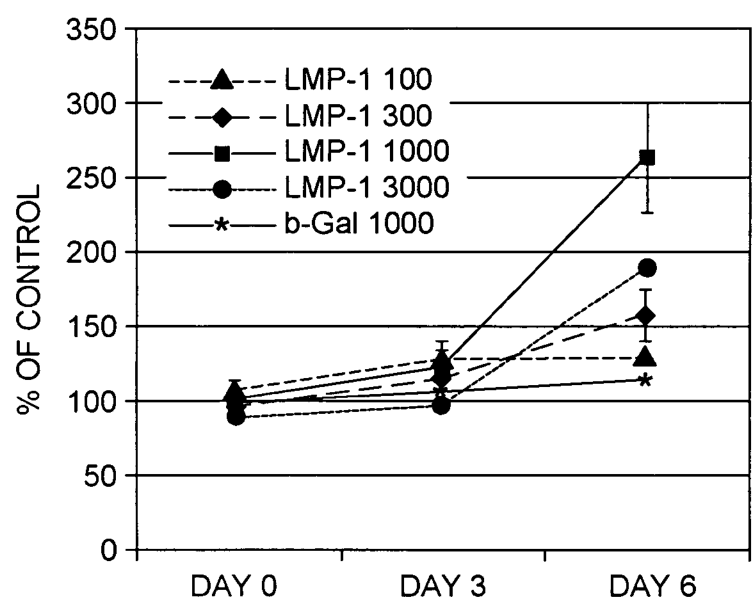
FIG. 1 is a graph showing the production of sulfated glycosaminoglycan (sGAG) after expression of HLMP-1 by rat intervertebral disc cells transfected with different MOIs.

The present invention relates to the transfection of non-osseous cells with nucleic acids encoding LIM mineralization proteins. The present inventors have discovered that transfection of non-osseous cells such as intervertebral disc cells with nucleic acids encoding LIM mineralization proteins can result in the increased synthesis of proteoglycan, collagen and other intervertebral disc components and tissue. The present invention also provides a method for treating intervertebral disc disease associated with the loss of proteoglycan, collagen, or other intervertebral disc components.

It is to be understood that both the foregoing general description and the following detailed description are exemplary and explanatory and are intended to provide further explanation of the invention as claimed.

ABBREVIATIONS AND DEFINITIONS

BMP, Bone Morphogenetic Protein; HLMP-1, Human LMP-1, also designated as Human LIM Protein or HLMP; HLMP-1s Human LMP-1 Short (truncated) protein, HLMPU Human LIM Protein Unique Region; LMP LIM mineralization protein, LMP-1, LIM mineralization protein-1; MEM Minimal essential medium; Trm, Triamcinolone; β-GlyP; beta-GlyP, Beta-glycerolphosphate; RACE, Rapid Amplification of cDNA Ends; RLMP, Rat LIM mineralization protein, also designated as RLMP-1; RLMPU, Rat LIM Protein Unique Region; RNAsin, RNase inhibitor; ROB, Rat Osteoblast; 10-4, Clone containing cDNA sequence for RLMP (SEQ ID NO: 2); UTR, Untranslated Region; HLMP-,2 Human LMP Splice Variant 2; HLMP-3, Human LMP Splice Variant 3; MOI, multiplicity of infection; sGAG, sulfated glycosaminoglycan; AdHLMP-1, Recombinant Type 5 Adenovirus comprising nucleotide sequence encoding HLMP-1; SDS-PAGE, Sodium dodecyl polyacrylamide gel electrophoresis; FPLC, Fast performance liquid chromatography; HPLC, High performance liquid chromatography; Ni-NTA, Nickel-nitrilotriacetic acid; PMSF, phenylmethylsulfonyl fluoride; BSA, bovine serum albumin. MALDI TOF, Matrix Assisted Laser Desorption Ionization Time of Flight; MS, Mass spectrometry; PSD, Post source decay; IPTG, Isopropyl-βD-thiogalactopyranoside; and LB, Luria Broth medium.

A LIM gene (10-4/RLMP) has been isolated from stimulated rat calvarial osteoblast cultures (SEQ. ID NO: 1, SEQ. ID NO: 2). See U.S. Pat. No. 6,300,127. This gene has been cloned, sequenced and assayed for its ability to enhance the efficacy of bone mineralization in vitro. The protein RLMP has been found to affect the mineralization of bone matrix as well as the differentiation of cells into the osteoblast lineage. Unlike other known cytokines (e.g., BMPs), RLMP is not a secreted protein, but is instead an intracellular signaling molecule. This feature has the advantage of providing intracellular signaling amplification as well as easier assessment of transfected cells. It is also suitable for more efficient and specific in vivo applications. Suitable clinical applications include enhancement of bone repair in fractures, bone defects, bone grafting, and normal homeostasis in patients presenting with osteoporosis.

The amino acid sequence of a corresponding human protein, named human LMP-1 ("HLMPI"), has also been cloned, sequenced and deduced. See U.S. Pat. No. 6,300,127. The human protein has been found to demonstrate enhanced efficacy of bone mineralization in vitro and in vivo. The sequence of LMP-1 contains a highly conserved N-terminal PDZ domain and three C-terminal LIM domains. The sequence analysis of LMP-1 predicts two putative N-glycosylatione sites. At least in one aspect of this invention is to verify whether LMP-1 was expressed in detectable amounts and purify the recombinant LMP-1 for carbohydrate analysis to determine if the LMP-1 expressed in mammalian system undergoes post translational glycosylation.

Additionally, a truncated (short) version of HLMP-1, termed HLMP-1s, has been characterized. See U.S. Pat. No. 6,300,127. This short version resulted from a point mutation in one source of a cDNA clone, providing a stop codon which truncates the protein. HLMP-1s has been found to be fully functional when expressed in cell culture and in vivo.

Using PCR analysis of human heart cDNA library, two alternative splice variants (referred to as HLMP-2 and HLMP-3) have been identified that differ from HLMP-1 in a region between base pairs 325 and 444 in the nucleotide sequence encoding HLMP-1. See U.S. patent application Ser. No. 09/959,578, filed Apr. 28, 2000, pending. The HLMP-2 sequence has a 119 base pair deletion and an insertion of 17 base pairs in this region. Compared to HLMP-1, the nucleotide sequence encoding HLMP-3 has no deletions, but it does have the same 17 base pairs as HLMP-2, which are inserted at position 444 in the HLMP-1 sequence.

LMP is a pluripotent molecule, which regulates or influences a number of biological processes. The different splice variants of LMP are expected to have different biological functions in mammals. They may play a role in the growth, differentiation, and/or regeneration of various tissues. For example, some form of LMP is expressed not only in bone, but also in muscle, tendons, ligaments, spinal cord, peripheral nerves, and cartilage.

According to one aspect, the present invention relates to a method of stimulating proteoglycan and/or collagen synthesis in a mammalian cell by providing an isolated nucleic acid comprising a nucleotide sequence encoding LIM mineralization protein operably linked to a promoter; transfecting said isolated nucleic acid sequence into a mammalian cell capable of producing proteoglycan; and expressing said nucleotide sequence encoding LIM mineralization protein, whereby proteoglycan synthesis is stimulated. The mammalian cell may be a non-osseous cell, such as an intervertebral disc cell, a cell of the annulus fibrosus, or a cell of the nucleus pulposus. Transfection may occur either ex vivo or in vivo by direct injection of virus or naked DNA, such as, for example, a plasmid. In certain embodiments, the virus is a recombinant adenovirus, preferably AdHLMP-1.

Another embodiment of the invention comprises a non-osseous mammalian cell comprising an isolated nucleic acid sequence encoding a LIM mineralization protein. The non-osseous mammalian cell may be a stem cell (e.g., a pluripotential stem cell or a mesenchymal stem cell) or an intervertebral disc cell, preferably a cell of the nucleus pulposus or a cell of the annulus fibrosus.

In a different aspect, the invention is directed to a method of expressing an isolated nucleotide sequence encoding LIM mineralization protein in a non-osseous mammalian cell, the method comprising: providing an isolated nucleic acid comprising a nucleotide sequence encoding LIM mineralization protein operably linked to a promoter; transfecting said isolated nucleic acid sequence into a non-osseous mammalian cell; and expressing said nucleotide sequence encoding LIM mineralization protein. The non-osseous mammalian cell may be a stem cell or an intervertebral disc cell (e.g., a cell of the nucleus pulposus or annulus fibrosus). Transfection may occur either ex vivo or in vivo by direct injection of virus or naked DNA, such as, for example, a plasmid. The virus can be a recombinant adenovirus, preferably AdHLMP-1.

In yet another embodiment, the invention is directed to a method of treating intervertebral disc disease by reversing, retarding or slowing disc degeneration, the method comprising: providing an isolated nucleic acid comprising a nucleotide sequence encoding LIM mineralization protein operably linked to a promoter; transfecting said isolated nucleic acid sequence into a mammalian cell capable of producing proteoglycan; and stimulating proteoglycan synthesis in said cell by expressing said nucleotide sequence encoding LIM mineralization protein, whereby disc degeneration is reversed, halted or slowed. The disc disease may involve lower back pain, disc herniation, or spinal stenosis. The mammalian cell may be a non-osseous cell, such as a stem cell or an intervertebral disc cell (e.g., a cell of the annulus fibrosus, or a cell of the nucleus pulposus).

Transfection may occur either ex vivo or in vivo by direct injection of virus or naked DNA, such as, for example, a plasmid. In certain embodiments, the virus is a recombinant adenovirus, preferably AdHLMP-1.

The present invention relates to novel mammalian LIM proteins, herein designated LIM mineralization proteins, or LMPs. The invention relates more particularly to human LMP, known as HLMP or HLMP-1, or alternative splice variants of human LMP, which are known as HLMP-2 or HLMP-3. The Applicants have discovered that these proteins enhance bone mineralization in mammalian cells grown in vitro. When produced in mammals, LMP also induces bone formation in vivo.

Ex vivo transfection of bone marrow cells, osteogenic precursor cells, peripheral blood cells, and stem cells (e.g., pluripotential stem cells or mesenchymal stem cells) with nucleic acid that encodes a LIM mineralization protein (e.g., LMP or HLMP), followed by reimplantation of the transfected cells in the donor, is suitable for treating a variety of bone-related disorders or injuries. For example, one can use this method to: augment long bone fracture repair; generate bone in segmental defects; provide a bone graft substitute for fractures; facilitate tumor reconstruction or spine fusion; and provide a local treatment (by injection) for weak or osteoporotic bone, such as in osteoporosis of the hip, vertebrae, or wrist. Transfection with LMP or HLMP-encoding nucleic acid is also useful in: the percutaneous injection of transfected marrow cells to accelerate the repair of fractured long bones; treatment of delayed union or non-unions of long bone fractures or pseudoarthrosis of spine fusions; and for inducing new bone formation in avascular necrosis of the hip or knee.

In addition to ex vivo methods of gene therapy, transfection of a recombinant DNA vector comprising a nucleic acid sequence that encodes LMP or HLMP can be accomplished in vivo. When a DNA fragment that encodes LMP or HLMP is inserted into an appropriate viral vector, for example, an adenovirus vector, the viral construct can be injected directly into a body site where endochondral bone formation is desired. By using a direct, percutaneous injection to introduce the LMP or HLMP sequence, stimulation of bone formation can be accomplished without the need for surgical intervention either to obtain bone marrow cells (to transfect ex vivo) or to reimplant them into the patient at the site where new bone is required. Alden, et al., Neurosurgical Focus (1998), have demonstrated the utility of a direct injection method of gene therapy using a cDNA that encodes BMP-2, which was cloned into an adenovirus vector.

It is also possible to carry out in vivo gene therapy by directly injecting into an appropriate body site, a naked, that is, unencapsulated, recombinant plasmid comprising a nucleic acid sequence that encodes HLMP. In this embodiment of the invention, transfection occurs when the naked plasmid DNA is taken up, or internalized, by the appropriate target cells, which have been described. As in the case of in vivo gene therapy using a viral construct, direct injection of naked plasmid DNA offers the advantage that little or no surgical intervention is required. Direct gene therapy, using naked plasmid DNA that encodes the endothelial cell mitogen VEGF (vascular endothelial growth factor), has been successfully demonstrated in human patients. Baumgartner, et al., Circulation, 97, 12, 1114-1123 (1998).

For intervertebral disc applications, ex vivo transfection may be accomplished by harvesting cells from an intervertebral disc, transfecting the cells with nucleic acid encoding LMP in vitro, followed by introduction of the cells into an intervertebral disc. The cells may be harvested from or introduced back into the intervertebral disc using any means known to those of skill in the art, such as, for example, any surgical techniques appropriate for use on the spine. In one embodiment, the cells are introduced into the intervertebral disc by injection.

Also according to the invention, stem cells (e.g., pluripotential stem cells or mesenchymal stem cells) can be transfected with nucleic acid encoding a LIM Mineralization Protein ex vivo and introduced into the intervertebral disc (e.g., by injection).

The cells transfected ex vivo can also be combined with a carrier to form an intervertebral disc implant. The carrier comprising the transfected cells can then be implanted into the intervertebral disc of a subject. Suitable carrier materials are disclosed in Helm, et al., "Bone Graft Substitutes for the Promotion of Spinal Arthrodesis", Neurosurg Focus, Vol. 10 (4): April 2001. The carrier preferably comprises a biocompatible porous matrix such as a demineralized bone matrix (DBM), a biocompatible synthetic polymer matrix or a protein matrix. Suitable proteins include extracellular matrix proteins such as collagen. The cells transfected with the LMP ex vivo can be incorporated into the carrier (i.e., into the pores of the porous matrix) prior to implantation.

Similarly, for intervertebral disc applications where the cells are transfected in vivo, the DNA may be introduced into the intervertebral disc using any suitable method known to those of skill in the art. In one embodiment, the nucleic acid is directly injected into the intervertebral space.

By using an adenovirus vector to deliver LMP into osteogenic cells, transient expression of LMP is achieved. This occurs because adenovirus does not incorporate into the genome of target cells that are transfected. Transient expression of LMP, that is, expression that occurs during the lifetime of the transfected target cells, is sufficient to achieve the objects of the invention. Stable expression of LMP, however, can occur when a vector that incorporates into the genome of the target cell is used as a delivery vehicle. Nishida et al, the teaching of which is incorporated herewith in its entirety, investigated the efficacy of adenovirus-mediate gene transfer to Nucleus Pulposus cells. Nishida et al., "Adenovirus-Mediated Gene Transfer to Nucleus Pulposus Cells: Implication for the Treatment of Intervertebral Disc Degeneration", Spine, Vol. 23(22): 2437-2442 (15 Nov. 1998).

Nishida et al successfully demonstrated adenovirus-mediated gene transfer to the intervertebral disc with persistent expression of the marker gene for at least 12 weeks in vivo in high titters. In addition, the transfected intervertebral discs in Nishida's experiment did not exhibit typical signs of local immune activity. This result indicates that the avascular environment of intervertebral disc limits the access of immunocompetent cells, thereby preventing immune reactivity and prolonging gene expressions. Due to such results the inventors believe that Retrovirus-based vectors, are also suitable for this purpose.

Stable expression of LMP is particularly useful for treating various systemic bone-related disorders, such as osteoporosis and osteogenesis imperfecta. For this embodiment of the invention, in addition to using a vector that integrates into the genome of the target cell to deliver an LMP-encoding nucleotide sequence into target cells, LMP expression can be placed under the control of a regulatable promoter. For example, a promoter that is turned on by exposure to an exogenous inducing agent, such as tetracycline, is suitable.

Using this approach, one can stimulate formation of new bone on a systemic basis by administering an effective amount of the exogenous inducing agent. Once a sufficient quantity of bone mass is achieved, administration of the exogenous inducing agent can be discontinued. This process may be repeated as needed to replace bone mass lost, for example, as a consequence of osteoporosis. Antibodies specific for HLMP are particularly suitable for use in methods for assaying the osteoinductive, that is, bone-forming, potential of patient cells. In this way one can identify patients at risk for slow or poor healing of bone repair. Also, HLMP-specific antibodies are suitable for use in marker assays to identify risk factors in bone degenerative diseases, such as, for example, osteoporosis.

Following well known and conventional methods, the genes of the present invention are prepared by ligation of nucleic acid segments that encode LMP to other nucleic acid sequences, such as cloning and/or expression vectors. Methods needed to construct and analyze these recombinant vectors, for example, restriction endonuclease digests, cloning protocols, mutagenesis, organic synthesis of oligonucleotides and DNA sequencing, have been described. For DNA sequencing DNA, the dieoxyterminator method is the preferred.

Many treatises on recombinant DNA methods have been published, including Sambrook, et al., Molecular Cloning: A Laboratory Manual, $2^{nd}$ edition, Cold Spring Harbor Press, (1988), Davis. et al., Basic Methods in Molecular Biology, Elsevier (1986), and Ausubel, et al., Current Protocols in Molecular Biology, Wiley Interscience (1988). These reference manuals are specifically incorporated by reference herein.

Primer-directed amplification of DNA or cDNA is a common step in the expression of the genes of this invention. It is typically performed by the polymerase chain reaction (PCR). PCR is described in U.S. Pat. No. 4,800,159 to Mullis, et al. and other published sources. The basic principle of PCR is the exponential replication of a DNA sequence by successive cycles of primer extension. The extension products of one primer, when hybridized to another primer, becomes a template for the synthesis of another nucleic acid molecule. The primer-template complexes act as substrate for DNA polymerase, which in performing its replication function, extends the primers. The conventional enzyme for PCR applications is the thermostable DNA polymerase isolated from Thermus aquaticus, or Taq DNA polymerase.

Numerous variations of the basic PCR method exist, and a particular procedure of choice in any given step needed to construct the recombinant vectors of this invention is readily performed by a skilled artisan. For example, to measure cellular expression of 10-4/RLMP, RNA is extracted and reverse transcribed under standard and well known procedures. The resulting cDNA is then analyzed for the appropriate mRNA sequence by PCR.

The gene encoding the LIM mineralization protein is expressed in an expression vector in a recombinant expression system. Of course, the constructed sequence need not be the same as the original, or its complimentary sequence, but instead may be any sequence determined by the degeneracy of the DNA code that nonetheless expresses an LMP having bone forming activity. Conservative amino acid substitutions, or other modifications, such as the occurrence of an amino-terminal methionine residue, may also be employed.

A ribosome binding site active in the host expression system of choice is ligated to the 5' end of the chimeric LMP coding sequence, forming a synthetic gene. The synthetic gene can be inserted into any one of a large variety of vectors for expression by ligating to an appropriately linearized plasmid. A regulatable promoter, for example, the *E. coli* lac promoter, is also suitable for the expression of the chimeric coding sequences. Other suitable regulatable promoters include trp, tac, recA, T7 and lambda promoters.

DNA encoding LMP is transfected into recipient cells by one of several standard published procedures, for example, calcium phosphate precipitation, DEAE-Dextran, electroporation or protoplast fusion, to form stable transformants. Calcium phosphate precipitation is preferred, particularly when performed as follows.

DNAs are coprecipitated with calcium phosphate according to the method of Graham and Van Der, Virology, 52, 456 (1973), before transfer into cells. An aliquot of 40-50 μg of DNA, with salmon sperm or calf thymus DNA as a carrier, is used for $0.5\times10^6$ cells plated on a 100 mm dish. The DNA is mixed with 0.5 ml of 2× Hepes solution (280 mM NaCl, 50 mM Hepes and 1.5 mM $Na_2HPO_4$, pH 7.0), to which an equal volume of 2× $CaCl_2$ (250 mM $CaCl_2$ and 10 mM Hepes, pH 7.0) is added. A white granular precipitate, appearing after 30-40 minutes, is evenly distributed dropwise on the cells, which are allowed to incubate for 4-16 hours at 37° C. The medium is removed and the cells shocked with 15% glycerol in PBS for 3 minutes. After removing the glycerol, the cells are fed with Dulbecco's Minimal Essential Medium (DMEM) containing 10% fetal bovine serum.

DNA can also be transfected using: the DEAE-Dextran methods of Kimura, et al., Virology, 49:394 (1972) and Sompayrac et al., Proc. Natl. Acad. Sci. USA, 78, 7575 (1981); the electroporation method of Potter, Proc. Natl. Acad. Sci. USA, 81, 7161 (1984); and the protoplast fusion method of Sandri-Goddin et al., Molec. Cell. Biol., 1, 743 (1981).

Phosphoramidite chemistry in solid phase is the preferred method for the organic synthesis of oligodeoxynucleotides and polydeoxynucleotides. In addition, many other organic synthesis methods are available. Those methods are readily adapted by those skilled in the art to the particular sequences of the invention.

The present invention also includes nucleic acid molecules that hybridize under standard conditions to any of the nucleic acid sequences encoding the LIM mineralization proteins of the invention. "Standard hybridization conditions" will vary with the size of the probe, the background and the concentration of the nucleic acid reagents, as well as the type of hybridization, for example, in situ, Southern blot, or hybrization of DNA-RNA hybrids (Northern blot). The determination of "standard hybridization conditions" is within the level of skill in the art. For example, see U.S. Pat. No. 5,580,775 to Fremeau, et al., herein incorporated by reference for this purpose. See also, Southern, J. Mol. Biol., 98:503 (1975), Alwine, et al., Meth. Enzymol., 68:220 (1979), and Sambrook, et al., Molecular Cloning: A Laboratory Manual, $2^{nd}$ edition, Cold Spring Harbor Press, 7.19-7.50 (1989).

One preferred set of standard hybrization conditions involves a blot that is prehybridized at 42° C. for 2 hours in 50% formamide, 5×SSPE (150 nM NaCl, 10 mM Na $H_2PO_4$ [pH 7.4], 1 mM EDTA [pH 8.0]) 5× Denhardt's solution (20 mg Ficoll, 20 mg polyvinylpyrrolidone and 20 mg BSA per 100 ml water), 10% dextran sulphate, 1% SDS and 100 μg/ml salmon sperm DNA. A $p^{32}$-labeled cDNA probe is added, and hybridization is continued for 14 hours. Afterward, the blot is washed twice with 2×SSPE, 0.1% SDS for 20 minutes at 22° C., followed by a 1 hour wash at 65° C. in 0.1×SSPE, 0.1% SDS. The blot is then dried and exposed to x-ray film for 5 days in the presence of an intensifying screen.

Under "highly stringent conditions," a probe will hybridize to its target sequence if those two sequences are substantially identical. As in the case of standard hybridization conditions, one of skill in the art can, given the level of skill in the art and the nature of the particular experiment, determine the conditions under which only substantially identical sequences will hybridize.

According to one aspect of the present invention, an isolated nucleic acid molecule comprising a nucleic acid sequence encoding a LIM mineralization protein is provided. The nucleic acid molecule according to the invention can be a molecule which hybridizes under standard conditions to a nucleic acid molecule complementary to the full length of SEQ. ID NO: 25 and/or which hybridizes under highly stringent conditions to a nucleic acid molecule complementary to the full length of SEQ. ID NO: 26. More specifically, the isolated nucleic acid molecule according to the invention can encode HLMP-1, HLMP-1s, RLMP, HLMP-2, or HLMP-3.

Another aspect of the invention includes the proteins encoded by the nucleic acid sequences. In still another embodiment, the invention relates to the identification of such proteins based on anti-LMP antibodies. In this embodiment, protein samples are prepared for Western blot analysis by lysing cells and separating the proteins by SDS-PAGE. The proteins are transferred to nitrocellulose by electroblotting as described by Ausubel, et al., Current Protocols in Molecular Biology, John Wiley and Sons (1987). After blocking the filter with instant nonfat dry milk (5 gm in 100 ml PBS), anti-LMP antibody is added to the filter and incubated for 1 hour at room temperature. The filter is washed thoroughly with phosphate buffered saline (PBS) and incubated with horseradish peroxidase (HRPO)-antibody conjugate for 1 hour at room temperature. The filter is again washed thoroughly with PBS and the antigen bands are identified by adding diaminobenzidine (DAB).

Monospecific antibodies are the reagent of choice in the present invention, and are specifically used to analyze patient cells for specific characteristics associated with the expression of LMP. "Monospecific antibody" as used herein is defined as a single antibody species or multiple antibody species with homogenous binding characteristics for LMP. "Homogeneous binding" as used herein refers to the ability of the antibody species to bind to a specific antigen or epitope, such as those associated with LMP, as described above. Monospecific antibodies to LMP are purified from mammalian antisera containing antibodies reactive against LMP or are prepared as monoclonal antibodies reactive with LMP using the technique of Kohler and Milstein. Kohler et al., Nature, 256, 495-497 (1975). The LMP specific antibodies are raised by immunizing animals such as, for example, mice, rats, guinea pigs, rabbits, goats or horses, with an appropriate concentration of LMP either with or without an immune adjuvant.

In this process, pre-immune serum is collected prior to the first immunization. Each animal receives between about 0.1 mg and about 1.0 mg of LMP associated with an acceptable immune adjuvant, if desired. Such acceptable adjuvants include, but are not limited to, Freund's complete, Freund's incomplete, alum-precipitate, water in oil emulsion containing Corynebacterium parvum and tRNA adjuvants. The initial immunization consists of LMP in, preferably, Freund's complete adjuvant injected at multiple sites either subcutaneously (SC), intraperitoneally (IP) or both. Each animal is bled at regular intervals, preferably weekly, to determine antibody titer. The animals may or may not receive booster injections following the initial immunization. Those animals receiving booster injections are generally given an equal amount of the antigen in Freund's incomplete adjuvant by the same route. Booster injections are given at about three week intervals until maximal titers are obtained. At about 7 days after each booster immunization or about weekly after a single immunization, the animals are bled, the serum collected, and aliquots are stored at about −20° C.

Monoclonal antibodies (mAb) reactive with LMP are prepared by immunizing inbred mice, preferably Balb/c mice, with LMP. The mice are immunized by the IP or SC route with about 0.1 mg to about 1.0 mg, preferably about 1 mg, of LMP in about 0.5 ml buffer or saline incorporated in an equal volume of an acceptable adjuvant, as discussed above. Freund's complete adjuvant is preferred. The mice receive an initial immunization on day 0 and are rested for about 3-30 weeks. Immunized mice are given one or more booster immunizations of about 0.1 to about 1.0 mg of LMP in a buffer solution such as phosphate buffered saline by the intravenous (IV) route. Lymphocytes from antibody-positive mice, preferably splenic lymphocytes, are obtained by removing the spleens from immunized mice by standard procedures known in the art. Hybridoma cells are produced by mixing the splenic lymphocytes with an appropriate fusion partner, preferably myeloma cells, under conditions which will allow the formation of stable hybridomas. Fusion partners may include, but are not limited to: mouse myelomas P3/NS1/Ag 4-1; MPC-11; S-194 and Sp 2/0, with Sp 2/0 being preferred. The antibody producing cells and myeloma cells are fused in polyethylene glycol, about 1,000 mol. wt., at concentrations from about 30% to about 50%. Fused hybridoma cells are selected by growth in hypoxanthine, thymidine and aminopterin in supplemented Dulbecco's Modified Eagles Medium (DMEM) by procedures known in the art. Supernatant fluids are collected from growth positive wells on about days 14, 18, and 21, and are screened for antibody production by an immunoassay such as solid phase immunoradioassay (SPIRA) using LMP as the antigen. The culture fluids are also tested in the Ouchterlony precipitation assay to determine the isotype of the mAb. Hybridoma cells from antibody positive wells are cloned by a technique such as the soft agar technique of MacPherson, "Soft Agar Techniques: Tissue Culture Methods and Applications", Kruse and Paterson (eds.), Academic Press (1973). See, also, Harlow, et al., Antibodies: A Laboratory Manual, Cold Spring Laboratory (1988).

Monoclonal antibodies may also be produced in vivo by injection of pristane-primed Balb/c mice, approximately 0.5 ml per mouse, with about $2\times10^6$ to about $6\times10^6$ hybridoma cells about 4 days after priming. Ascites fluid is collected at approximately 8-12 days after cell transfer and the monoclonal antibodies are purified by techniques known in the art.

In vitro production in anti-LMP mAb is carried out by growing the hydridoma cell line in DMEM containing about 2% fetal calf serum to obtain sufficient quantities of the specific mAb. The mAb are purified by techniques known in the art.

Antibody titers of ascites or hybridoma culture fluids are determined by various serological or immunological assays, which include, but are not limited to, precipitation, passive agglutination, enzyme-linked immunosorbent antibody (ELISA) technique and radioimmunoassay (RIA) techniques. Similar assays are used to detect the presence of the LMP in body fluids or tissue and cell extracts.

It is readily apparent to those skilled in the art that the above described methods for producing monospecific antibodies may be utilized to produce antibodies specific for polypeptide fragments of LMP, full-length nascent LMP polypeptide, or variants or alleles thereof.

In another embodiment, the invention is directed to alternative splice variants of HLMP-1. PCR analysis of human heart cDNA revealed mRNA for two HLMP alternative splice variants, named HLMP-2 and HLMP-3, that differ from HLMP-1 in a region between base pairs 325 and 444 in the HLMP-1 sequence. The HLMP-2 sequence has a 119 base pair deletion and an insertion of 17 base pairs in this region. These changes preserve the reading frame, resulting in a 423 amino acid protein, which compared to HLMP-1, has a net loss of 34 amino acids (40 amino acids deleted plus 6 inserted amino acids). HLMP-2 contains the c-terminal LIM domains that are present in HLMP-1.

Compared to HLMP-1, HLMP-3 has no deletions, but it does have the same 17 base pair insertion at position 444. This insertion shifts the reading frame, causing a stop codon at base pairs 459-461. As a result, HLMP-3 encodes a protein of 153 amino acids. This protein lacks the c-terminal LIM domains that are present in HLMP-1 and HLMP-2. The predicted size of the proteins encoded by HLMP-2 and HLMP-3 was confirmed by western blot analysis.

PCR analysis of the tissue distribution of the three splice variants revealed that they are differentially expressed, with specific isoforms predominating in different tissues. HLMP-1 is apparently the predominant form expressed in leukocytes, spleen, lung, placenta, and fetal liver. HLMP-2 appears to be the predominant isoform in skeletal muscle, bone marrow, and heart tissue. HLMP-3, however, was not the predominant isoform in any tissue examined.

Over-expression of HLMP-3 in secondary rat osteoblast cultures induced bone nodule formation (287.+-.56) similar to the effect seen for glucicorticoid (272. +-.7) and HLMP-1 (232. +-.200). Since HLMP-3 lacks the C-terminal LIM domains, these regions are not required for osteoinductive activity.

Over-expression of HLMP-2, however, did not induce nodule formation (11. +-.3). These data suggest that the amino acids encoded by the deleted 119 base pairs are necessary for osteoinduction. The data also suggest that the distribution of HLMP splice variants may be important for tissue-specific function. Surprisingly, we have shown that HLMP-2 inhibits steroid-induced osteoblast formation in secondary rat osteoblast cultures. Therefore, HLMP-2 may have therapeutic utility in clinical situations where bone formation is not desirable.

On Jul. 22, 1997, a sample of 10-4/RLMP in a vector designated pCMV2/RLMP (which is vector pRc/CMV2 with insert 10-4 clone/RLMP) was deposited with the American Type Culture Collection (ATCC), 12301 Parklawn Drive, Rockville, Md. 20852. The culture accession number for that deposit is 209153. On Mar. 19, 1998, a sample of the vector pHis-A with insert HLPM-1s was deposited at the American Type Culture Collection ("ATCC"). The culture accession number for that deposit is 209698. On Apr. 14, 2000, samples of plasmids pHAhLMP-2 (vector pHisA with cDNA insert derived from human heart muscle cDNA with HLMP-2) and pHAhLMP-3 (vector pHisA with cDNA insert derived from human heart muscle cDNA with HLMP-3) were deposited with the ATCC, 10801 University Blvd., Manassas, Va., 20110-2209, USA, under the conditions of the Budapest treaty. The accession numbers for these deposits are PTA-1698 and PTA-1699, respectively. These deposits, as required by the Budapest Treaty, will be maintained in the ATCC for at least 30 years and will be made available to the public upon the grant of a patent disclosing them. It should be understood that the availability of a deposit does not constitute a license to practice the subject invention in derogation of patent rights granted by government action.

In another embodiment, this invention is directed to cell expression systems and methods of use thereof to meet the demands of proteomics for large scale production of LMP proteins. According to this aspect of the invention, a method is developed to remedy the main drawback of the expression of heterologous proteins in non-mammalian hosts (e.g. bacteria, yeast, baculovirus). Inventors are thus the first to introduce a method for purifying and manufacturing LMP-1 protein by identifying LMP-1 protein by internal sequencing and assessing post-translational glycosylation.

Recombinant expression of protein factors has become a powerful tool for a variety of applications ranging from basic research to human therapy. Cultured mammalian cells have become the dominant system for the production of recombinant mammalian proteins for clinical applications because of their capacity for proper protein folding, assembly and post-translational modification.

However, the expression of heterologous proteins in non-mammalian hosts (e.g. bacteria, yeast, baculovirus) results in recombinant proteins that often display poor functional and structural properties due to a lack of proper folding and/or post-translational modifications. High-level mammalian recombinant protein production mostly relies on the establishment of stably expressing cell lines. Such procedures are not only labor-intensive and time consuming, but also precludes the expression of proteins whose biological activities interfere with cell growth.

In this embodiment of the invention, the inventors show that LMP-1 protein is expressed upon plasmid-mediated transformation of mammalian cells by purifying and characterizing the identity of the protein. The inventors have purified the recombinant proteins to a suitable level of homogeneity using a novel purification and detection methods with following features: (1) size fractionation of proteins prior to metal affinity chromatography to improve efficiency of affinity resin and (2) identification of tryptic fragments of purified protein.

The appeal of this approach is the short time span of a few days between DNA delivery and protein harvest. The improvements described in this invention are readily amenable to scale-up procedures.

In yet another embodiment of this invention, inventors determined whether the expressed protein undergoes any post-translational modification. According to this aspect of the invention inventors assess the presence of carbohydrate on LMP-1 polypeptide in any suitable cell expression system which includes prokaryotic (e.g. bacteria, blue green algae) and non-mammalian eukaryotic cells (e.g. insect cells, plant cells) as well as mammalian cells (e.g. A-549 cells). The inventions have further characterized the structural and functional role of the carbohydrate moiety in LMP-1 purified in normal human cells.

A549 cells, derived from a human lung adenocarcinoma, are not fully representative of normal human respiratory epithelium but have been a quick and useful in vitro model for protein expression studies. Allen and White, Am. J. Physiol., 274 (Lung Cell. Mol. Physiol. 18): L159-L164, (1998). Kazzaz et al, J. Biol. Chem., 271:15182-15186 (1996). Wong et al. J. Clin. Invest., 99: 2423-2428 (1997). The A-549 cell system has all the eukaryotic protein processing capabilities. It is generally accepted that A-549 cells can fold, modify, traffic and assemble newly synthesized polypeptides to produce highly authentic, soluble end products. The present invention provides that a full length LMP-1 is indeed expressed in A549 cells and milligram quantities of protein can be obtained from mammalian cell cultures.

According to this aspect of the invention, the inventors were able to determine that the protein did not contain carbohydrate as chemical analysis showed little or no N-acetyl glucosamine or N-acetyl galactosamine. These observations suggest to those of ordinary skill in the art that prokaryotic cell systems(e.g. bacteria) as well as non-mammalian eukaryotic cells (e.g. insect and plant cells) are suitable candidates to provide expression systems for determination of the LMP-1 mode of action and further its mass production.

In the final aspect of this invention, compositions of matter comprising LIM mineralization protein that are substantially free of carbohydrate moieties and are manufactured in accord to the instantly described method. Such compositions can further contain physiologically acceptable carrier system for in vivo administration. In assessing the nucleic acids, proteins, or antibodies of the invention, enzyme assays, protein purification, and other conventional biochemical methods are employed. DNA and RNA are analyzed by Southern blotting and Northern blotting techniques, respectively. Typically, the samples analyzed are size fractionated by gel electrophoresis. The DNA or RNA in the gels are then transferred to nitrocellulose or nylon membranes. The blots, which are replicas of sample patterns in the gels, were then hybridized with probes. Typically, the probes are radio-labeled, preferably with $^{32}$p, although one could label the probes with other signal-generating molecules known to those in the art. Specific bands of interest can then be visualized by detection systems, such as autoradiography.

For purposes of illustrating preferred embodiments of the present invention, the following, non-limiting examples are included. These results demonstrate the feasibility of inducing or enhancing the formation of bone using the LIM mineralization proteins of the invention, and the isolated nucleic acid molecules encoding those proteins.

EXAMPLES

Example 1

Calvarial Cell Culture

Rat calvarial cells, also known as rat osteoblasts ("ROB"), were obtained from 20-day pre-parturition rats as previously described. Boden. et al., Endocrinology, 137, 8, 3401-3407 (1996). Primary cultures were grown to confluence (7 days), trypsinized, and passed into 6-well plates ($1\times10^5$ cells/35 mm well) as first subculture cells. The subculture cells, which were confluent at day 0, were grown for an additional 7 days. Beginning on day 0, media were changed and treatments (Trm and/or BMPs) were applied, under a laminar flow hood, every 3 or 4 days. The standard culture protocol was as follows: days 1-7, MEM, 10% FBS, 50 μg/ml ascorbic acid, .+−.stimulus; days 8-14, BGJb medium, 10% FBS, 5 mM β-GlyP (as a source of inorganic phosphate to permit mineralization). Endpoint analysis of bone nodule formation and osteocalcin secretion was performed at day 14. The dose of BMP was chosen as 50 ng/ml based on pilot experiments in this system that demonstrated a mid-range effect on the dose-response curve for all BMPs studied.

Example 2

Antisense Treatment and Cell Culture

To explore the potential functional role of LMP-1 during membranous bone formation, we synthesized an antisense oligonucleotide to block LMP-1 mRNA translation and treated secondary osteoblast cultures that were undergoing differentiation initiated by glucocorticoid. Inhibition of RLMP expression was accomplished with a highly specific antisense oligonucleotide (having no significant homologies to known rat sequences) corresponding to a 25 bp sequence spanning the putative translational start site (SEQ. ID NO: 42). Control cultures either did not receive oligonucleotide or they received sense oligonucleotide. Experiments were performed in the presence (preincubation) and absence of lipofectamine. Briefly, 22 μg of sense or antisense RLMP oligonucleotide was incubated in MEM for 45 minutes at room temperature. Following that incubation, either more MEM or pre-incubated lipofectamine/MEM (7% v/v; incubated 45 minutes at room temperature) was added to achieve an oligonucleotide concentration of 0.2 μM. The resulting mixture was incubated for 15 minutes at room temperature. Oligonucleotide mixtures were then mixed with the appropriate medium, that is, MEM/Ascorbate/.+−.Trm, to achieve a final oligonucleotide concentration of 0.1 μM.

Cells were incubated with the appropriate medium (.+−.stimulus) in the presence or absence of the appropriate oligonucleotides. Cultures originally incubated with lipofectamine were re-fed after 4 hours of incubation (37° C.; 5% $CO_2$) with media containing neither lipofectamine nor oligonucleotide. All cultures, especially cultures receiving oligonucleotide, were re-fed every 24 hours to maintain oligonucleotide levels.

LMP-1 antisense oligonucleotide inhibited mineralized nodule formation and osteocalcin secretion in a dose-dependent manner, similar to the effect of BMP-6 oligonucleotide. The LMP-1 antisense block in osteoblast differentiation could not be rescued by addition of exogenous BMP-6, while the BMP-6 antisense oligonucleotide inhibition was reversed with addition of BMP-6. This experiment further confirmed the upstream position of LMP-1 relative to BMP-6 in the osteoblast differentiation pathway. LMP-1 antisense oligonucleotide also inhibited spontaneous osteoblast differentiation in primary rat osteoblast cultures.

Example 3

Quantitation of Mineralized Bone Nodule Formation

Cultures of ROBs prepared according to Examples 1 and 2 were fixed overnight in 70% ethanol and stained with von Kossa silver stain. A semi-automated computerized video image analysis system was used to quantitate nodule count and nodule area in each well. Boden. et al., Endocrinology, 137, 8, 3401-3407 (1996). These values were then divided to calculate the area per nodule values. This automated process was validated against a manual counting technique and demonstrated a correlation coefficient of 0.92 ($p<0.000001$). All data are expressed as the mean. +−.standard error of the mean (S.E.M.) calculated from 5 or 6 wells at each condition. Each experiment was confirmed at least twice using cells from different calvarial preparations.

Example 4

Quantitation of Osteocalcin Secretion

Osteocalcin levels in the culture media were measured using a competitive radioimmunoassay with a monospecific polygonal antibody (Pab) raised in our laboratory against the C-terminal nonapeptide of rat osteocalcin as described in Nanes. et al., Endocrinology, 127:588 (1990). Briefly, 1 μg of nonapeptide was iodinated with 1 mCi $^{125}$I—Na by the lactoperoxidase method. Tubes containing 200 ug of assay buffer (0.02 M sodium phosphate, 1 mM EDTA, 0.001% thimerosal, 0.025% BSA) received media taken from cell cultures or osteocalcin standards (0-12,000 fmole) at 100 ul/tube in assay buffer. The Pab (1:40,000; 100 μl) was then added, followed by the iodinated peptide (12,000 cpm; 100 μl). Samples tested for non-specific binding were prepared similarly but contained no antibody.

Bound and free PAbs were separated by the addition of 700 μl goat antirabbit IgG, followed by incubation for 18 hours at 4° C. After samples were centrifuged at 1200 rpm for 45 minutes, the supernatants were decanted and the precipitates counted in a gamma counter. Osteocalcin values were reported in fmole/100 μl, which was then converted to pmole/ml medium (3-day production) by dividing those values by 100. Values were expressed as the mean.+−.S.E.M. of triplicate determinations for 5-6 wells for each condition. Each experiment was confirmed at least two times using cells from different calvarial preparations.

Example 5

Effect of Trm and RLMP on Mineralization In Vitro

There was little apparent effect of either the sense or antisense oligonucleotides on the overall production of bone nodules in the non-stimulated cell culture system. When ROBs were stimulated with Trm, however, the antisense oligonucleotide to RLMP inhibited mineralization of nodules by>95%. The addition of exogenous BMP-6 to the oligonucleotide-treated cultures did not rescue the mineralization of RLMP-antisense-treated nodules.

Osteocalcin has long been synonymous with bone mineralization, and osteocalcin levels have been correlated with nodule production and mineralization. The RLMP-antisense oligonucleotide significantly decreases osteocalcin production, but the nodule count in antisense-treated cultures does not change significantly. In this case, the addition of exogenous BMP-6 only rescued the production of osteocalcin in RLMP-antisense-treated cultures by 10-15%. This suggests that the action of RLMP is downstream of, and more specific than, BMP-6.

Example 6

Harvest and Purification of RNA

Cellular RNA from duplicate wells of ROBs (prepared according to Examples 1 and 2 in 6-well culture dishes) was harvested using 4M guanidine isothiocyanate (GIT) solution to yield statistical triplicates. Briefly, culture supernatant was aspirated from the wells, which were then overlayed with 0.6 ml of GIT solution per duplicate well harvest. After adding the GIT solution, the plates were swirled for 5-10 seconds (being as consistent as possible). Samples were saved at −70° C. for up to 7 days before further processing.

RNA was purified by a slight modification of standard methods according to Sambrook, et al. Molecular Cloning: a Laboratory Manual, Chapter 7.19, 2$^{nd}$ Edition, Cold Spring Harbor Press (1989). Briefly, thawed samples received 60 μl 2.0 M sodium acetate (pH 4.0), 550 μl phenol (water saturated) and 150 μl chloroform:isoamyl alcohol (49:1). After vortexing, the samples were centrifuged (10000×g; 20 minutes; 4° C.), the aqueous phase transferred to a fresh tube, 600 μl isopropanol was added and the RNA precipitated overnight at −20° C.

Following the overnight incubation, the samples were centrifuged (10000×g; 20 minutes) and the supernatant was aspirated gently. The pellets were resuspended in 400 μl DEPC-treated water, extracted once with phenol:chloroform (1:1), extracted with chloroform:isoamyl alcohol (24:1) and precipitated overnight at −20° C. after addition of 40 μl sodium acetate (3.0 M; pH 5.2) and 1.0 ml absolute ethanol. To recover the cellular RNA, the samples were centrifuged (10000×g; 20 min), washed once with 70% ethanol, air dried for 5-10 minutes and resuspended in 20 μl of DEPC-treated water. RNA concentrations were calculated from optical densities that were determined with a spectrophotometer.

Example 7

Reverse Transcription-Polymerase Chain Reaction 25

Heated total RNA (5 μg in 10.5 μl total volume DEPC-$H_{20}$ at 65° C. for 5 minutes) was added to tubes containing 4 μl 5× MMLV-RT buffer, 2 μl dNTPs, 2 μl dT17 primer (10 pmol/ml), 0.5 μl RNAsin (40 U/ml) and 1 μl MMLV-RT (200 units/μl). The samples were incubated at 37° C. for 1 hour, then at 95° C. for 5 minutes to inactivate the MMLV-RT. The samples were diluted by addition of 80 μl of water.

Reverse-transcribed samples (5 μl) were subjected to polymerase-chain reaction using standard methodologies (50 μl total volume). Briefly, samples were added to tubes containing water and appropriate amounts of PCR buffer, 25 mM $MgCl_2$, dNTPs, forward and reverse primers for glyceraldehyde 3-phosphate dehydrogenase (GAP, a housekeeping gene) and/or BMP-6, $^{32}P$-dCTP, and Taq polymerase. Unless otherwise noted, primers were standardized to run consistently at 22 cycles (94° C., 30"; 58° C., 30"; 72° C., 20").

Example 8

Quantitation of RT-PCR Products by Polyacrylamide Gel Electrophoresis (PAGE) and PhosphorImager Analysis RT-PCR products received 5 μl/tube loading dye, were mixed, heated at 65° C. for 10 min and centrifuiged. Ten μl of each reaction was subjected to PAGE (12% polyacrylamide: bis; 15 V/well; constant current) under standard conditions. Gels were then incubated in gel preserving buffer (10% v/v glycerol, 7% v/v acetic acid, 40% v/v methanol, 43% deionized water) for 30 minutes, dried (80° C.) in vacuo for 1-2 hours and developed with an electronically-enhanced phosphoresence imaging system for 6-24 hours. Visualized bands were analyzed. Counts per band were plotted graphically.

Example 9

Differential Display PCR

RNA was extracted from cells stimulated with glucocorticoid (Trm, 1 nM). Heated, DNase-treated total RNA (5 μg in 10.5 μl total volume in DEPC-$H_2O$ at 65° C. for 5 minutes) was reverse transcribed as described in Example 7, but H-$T_{11}$ M (SEQ. ID. NO: 4) was used as the MMLV-RT primer. The resulting cDNAs were PCR-amplified as described above, but with various commercial primer sets (for example, H-$T_{11}$G (SEQ. ID NO: 4) and H-AP-10 (SEQ. ID NO: 5); GenHunter Corp, Nashville, Tenn.). Radio-labeled PCR products were fractionated by gel electrophoresis on a DNA sequencing gel. After electrophoresis, the resulting gels were dried in vacuo and autoradiographs were exposed overnight. Bands representing differentially-expressed cDNAs were excised from the gel and reamplified by PCR using the method of Conner. et al., Proc. Natl. Acad. Sci. USA, 88, 278 (1983). The products of PCR reamplification were cloned into the vector PCR-11 (TA cloning kit; InVitrogen, Carlsbad, Calif.).

Example 10

Screening of a UMR 106 Rat Osteosarcoma Cell cDNA Library

A UMR 106 library ($2.5\times10^{10}$ pfu/ml) was plated at $5\times10^4$ pfu/ml onto agar plates (LB bottom agar) and the plates were incubated overnight at 37° C. Filter membranes were overlaid onto plates for two minutes. Once removed, the filters were denatured, rinsed, dried and UV cross-linked. The filters were then incubated in pre-hyridization buffer (2× PIPES [pH 6.5], 5% formamide, 1% SDS and 100 μg/ml denatured salmon sperm DNA) for 2 h at 42° C. A 260 base-pair radio-labeled probe (SEQ. ID NO: 3; $^{32}P$ labeled by random priming) was added to the entire hybridization mix/filters, followed by hybridization for 18 hours at 42° C. The membranes were washed once at room temperature (10 min, 1×SSC, 0.1% SDS) and three times at 55° C. (15 min, 0.1×SSC, 0.1% SDS).

After they were washed, the membranes were analyzed by autoradiography as described above. Positive clones were plaque purified. The procedure was repeated with a second filter for four minutes to minimize spurious positives. Plaque-purified clones were rescued as lambda SK(−) phagemids. Cloned cDNAs were sequenced as described below.

Example 11

Sequencing of Clones

Cloned cDNA inserts were sequenced by standard methods. Ausubel, et al., Current Protocols in Molecular Biology, Wiley Interscience (1988). Briefly, appropriate concentrations of termination mixture, template and reaction mixture were subjected to an appropriate cycling protocol (95° C., 30 s; 68° C., 30 s; 72° C., 60 s; X25). Stop mixture was added to terminate the sequencing reactions. After heating at 92° C. for 3 minutes, the samples were loaded onto a denaturing 6% polyacrylamide sequencing gel (29:1 acrylamide:bisacrylamide). Samples were electrophoresed for about 4 hours at 60 volts, constant current. After electrophoresis, the gels were dried in vacuo and autoradiographed.

The autoradiographs were analyzed manually. The resulting sequences were screened against the databases maintained by the National Center for Biotechnology Information using the BLASTN program set with default parameters. Based on the sequence data, new sequencing primers were prepared and the process was repeated until the entire gene had been sequenced. All sequences were confirmed a minimum of three times in both orientations.

Nucleotide and amino acid sequences were also analyzed using the PCGENE software package (version 16.0). Percent homology values for nucleotide sequences were calculated by the program NALIGN, using the following parameters: weight of non-matching nucleotides, 10; weight of non-matching gaps, 10; maximum number of nucleotides considered, 50; and minimum number of nucleotides considered, 50.

For amino acid sequences, percent homology values were calculated using PALIGN. A value of 10 was selected for both the open gap cost and the unit gap cost.

Example 12

Cloning of RLMP cDNA

The differential display PCR amplification products described in Example 9 contained a major band of approximately 260 base pairs. This sequence was used to screen a rat osteosarcoma (UMR 106) cDNA library. Positive clones were subjected to nested primer analysis to obtain the primer sequences necessary for amplifying the full length cDNA. (SEQ. ID NOs: 11, 12, 29, 30 and 31). One of those positive clones selected for further study was designated clone 10-4.

Sequence analysis of the full-length cDNA in clone 10-4, determined by nested primer analysis, showed that clone 10-4 contained the original 260 base-pair fragment identified by differential display PCR. Clone 10-4 (1696 base pairs; SEQ ID NO: 2) contains an open reading frame of 1371 base pairs encoding a protein having 457 amino acids (SEQ. ID NO: 1). The termination codon, TGA, occurs at nucleotides 1444-1446. The polyadenylation signal at nucleotides 1675-1680, and adjacent poly$(A)^{+tail}$, was present in the 3' noncoding region. There were two potential N-glycosylation sites, Asn-Lys-Thr and Asn-Arg-Thr, at amino acid positions 113-116 and 257-259 in SEQ. ID NO: 1, respectively. Two potential cAMP- and cGMP-dependent protein kinase phosphorylation sites, Ser and Thr, were found at amino acid positions 191 and 349, respectively. There were five potential protein kinase C phosphorylation sites, Ser or Thr, at amino acid positions 3, 115, 166, 219, 442. One potential ATP/GTP binding site motif A (P-loop), Gly-Gly-Ser-Asn-Asn-Gly-Lys-Thr, was determined at amino acid positions 272-279.

In addition, two highly conserved putative LIM domains were found at amino acid positions 341-391 and 400-451. The putative LIM domains in this newly identified rat cDNA clone showed considerable homology with the LIM domains of other known LIM proteins. However, the overall homology with other rat LIM proteins was less than 25%. RLMP (also designated 10-4) has 78.5% amino acid homology to the human enigma protein (see U.S. Pat. No. 5,504,192), but only 24.5% and 22.7% amino acid homology to its closest rat homologs, CLP-36 and RIT-18, respectively.

Example 13

Northern Blot Analysis of RLMP Expression

Thirty μg of total RNA from ROBs, prepared according to Examples 1 and 2, was size fractionated by formaldehyde gel electrophoresis in 1% agarose flatbed gels and osmotically transblotted to nylon membranes. The blot was probed with a 600 base pair EcoR1 fragment of full-length 10-4 cDNA labeled with $^{32}$P-dCTP by random priming.

Northern blot analysis showed a 1.7 kb mRNA species that hybridized with the rLMP probe. RLMP mRNA was up-regulated approximately 3.7-fold in ROBs after 24 hours exposure to BMP-6. No up-regulation of RMLP expression was seen in BMP-2 or BMP-4-stimulated ROBs at 24 hours.

Example 14

Statistical Methods

For each reported nodule/osteocalcin result, data from 5-6 wells from a representative experiment were used to calculate the mean+−S.E.M. Graphs may be shown with data normalized to the maximum value for each parameter to allow simultaneous graphing of nodule counts, mineralized areas and osteocalcin.

For each reported RT-PCR, RNase protection assay or Western blot analysis, data from triplicate samples of representative experiments, were used to determine the mean+−S.E.M. Graphs may be shown normalized to either day 0 or negative controls and expressed as fold-increase above control values.

Statistical significance was evaluated using a one-way analysis of variance with post-hoc multiple comparison corrections of Bonferroni as appropriate. D. V. Huntsberger, "The Analysis of Variance", Elements of Statistical Variance, P. Billingsley (ed.), Allyn & Bacon Inc., Boston, Mass., 298-330 (1977) and SigmaStat, Jandel Scientific, Corte Madera, Calif. Alpha levels for significance were defined as $p<0.05$.

Example 15

Detection of Rat LIM Mineralization Protein by Western Blot Analysis

Polyclonal antibodies were prepared according to the methods of England, et al., Biochim. Biophys. Acta, 623, 171 (1980) and Timmer, et al., J. Biol. Chem., 268, 24863 (1993).

HeLa cells were transfected with pCMV2/rLMP. Protein was harvested from the transfected cells according to the method of Hair, et al., Leukemia Research, 20, 1 (1996). Western Blot Analysis of native RLMP was performed as described by Towbin, et al., Proc. Natl. Acad. Sci. USA, 76:4350 (1979).

Example 16

Synthesis of the Rat LMP-Unique (RLMPU) Derived Human PCR Product

Based on the sequence of the rat LMP-1 cDNA, forward and reverse PCR primers (SEQ. ID NOS: 15 and 16) were synthesized and a unique 223 base-pair sequence was PCR amplified from the rat LMP-1 cDNA. A similar PCR product was isolated from human MG63 osteosarcoma cell cDNA with the same PCR primers.

RNA was harvested from MG63 osteosarcoma cells grown in T-75 flasks. Culture supernatant was removed by aspiration and the flasks were overlayed with 3.0 ml of GIT solution per duplicate, swirled for 5-10 seconds, and the resulting solution was transferred to 1.5 ml eppendorf tubes (6 tubes with 0.6 ml/tube). RNA was purified by a slight modification of standard methods, for example, see Sambrook, et al., Molecular Cloning: A Laboratory Manual, Chapter 7, page 19, Cold Spring Harbor Laboratory Press (1989) and Boden, et al., Endocrinology, 138, 2820-2828 (1997). Briefly, the 0.6 ml samples received 60 μl 2.0 M sodium acetate (pH 4.0), 550 μl water saturated phenol and 150 μl chloroform:isoamyl alcohol (49:1). After addition of those reagents, the samples were vortexed, centrifuged (10000×g; 20 min; 4C) and the aqueous phase transferred to a fresh tube. Isopropanol (600, μl) was added and the RNA was precipitated overnight at −20° C. The samples were centrifuged (10000×g; 20 minutes) and the supernatant was aspirated gently. The pellets were resuspended in 400 μl of DEPC-treated water, extracted once with phenol:chloroform (1:1), extracted with chloroform:isoamyl alcohol (24:1) and precipitated overnight at −20° C. in 40 μl sodium acetate (3.0 M; pH 5.2) and 1.0 ml absolute ethanol. After precipitation, the samples were centrifuged (10000×g; 20 min), washed once with 70% ethanol, air dried for 5-10 minutes and resuspended in 20 μl of DEPC-treated water. RNA concentrations were derived from optical densities.

Total RNA (5 μg in 10.5 μl total volume in DEPC-$H_2O$) was heated at 65° C. for 5 minutes, and then added to tubes containing 4 μl 5 g MMLV-RT buffer, 2 μl dNTPS, 2, μl dT17 primer (10 pmol/ml), 0.5 μl RNA sin (40 U/ml) and 1 μl MMLV-RT (200 units/μl). The reactions were incubated at 37° C. for 1 hour. Afterward, the MMLV-RT was inactivated by heating at 95° C. for 5 minutes. The samples were diluted by addition of 80 μl water.

Transcribed samples (5 μl) were subjected to polymerase-chain reaction using standard methodologies (50 μl total volume). Boden, et al., Endocrinology, 138, 2820-2828 (1997); Ausubel, et al., "Quantitation of Rare DNAs by the Polymerase Chain Reaction", Current Protocols in Molecular Biology, Chapter 15.31-1, Wiley & Sons, Trenton, N.J. (1990). Briefly, samples were added to tubes containing water and appropriate amounts of PCR buffer (25 mM $MgCl_2$, dNTPs, forward and reverse primers (for RLMPU; SEQ. ID NOS: 15 and 16), $^{32}$P-dCTP, and DNA polymerase. Primers were designed to run consistently at 22 cycles for radioactive band detection and 33 cycles for amplification of PCR product for use as a screening probe (94° C., 30 sec, 58° C., 30 sec; 72° C., 20 sec).

Sequencing of the agarose gel-purified MG63 osteosarcoma-derived PCR product gave a sequence more than 95% homologous to the RLMPU PCR product. That sequence is designated HLMP unique region (HLMPU; SEQ. ID NO: 6).

Example 17

Screening of Reverse-Transcriptase-Derived MG63 cDNA

Screening was performed with PCR using specific primers (SEQ. ID NOS:16 and 17) as described in Example 7. A 717 base-pair MG63 PCR product was agarose gel purified and sequenced with the given primers a minimum of two times in both directions. The MG63 sequences were aligned against (SEQ. ID NOs: 12, 15, 16, 17, 18, 27 and 28). Sequences were confirmed each other and then against the full-length rat LMP cDNA sequence to obtain a partial human LMP cDNA sequence (SEQ. ID NO: 7).

Example 18

Screening of a Human Heart cDNA Library

Based on Northern blot experiments, it was determined that LMP-1 is expressed at different levels by several different tissues, including human heart muscle. A human heart cDNA library was therefore examined. The library was plated at $5\times10^4$ pfu/ml onto agar plates (LB bottom agar) and plates were grown overnight at 37° C. Filter membranes were overlaid onto the plates for two minutes. Afterward, the filters denatured, rinsed, dried, UV cross-linked and incubated in pre-hyridization buffer (2× PIPES [pH 6.5]; 5% formamide, 1% SDS, 100 g/ml denatured salmon sperm DNA) for 2 h at 42° C. A radio-labeled, LMP-unique, 223 base-pair probe ($^{32}$P, random primer labeling; SEQ ID NO: 6) was added and hybridized for 18 h at 42° C. Following hybridization, the membranes were washed once at room temperature (10 min, 1×SSC, 0.1% SDS) and three times at 55° C. (15 min, 0.1× SSC, 0.1% SDS). Double-positive plaque-purified heart library clones, identified by autoradiography, were rescued as lambda phagemids according to the manufacturers' protocols (Stratagene, La Jolla, Calif.).

Restriction digests of positive clones yielded cDNA inserts of varying sizes. Inserts greater than 600 base-pairs in length were selected for initial screening by sequencing. Those inserts were sequenced by standard methods as described in Example 11.

One clone, number 7, was also subjected to automated sequence analysis using primers corresponding to SEQ. ID NOS: 11-14, 16 and 27. The sequences obtained by these methods were routinely 97-100% homologous. Clone 7 (Partial Human LMP-1 cDNA from a heart library; SEQ. ID NO: 8) contained a sequence that was more than 87% homologous to the rat LMP cDNA sequence in the translated region.

Example 19

Determination of Full-Length Human LMP-1 cDNA

Overlapping regions of the MG63 human osteosarcoma cell cDNA sequence and the human heart cDNA clone 7 sequence were used to align those two sequences and derive a complete human cDNA sequence of 1644 base-pairs. NALIGN, a program in the PCGENE software package, was used to align the two sequences. The overlapping regions of the two sequences constituted approximately 360 base-pairs having complete homology except for a single nucleotide substitution at nucleotide 672 in the MG63 cDNA (SEQ. ID NO: 7) with clone 7 having an "A" instead of a "G" at the corresponding nucleotide 516 (SEQ. ID NO: 8).

The two aligned sequences were joined using SEQIN, another subprogram of PCGENE, using the "G" substitution of the MG63 osteosarcoma cDNA clone. The resulting sequence is shown in SEQ. ID NO: 9. Alignment of the novel human-derived sequence with the rat LMP-1 cDNA was accomplished with NALIGN. The full-length human LMP-1 cDNA sequence (SEQ. ID NO: 9) is 87.3% homologous to the translated portion of rat LMP-1 cDNA sequence.

Example 20

Determination of Deduced Amino Acid Sequence of Human LMP-1

The putative amino acid sequence of human LMP-1 was determined with the PCGENE subprogram TRANSL. The open reading frame in SEQ. ID NO: 9 encodes a protein comprising 457 amino acids (SEQ. ID NO: 10). Using the PCGENE subprogram Palign, the human LMP-1 amino acid sequence was found to be 94.1% homologous to the rat LMP-1 amino acid sequence.

Example 21

Determination of the 5 Prime Untranslated Region of the Human LMP cDNA

MG63 5' cDNA was amplified by nested RT-PCR of MG63 total RNA using a 5' rapid amplification of cDNA ends (5' RACE) protocol. This method included first strand cDNA synthesis using a lock-docking oligo (dT) primer with two degenerate nucleotide positions at the 3' end (Chenchik. et al., CLONTECHniques, X:5 (1995); Borson, et al., PC Methods Applic., 2, 144 (1993)). Second-strand synthesis is performed according to the method of Gubler, et al., Gene, 2, 263 (1983), with a cocktail of *Escherichia coli* DNA polymerase 1, RNase H, and *E. coli* DNA ligase. After creation of blunt ends with T4 DNA polymerase, double-stranded cDNA was ligated to the fragment (5'-CTAATACGACTCACTATAGGGCTCGAGCGGCCGCCCGGGCAGGT-3') (SEQ. ID NO: 19). Prior to RACE, the adaptor-ligated cDNA was diluted to a concentration suitable for Marathon RACE reactions (1:50). Adaptor-ligated double-stranded cDNA was then ready to be specifically cloned.

First-round PCR was performed with the adaptor-specific oligonucleotide, 5'-CCATCCTAATACGACTCACTATAGGGC-3' (AP1) (SEQ. ID NO: 20) as sense primer and a Gene Specific Primer (GSP) from the unique region described in Example 16 (HLMPU). The second round of PCR was performed using a nested primers GSP1-HLMPU (antisense/reverse primer) (SEQ. ID NO: 23) and GSP2-HLMPUF (SEQ. ID NO: 24) (see Example 16; sense/forward primer). PCR was performed using a commercial kit (Advantage cDNA PCR core kit; CloneTech Laboratories Inc., Palo Alto, Calif.) that utilizes an antibody-mediated, but otherwise standard, hot-start protocol. PCR conditions for MG63 cDNA included an initial hot-start denaturation (94° C., 60 sec) followed by: 94° C., 30 sec; 60° C., 30 sec; 68° C., 4 min; 30 cycles. The firstround PCR product was approximately 750 base-pairs in length whereas the nested PCR product was approximately 230 base-pairs. The first-round PCR product was cloned into linearized pCR 2.1 vector (3.9 Kb). The inserts were sequenced in both directions using M13 Forward and Reverse primers (SEQ. ID NO: 11; SEQ. ID NO: 12).

Example 22

Determination of Full-Length Human LMP-1 cDNA with 5 Prime UTR

Overlapping MG63 human osteosarcoma cell cDNA 5'-UTR sequence (SEQ. ID NO: 21), MG63 717 base-pair sequence (Example 17; SEQ. ID NO: 8) and human heart cDNA clone 7 sequence (Example 18) were aligned to derive a novel human cDNA sequence of 1704 base-pairs (SEQ. ID NO: 22). The alignment was accomplished with NALIGN, (both PCGENE and Omiga 1.0; Intelligenetics). Over-lapping sequences constituted nearly the entire 717 base-pair region (Example 17) with 100% homology. Joining of the aligned sequences was accomplished with SEQIN.

Example 23

Construction of LIM Protein Expression Vector

The construction of pHIS-5ATG LMP-1s expression vector was carried out with the sequences described in Examples 17 and 18. The 717 base-pair clone (Example 17; SEQ. ID NO: 7) was digested with ClaI and EcoRV. A small fragment (about 250 base-pairs) was gel purified. Clone 7 (Example 18; SEQ. ID NO: 8) was digested with ClaI and XbaI and a 1400 base-pair fragment was gel purified. The isolated 250 base-pair and 1400 base-pair restriction fragments were ligated to form a fragment of about 1650 base-pairs.

Due to the single nucleotide substitution in Clone 7 (relative to the 717 base-pair PCR sequence and the original rat sequence) a stop codon at translated base-pair 672 resulted. Because of this stop codon, a truncated (short) protein was encoded, hence the name LMP-1s. This was the construct used in the expression vector (SEQ. ID NO: 32). The full length cDNA sequence with 5' UTR (SEQ. ID NO: 33) was created by alignment of SEQ. ID NO: 32 with the 5' RACE sequence (SEQ. ID NO: 21). The amino acid sequence of LMP-1s (SEQ. ID NO: 34) was then deduced as a 223 amino acid protein and confirmed by Western blot (as in Example 15) to run at the predicted molecular weight of about 23.7 kD.

The pHis-ATG vector (InVitrogen, Carlsbad, Calif.) was digested with EcoRV and XbaI. The vector was recovered and the 650 base-pair restriction fragment was then ligated into the linearized pHis-ATG. The ligated product was cloned and amplified. The pHis-ATG-LMP-1s Expression vector, also designated pHIS-A with insert HLMP-1s, was purified by standard methods.

Example 24

Induction of Bone Nodule Formation and Mineralization In vitro with LMP Expression Vector Rat Calvarial cells were isolated and grown in secondary culture according to Example 1. Cultures were either unstimulated or stimulated with glucocorticoid (GC) as described in Example 1. A modification of the Superfect Reagent (Qiagen, Valencia, Calif.) transfection protocol was used to transfect 3 μg/well of each vector into secondary rat calvarial osteoblast cultures according to Example 25.

Mineralized nodules were visualized by Von Kossa staining, as described in Example 3. Human LMP-1s gene product over expression alone induced bone nodule formation (about 203 nodules/well) in vitro. Levels of nodules were approximately 50% of those induced by the GC positive control (about 412 nodules/well). Other positive controls included the pHisA-LMP-Rat expression vector (about 152 nodules/well) and the pCMV2/LMP-Rat-Fwd Expression vector (about 206 nodules/well), whereas the negative controls included the pCMV2/LMP-Rat-Rev. expression vector (about 2 nodules/well) and untreated (NT) plates (about 4 nodules/well). These data demonstrate that the human cDNA was at least as osteoinductive as the rat cDNA. The effect was less than that observed with GC stimulation, most likely due to sub-optimal doses of Expression vector.

Example 25

LMP-Induced Cell Differentiation In Vitro and In Vivo

The rat LMP cDNA in clone 10-4 (see Example 12) was excised from the vector by double-digesting the clone with NotI and ApaI overnight at 37° C. Vector pCMV2 MCS (InVitrogen, Carlsbad, Calif.) was digested with the same restriction enzymes. Both the linear cDNA fragment from clone 10-4 and pCMV2 were gel purified, extracted and ligated with T4 ligase. The ligated DNA was gel purified, extracted and used to transform *E. coli* JM109 cells for amplification. Positive agar colonies were picked, digested with NotI and ApaI and the restriction digests were examined by gel electrophoresis. Stock cultures were prepared of positive clones.

A reverse vector was prepared in analogous fashion except that the restriction enzymes used were XbaI and HindIII. Because these restriction enzymes were used, the LMP cDNA fragment from clone 10-4 was inserted into pRc/CMV2 in the reverse (that is, non-translatable) orientation. The recombinant vector produced is designated pCMV2/RLMP.

An appropriate volume of pCMV10-4 (60 nM final concentration is optimal [3 μg]; for this experiment a range of 0-600 nM/well [0-30 μg/well] final concentration is preferred) was resuspended in Minimal Eagle Media (MEM) to 450 μl final volume and vortexed for 10 seconds. Superfect was added (7.5 μl/ml final solution), the solution was vortexed for 10 seconds and then incubated at room temperature for 10 minutes. Following this incubation, MEM supplemented with 10% FBS (1 ml/well; 6 ml/plate) was added and mixed by pipetting.

The resulting solution was then promptly pipetted (1 ml/well) onto washed ROB cultures. The cultures were incubated for 2 hours at 37° C. in a humidified atmosphere containing 5% $CO_2$. Afterward, the cells were gently washed once with sterile PBS and the appropriate normal incubation medium was added.

Results demonstrated significant bone nodule formation in all rat cell cultures which were induced with pCMV10-4. For example, pCMV10-4 transfected cells produced 429 nodules/well. Positive control cultures, which were exposed to Trm, produced 460 nodules/well. In contrast, negative controls, which received no treatment, produced 1 nodule/well. Similarly, when cultures were transfected with pCMV10-4 (reverse), no nodules were observed.

For demonstrating de novo bone formation in vivo, marrow was aspirated from the hind limbs of 4-5 week old normal rats (mu/+; heterozygous for recessive athymic condition). The aspirated marrow cells were washed in alpha MEM, centrifuged, and RBCs were lysed by resuspending the pellet in 0.83% $NH_4Cl$ in 10 mM Tris (pH 7.4). The remaining marrow cells were washed 3 times with MEM and transfected for 2 hours with 9 μg of pCMV-LMP-1s (forward or reverse orientation) per $3\times10^6$ cells. The transfected cells were then washed 2 times with MEM and resuspended at a concentration of $3\times10^7$ cells/ml.

The cell suspension (100 μl) was applied via sterile pipette to a sterile 2×5 mm type I bovine collagen disc (Sulzer Orthopaedics, Wheat Ridge, Colo.). The discs were surgically implanted subcutaneously on the skull, chest, abdomen or dorsal spine of 4-5 week old athymic rats (rnu/rnu). The animals were scarified at 3-4 weeks, at which time the discs or surgical areas were excised and fixed in 70% ethanol. The fixed specimens were analyzed by radiography and undecalcified histologic examination was performed on 5 μm thick sections stained with Goldner Trichrome. Experiments were also performed using devitalized (guanidine extracted) demineralized bone matrix (Osteotech, Shrewsbury, N.J.) in place of collagen discs.

Radiography revealed a high level of mineralized bone formation that conformed to the form of the original collagen disc containing LMP-1s transfected marrow cells. No mineralized bone formation was observed in the negative control (cells transfected with a reverse-oriented version of the LMP-1s cDNA that did not code for a translated protein), and absorption of the carrier appeared to be well underway.

Histology revealed new bone trabeculae lined with osteoblasts in the LMP-1s transfected implants. No bone was seen along with partial resorption of the carrier in the negative controls.

Radiography of a further experiment in which 18 sets (9 negative control pCMV-LMP-REV & 9 experimental pCMV-LMP-1s) of implants were added to sites alternating between lumbar and thoracic spine in athymic rats demonstrated 0/9 negative control implants exhibiting bone formation (spine fusion) between vertebrae. All nine of the pCMV-LMP-1s treated implants exhibited solid bone fusions between vertebrae.

Example 26

The Synthesis of pHIS-5' ATG LMP-1s Expression Vector from the Sequences Demonstrated in Examples 2 and 3

The 717 base-pair clone (Example 17) was digested with ClaI and EcoRV (New England Biologicals, city, MA). A small fragment (about 250 base pairs) was gel purified. Clone No. 7 (Example 18) was digested with ClaI and XbaI. A 1400 base-pair fragment was gel purified from that digest. The isolated 250 base-pair and 1400 base-pair cDNA fragments were ligated by standard methods to form a fragment of about 1650 bp. The pHis-A vector (InVitrogen) was digested with EcoRV and XbaI. The linearized vector was recovered and ligated to the chimeric 1650 base-pair cDNA fragment. The ligated product was cloned and amplified by standard methods, and the phis-A-5' ATG LMP-1s expression vector, also denominated as the vector pHis-A with insert HLMP-1s, was deposited at the ATCC as previously described.

Example 27

The Induction of Bone Nodule Formation and Mineralization In Vitro with pHis-5' ATG LMP-1s Expression Vector Rat calvarial cells were isolated and grown in secondary culture according to Example 1. Cultures were either unstimulated or stimulated with glucocorticoid (GC) according to Example 1. The cultures were transfected with 3 μg of recombinant pHis-A vector DNA/well as described in Example 25. Mineralized nodules were visualized by Von Kossa staining according to Example 3.

Human LMP-1s gene product overexpression alone (i.e., without GC stimulation) induced significant bone nodule formation (about 203 nodules/well) in vitro. This is approximately 50% of the amount of nodules produced by cells exposed to the GC positive control (about 412 nodules/well). Similar results were obtained with cultures transfected with pHisA-LMP-Rat Expression vector (about 152 nodules/well) and pCMV2/LMP-Rat-Fwd (about 206 nodules/well). In contrast, the negative control pCMV2/LMP-Rat-Rev yielded (about 2 nodules/well), while approximately 4 nodules/well were seen in the untreated plates. These data demonstrate that the human LMP-1 cDNA was at least as osteoinductive as the rat LMP-1 cDNA in this model system. The effect in this experiment was less than that observed with GC stimulation; but in some the effect was comparable.

Example 28

LMP Induces Secretion of a Soluble Osteoinductive Factor

Overexpression of RLMP-1 or HLMP-1s in rat calvarial osteoblast cultures as described in Example 24 resulted in significantly greater nodule formation than was observed in the negative control. To study the mechanism of action of LIM mineralization protein conditioned medium was harvested at different time points, concentrated to 10 fold, sterile filtered, diluted to its original concentration in medium containing fresh serum, and applied for four days to untransfected cells.

Conditioned media harvested from cells transfected with RLMP-1 or HLMP-1s at day 4 was approximately as effective in inducing nodule formation as direct overexpression of RLMP-1 in transfected cells. Conditioned media from cells transfected with RLMP-1 or HLMP-1 in the reverse orientation had no apparent effect on nodule formation. Nor did conditioned media harvested from LMP-1 transfected cultures before day 4 induce nodule formation. These data suggest that expression of LMP-1 caused the synthesis and/or secretion of a soluble factor, which did not appear in culture medium in effective amounts until 4 days post transfection.

Since overexpression of rLMP-1 resulted in the secretion of an osteoinductive factor into the medium, Western blot analysis was used to determine if LMP-1 protein was present in the medium. The presence of RLMP-1 protein was assessed using antibody specific for LMP-1 (QDPDEE) (SEQ ID NO:44) and detected by conventional means. LMP-1 protein was found only in the cell layer of the culture and not detected in the medium.

Partial purification of the osteoinductive soluble factor was accomplished by standard 25% and 100% ammonium sulfate cuts followed by DE-52 anion exchange batch chromatography (100 mM or 500 mM NACl). All activity was observed in the high ammonium sulfate, high NaCl fractions. Such localization is consistent with the possibility of a single factor being responsible for conditioning the medium.

Example 29

Transfection of A-549 Cells

A-549 cells were grown in F12K medium (Gibco, Grand Island, N.Y.) in a humidified 10% $CO_2$ incubator at 37° C. supplemented with 10% non-heat-inactivated fetal bovine serum (Atlanta Biologicals, Norcross, Ga.). The 1623-bp cDNA for LMP-1 was cloned into the mammalian expression vector pHisA/pcDNA 3.1 following standard methods. The over-expressed LMP-1 contains a 6His-fusion tag at the N-terminus to facilitate affinity purification. The plasmid construct (10 ug/100 mm plate) was incubated for 2 h with A-549 cells using 60 ul of Superfect (Qiagen, Valencia, Calif.) per plate in 10 ml medium and the cultures were incubated for 2 days. Cells from 50×100 mm plates were harvested with phosphate-buffered saline by scraping with rubber policemen.

Example 30

Preparation of Nuclear and Cytoplasmic Protein Fractions from A-549 Cells

The A-549 cell pellets were resuspended in low salt buffer (20 mM HEPES, pH 7.9, 10 mM KCl, 1 mM EGTA, 1 mM EDTA, 0.2% Nonidet P-40, 10% Glycerol, 1 mM phenylmethylsulfonyl fluoride and 1 ug/ml of protease inhibitor mix (Sigma), incubated on ice for 10 min, and centrifuged (8000× g, 2 min, 4° C.). Supernatants (cytoplasmic fraction) were collected for further analysis. The nuclear pellets were suspended in high salt buffer (low salt buffer with 600 mM KCl, 20% glycerol), incubated on ice for 30 min and centrifuged as before. Supernatants were collected as the nuclear fraction. Both cytoplasmic and nuclear fractions were alquoted and stored frozen at −20° C. until further use.

Example 31

Purification of Recombinant LMP-1 from Cellular Extracts

Size-exclusion chromatography of the cellular proteins was carried out on a Sephacryl S-300 column connected to the AKTA FPLC System (Amersham Biosciences, Piscataway, N.J.). The column was pre-calibrated with known low- and high-molecular weight protein markers from gel filtration calibration kits (Amersham Biosciences, Piscataway, N.J.) in 50 mM sodium phosphate, 150 mM NaCl, pH 7.0 buffer. The marker proteins were thyroglobulin (molecular weight (Mw) 669 kDa), ferritin (Mw 440 kDa), catalase (Mw 232 kDa), aldolase (Mw 158 kDa), albumin (Mw 67 kDa), ovalbumin (Mw 43 kDa), chymotrypsinogen A (Mw 25 kDa), and ribonuclease A (Mw 13.7 kDa).

The cell pellets were suspended in 100 ml of ice-cold lysis buffer (20 mM phosphate buffer, pH 7.0 containing 50 mM Tris-HCl, pH 7.5 and 5 M NaCl). The uniform cell suspension was centrifuged at 10,000 g (Beckman #17 Rotor, 13,000 RPM) at 4° C. and the supernatant was applied onto a Sephacryl S-300 column (HiPrep 16×60) using AKTA FPLC system with Unicorn 3.1 software (Amersham Pharmacia Biotech) at a flow rate of 1 ml/min. Fractions (4 ml) were collected immediately after the void volume ($V_0$) (35 ml).

The proteins were applied onto $Ni^{++}$-affinity column (5 ml resin) previously equilibrated with 4×5 ml of buffer. Non-specific and low-affinity proteins were washed off the column with 3×10 ml of 20 mM phosphate buffer, pH 6.0 containing urea (8 M), NaCl (50 mM) and imidazole (20 mM). Affinity-bound proteins were eluted using 3×10 ml washes with 20 mM phosphate buffer, pH 4.0 containing urea (8 M), NaCl (50 mM). The eluates were combined and concentrated by spinning at 2000 g using a centriprep YM 50 ultrafiltration device. Flow-thru, washes and eluate were concentrated using a centriprep device and analysed by SDS-PAGE and western blotting. LMP-1 antibodies raised in rabbit for the peptide epitope from the osteogenic region of LMP-1: ADPPRYTFAPSVSLNKTARPFGAPPP (SEQ. ID NO:43)(the unique central region of LMP-1) were used for western blotting. Affinity eluted fractions were dialyzed against 20 mM Tris-HCl pH 7.5 (Buffer A) over night at 4° C. using a 10 kDa cut-off membrane for cation-exchange chromatography.

A HiTrap SP Sepharose (FF) cation exchange column, 1 ml (Pharmacia) was equilibrated in buffer A. Protein sample was syringe filtered using a 0.2u membrane and applied onto the column in buffer A. The bound proteins were eluted using the AKTA-FPLC system (Amersham-Pharmacia Biotech) by generating a linear gradient of NaCl from 0 to 1.0 M over 20 min at a flow rate of 1 ml/min. Finally the column was washed with 20% ethanol and stored until further use at 4° C. Fractions (1 ml) were diluted 3-fold (5 ul of sample plus 10 ul of water to reduce the salt concentration) and analysed by SDS-PAGE followed by western blotting using specific primary antibodies and horse radish peroxidase labeled secondary antibodies. Fractions containing recombinant protein (based on western blot) were pooled, concentrated and de-salted using the centriprep devices (Amicon). Protein samples were stored at −70° C., until further use, at this stage. Fractions containing unwanted contaminant proteins were discarded.

Protein quantitation was performed with protein assay reagent (BioRad) using BSA as standard. Due to poor dye binding by LMP-1 (abundance of Pro, Gly, Ser and Cys residues), more accurate protein amounts were determined from the overall yield of peptides from trypsin digestion and mass spectrometric analysis. The collective yield of the recombinant LMP-1 protein was about 75-100 ug from 120× 100 mm cell culture plates (from three batches of 40 plates each).

Example 32

SDS-PAGE and Western Blotting

SDS-PAGE is performed using 10% gels according to well known techniques and the electrophoresed proteins were transferred from the gel to a nitrocellulose membrane at 50 volts (constant) for 2 hrs. The membranes were blocked with 25 ml 5% milk protein for 1 hour at room temperature. Membranes were incubated with LMP-1 antibody at a dilution of 1:5000 (5 ul/25 ml of Tris-buffered saline containing 0.1% Tween 20) gently shaking for 2 hours at room temperature. Membranes were washed with 25 ml of TBST for 5 min. The washes were repeated two times. Membranes were incubated with anti-rabbit goat IgG-linked to horse radish peroxidase (NEF 812, NEN, Boston) diluted 1:5000 in 25 ml TBST for 1 hour. Membranes were washed three times, 5-min each with 25 ml of TBST as before. Chemiluminescent substrate reagent A (2 ml) and reagent B (2 ml) were mixed and applied to the membrane. The damp-dried membrane was exposed to X-ray film for signal detection.

Example 33

Sugar Composition Analysis

Sugar compositions were determined as described previously (Yasuno, S., Murata) (Sangadala et al 2001). Briefly, the purified protein (100 μg) was dissolved in 20 μl distilled water in a test tube to which 4 M TFA (20 μl, for neutral sugars) or 8 M HCl (20 μl, for amino sugars) was added. The test tube was incubated at 100° C. in a hot block bath. After 4 hr (neutral sugars) or 6 hr (amino sugars), the tube was cooled to room temperature and the acid was removed by using a centrifugal concentrator at 35° C. The dried sample was derivatized with ABEE in the presence of borane-pyridine complex at 80° C. After 1 hr, the reaction mixture was cooled to room temperature. Distilled water (200 μl) and an equal volume of chloroform were added to the reaction mixture. After vigorous vortexing, the sample was centrifuged (6000×g, 1 min). The upper aqueous layer was analyzed by reversed-phase HPLC under the following conditions: column, Wakosil-II 5C18HG (4.6×150 mm); solvent, A 0.02% TFA/$CH_3CN$ (90/10), B 0.02% TFA/$CH_3CN$ (50/50); program, 0-45 min (B conc. 0%), 45-55 min (B conc. 100%), 55-70 min (B conc. 0%); flow rate, 1 ml/min; temp., 45° C.; detection, absorbance at 305 nm. The monosaccharide and amino monosaccharide standards used were N-acetyl glucosamine, N-acetyl galactosamine, glucose, galactose, mannose, xylose, and L-fucose.

Example 34

'In-Gel' Digestion of LMP-1 by Trypsin

SDS-PAGE gels were stained with 0.25% Coomassie briliant blue in 45% methanol and 10% acetic acid and destained in 35% methanol with 10% acetic acid. The protein bands corresponding to a positive signal on western blots were sliced from the gel, soaked in 50% methanol with 0.1 M $NH_4HCO_3$ and mixed vigorously overnight. The wash solution was changed once and incubated for 2 hr. The clear gel bands were then soaked in water for 2 hr followed by soaking in 25 mM $NH_4HCO_3$ for 5 min. The wet gel pieces were smashed into fine pieces in Eppendorf tubes (0.5 ml). Trypsin (Promega) digestion was performed in 25 mM $NH_4HCO_3$ (pH 8.0) overnight at 37° C. Following digestion, peptides were extracted twice with acetonitrile and aliquots were lyophilyzed. (Bernardo et al, Wilkins et al, Winters et al).

Example 35

Preparation of Peptide Samples for Mass Spectrometry Analysis

Peptide samples were purified and concentrated using a Zip Tip (Millipore) which has $C_{18}$ resin fixed at its end. The resin was rinsed according to the manufacture's instructions with 10 μl of 0.1% trifluoroacetic acid (TFA) and 50% acetonitrile (ACN). Peptides were eluted in 10 μl 1:1 ACN-0.1% TFA. A 0.5 μl volume of the concentrated peptide-containing sample was mixed with 0.5 μl of a saturated solution of α-cyano-4-hydroxycinnamic acid. Each sample (0.5 ul) was spotted on the mass spectrometer sample plate (Tremoulet et al).

Example 36

Separation of Peptides by HPLC

After trypsin digestion, the mixture (85%) of LMP-1 peptides were separated by capillary reversed-phase HPLC using the method described before [Hubalek, F., Edmondson]. The peptide fragments were separated by small bore reverse phase HPLC on a Vydac $C_{18}$ column (4.6×250 mm) using a gradient HPLC system (Waters). The chromatographic run was performed with an aqueous phase containing 0.1% trifluoroacetic acid and organic phase containing 0.085% trifluoroacetic acid in acetonitrile with a flow rate of 0.5 ml/min. The gradient used for separation was 2-60% of acetonitrile for 40 min; the total run time was 60 min. The collected peptides were subjected to internal fragment N-terminal sequence analysis by standard Edman degradation (Procise 494 HT protein sequencer, Applied Biosystems, Foster City, Calif.). The eluate absorbing at 210 nm was manually collected for sequence analysis.

Example 37

Protein Identification and Amino Acid Sequence Analysis

In order to increase sequence coverage of LMP-1, aliquots of HPLC fractions of the digest also were analyzed by MALDITOF/TOF MS/MS using a model 4700 Proteomics Analyzer (Applied Biosystems). For each fraction, an MS spectrum was initially collected. For post source decay analysis, the HPLC-purified peptide was subjected to ion generation by post-source decay (Chaurand P 1999). A matrix-assisted laser desorption ionization-post-source decay (MALDI-PSD) time-of-flight spectrum was recorded using alpha-cyano-4-hydroxy cinnamic acid as a matrix; acquisition was at 27.5 kV under continuous extraction conditions; reflector voltage was stepped from 30 to 1.27 kV, and the spectrum was constructed using the FAST™ method from Bruker-Daltonic (Bremen, Germany). Using the manufacturer's GPS Explorer 2.0 software, the MS and MS/MS data were submitted to a MASCOT search engine (www.matrixscience.com/) for positive identification. The NCBI non-redundant database and the Mammalia taxonomy were used for these and all other searches.

Example 38

Database Searches for Protein Identification

Monoisotopic peptide masses obtained from mass spectra were searched against the SWISS-PROT, NCBInr and MSDB databases using the MASCOT search program. The following parameters were used in the searches: mammalian, human, MS/MS Ion Search, protein mass of 50 kDa, trypsin digest with two missed cleavages, fragment ion mass tolerance of ±75 ppm and possible oxidation of methionine. The resulting protein hits were scored using a probability based Mowse score. The score is −10*Log (P), where P is the probability that the observed match is a random event.

Example 39

Gene Therapy in Lumbar Spine Fusion Mediated by Low Dose Adenovirus

This study determined the optimal dose of adenoviral delivery of the LMP-1 cDNA (SEQ. ID NO: 2) to promote spine fusion in normal, that is, immune competent, rabbits.

A replication-deficient human recombinant adenovirus was constructed with the LMP-1 cDNA (SEQ. ID NO: 2) driven by a CMV promoter using the Adeno-Quest™ Kit (Quantum Biotechnologies, Inc., Montreal). A commercially available (Quantum Biotechnologies, Inc., Montreal) recombinant adenovirus containing the beta-galactosidase gene was used as a control.

Initially, an in vitro dose response experiment was performed to determine the optimal concentration of adenovirus-delivered LMP-1 ("AdV-LMP-1") to induce bone differentiation in rat calvarial osteoblast cultures using a 60-minute transduction with a multiplicity of infection ("MOI") of 0.025, 0.25, 2.5, or 25 plaque-forming units (pfu) of virus per cell. Positive control cultures were differentiated by a 7-day exposure to $10^9$ M glucocorticoid ("GC"). Negative control cultures were left untreated. On day 14, the number of mineralized bone nodules was counted after von Kossa staining of the cultures, and the level of osteocalcin secreted into the medium (pmol/mL) was measured by radioimmunoassay (mean±SEM).

The results of this experiment are shown in Table 1. Essentially no spontaneous nodules formed in the untreated negative control cultures. The data show that a MOI equal to 0.25 pfu/cell is most effective for osteoinducing bone nodules, achieving a level comparable to the positive control (GC). Lower and higher doses of adenovirus were less effective.

TABLE 1

| | Outcome | | | | | |
|---|---|---|---|---|---|---|
| | | | Adv-LMP-Dose (MOI) | | | |
| | Neg Ctrl. | GC | 0.025 | 0.25 | 2.5 | 25 |
| Bone Nodules | 0.5 ± 0.2 | 188 ± 35 | 79.8 ± 13 | 145.1 ± 13 | 26.4 ± 15 | 87.6 ± 2 |
| Osteoclacin | 1.0 ± 0.1 | 57.8 ± 9 | 28.6 ± 11 | 22.8 ± 1 | 18.3 ± 3 | 26.0 ± 2 |

In vivo experiments were then performed to determine if the optimal in vitro dose was capable of promoting intertransverse process spine fusions in skeletally mature New Zealand white rabbits. Nine rabbits were anesthetized and 3 cc of bone marrow was aspirated from the distal femur through the intercondylar notch using an 18 gauge needle. The buffy coat was then isolated, a 10-minute transduction with AdV-LMP-1 was performed, and the cells were returned to the operating room for implantation. Single level posterolateral lumbar spine arthrodesis was performed with decortication of transverse processes and insertion of carrier (either rabbit devitalized bone matrix or a collagen sponge) containing 8-15 million autologous nucleated buffy coat cells transduced with either AdV-LMP-1 (MOI=0.4) or AdV-BGal (MOI=0.4). Rabbits were euthanized after 5 weeks and spine fusions were assessed by manual palpation, plain x-rays, CT scans, and undecalcified histology.

The spine fusion sites that received AdV-LMP-1 induced solid, continuous spine fusion masses in all nine rabbits. In contrast, the sites receiving AdV-BGal, or a lower dose of AdV-LMP-1 (MOI=0.04) made little or no bone and resulted in spine fusion at a rate comparable to the carrier alone (<40%). These results were consistent as evaluated by manual palpation, CT scan, and histology. Plain radiographs, however, sometimes overestimated the amount of bone that was present, especially in the control sites. LMP-1 cDNA delivery and bone induction was successful with both of the carrier materials tested. There was no evidence of systemic or local immune response to the adenovirus vector.

These data demonstrate consistent bone induction in a previously validated rabbit spine fusion model which is quite challenging. Furthermore, the protocol of using autogenous bone marrow cells with intraoperative ex vivo gene transduction (10 minutes) is a more clinically feasible procedure than other methods that call for overnight transduction or cell expansion for weeks in culture. In addition, the most effective dose of recombinant adenovirus (MOI=0.25) was substantially lower than doses reported in other gene therapy applications (MOI 40-500). We believe this is due to the fact that LMP-1 is an intracellular signaling molecule and may have powerful signal amplification cascades. Moreover, the observation that the same concentration of AdV-LMP-1 that induced bone in cell culture was effective in vivo was also surprising given the usual required increase in dose of other growth factors when translating from cell culture to animal experiments. Taken together, these observations indicate that local gene therapy using adenovirus to deliver the LMP-1 cDNA is possible and the low dose required will likely minimize the negative effects of immune response to the adenovirus vector.

Example 40

Use of Peripheral Venous Blood Nucleated Cells (Buffy Coat) for Gene Therapy with LMP-1 cDNA to Make Bone In four rabbits we performed spine fusion surgery as above (Example 29) except the transduced cells were the buffy coat from venous blood rather than bone marrow. These cells were transfected with Adeno-LMP or pHIS-LMP plasmid and had equivalent successful results when bone marrow cells were used. This discovery of using ordinary venous blood cells for gene delivery makes gene therapy more feasible clinically since it avoids painful marrow harvest under general anesthesia and yields two times more cells per mL of starting material.

Example 41

Isolation of Human LMP-1 Splice Variants

Intron/Exon mRNA transcript splice variants are a relatively common regulatory mechanism in signal-transduction and cellular/tissue development. Splice variants of various genes have been shown to alter protein-protein, protein-DNA, protein-RNA, and protein-substrate interactions. Splice variants may also control tissue specificity for gene expression allowing different forms (and therefore functions) to be expressed in various tissues. Splice variants are a common regulatory phenomenon in cells. It is possible that the LMP splice variants may result in effects in other tissues such as nerve regeneration, muscle regeneration, or development of other tissues.

To screen a human heart cDNA library for splice variants of the HLMP-1 sequence, a pair of PCR primer corresponding to sections of SEQ. ID NO: 22 was prepared. The forward PCR primer, which was synthesized using standard techniques, corresponds to nucleotides 35-54 of SEQ. ID NO: 22. It has the following sequence:

(SEQ. ID NO: 35)
5' GAGCCGGCATCATGGATTCC 3'

The reverse PCR primer, which is the reverse complement of nucleotides 820-839 in SEQ. ID NO: 22, has the following sequence:

(SEQ. ID NO: 36)
5' GCTGCCTGCACAATGGAGGT 3'

The forward and reverse PCR primers were used to screen human heart cDNA (ClonTech, Cat No. 7404-1) for sequences similar to HLMP-1 by standard techniques, using a cycling protocol of 94° C. for 30 seconds, 64° C. for 30 seconds, and 72° C. for 1 minute, repeated 30 times and followed by a 10 minute incubation at 72° C. The amplification cDNA sequences were gel-purified and submitted to the Emory DNA Sequence Core Facility for sequencing. The clones were sequenced using standard techniques and the sequences were examined with PCGENE (intelligenetics; Programs SEQUIN and NALIGN) to determine homology to SEQ. ID NO: 22. Two homologous nucleotide sequences with putative alternative splice sites compared to SEQ. ID NO: 22 were then translated to their respective protein products with Intelligenetic's program TRANSL.

One of these two novel human cDNA sequences (SEQ. ID NO: 37) comprises 1456 bp:

```
  3 CGACGCAGAG CAGCGCCCTG GCCGGGCCAA GCAGGAGCCG GCATCATGGA TTCCTTCAAG

 60 GTAGTGCTGG AGGGGCCAGC ACCTTGGGGC TTCCGGCTGC AAGGGGGCAA GGACTTCAAT

120 GTGCCCCTCT CCATTTCCCG GCTCACTCCT GGGGGCAAAG CGGCGCAGGC CGGAGTGGCC

180 GTGGGTGACT GGGTGCTGAG CATCGATGGC GAGAATGCGG GTAGCCTCAC ACACATCGAA
```

-continued

```
240 GCTCAGAACA AGATCCGGGC CTGCGGGGAG CGCCTCAGCC TGGGCCTCAG CAGGGCCCAG

300 x x CCGGTTCAGA GCAAACCGCA GAAGGTGCAG ACCCCTGACA AACAGCCGCT CCGACCGCTG

360 GTCCCAGATG CCAGCAAGCA GCGGCTGATG GAGAACACAG AGGACTGGCG GCCGCGGCCG

420 GGGACAGGCC AGTCGCGTTC CTTCCGCATC CTTGCCCACC TCACAGGCAC CGAGTTCATG

480 CAAGACCCGG ATGAGGAGCA CCTGAAGAAA TCAAGCCAGG TGCCCAGGAC AGAAGCCCCA

540 GCCCCAGCCT CATCTACACC CCAGGAGCCC TGGCCTGGCC CTACCGCCCC CAGCCCTACC

600 AGCCGCCCGC CCTGGGCTGT GGACCCTGCG TTTGCCGAGC GCTATGCCCC GGACAAAACG

660 AGCACAGTGC TGACCCGGCA CAGCCAGCCG GCCACGCCCA CGCCGCTGCA GAGCCGCACC

720 TCCATTGTGC AGGCAGCTGC CGGAGGGGTG CCAGGAGGGG GCAGCAACAA CGGCAAGACT

780 CCCGTGTGTC ACCAGTGCCA CAAGGTCATC CGGGGCCGCT ACCTGGTGGC GTTGGGCCAC

840 GCGTACCACC CGGAGGAGTT TGTGTGTAGC CAGTGTGGGA AGGTCCTGGA AGAGGGTGGC

900 TTCTTTGAGG AGAAGGGCGC CATCTTCTGC CCACCATGCT ATGACGTGCG CTATGCACCC

960 AGCTGTGCCA AGTGCAAGAA GAAGATTACA GGCGAGATCA TGCACGCCCT GAAGATGACC

1020 TGGCACGTGC ACTGCTTTAC CTGTGCTGCC TGCAAGACGC CCATCCGGAA CAGGGCCTTC

1080 TACATGGAGG AGGGCGTGCC CTATTGCGAG CGAGACTATG AGAAGATGTT TGGCACGAAA

1140 TGCCATGGCT GTGACTTCAA GATCGACGCT GGGGACCGCT TCCTGGAGGC CCTGGGCTTC

1200 AGCTGGCATG ACACCTGCTT CGTCTGTGCG ATATGTCAGA TCAACCTGGA AGGAAAGACC

1260 TTCTACTCCA AGAAGGACAG GCCTCTCTGC AAGAGCCATG CCTTCTCTCA TGTGTGAGCC

1320 CCTTCTGCCC ACAGCTGCCG CGGTGGCCCC TAGCCTGAGG GGCCTGGAGT CGTGGCCCTG

1380 CATTTCTGGG TAGGGCTGGC AATGGTTGCC TTAACCCTGG CTCCTGGCCC GACCCTGGGC

1440 TCCCGGGCCC TGCCCA

1456
```

Reading frame shifts caused by the deletion of a 119 bp fragment (between X) and the addition of a 17 bp fragment (underlined) results in a truncated gene product having the following derived amino acid sequence (SEQ. ID NO: 38):

```
4 Met Asp Ser Phe Lys Val Val Leu Glu Gly Pro Ala

Pro Trp Gly Phe 1 5 10 15 Arg Leu Gln Gly Gly Lys

Asp Phe Asn Val Pro Leu Ser Ile Ser Arg 20 25 30

Leu Thr Pro Gly Gly Lys Ala Ala Gln Ala Gly Val

Ala Val Gly Asp 35 40 45 Trp Val Leu Ser Ile Asp

Gly Glu Asn Ala Gly Ser Leu Thr His Ile 50 55 60

Glu Ala Gln Asn Lys Ile Arg Ala Cys Gly Glu Arg

Leu Ser Leu Gly 65 70 75 80 Leu Ser Arg Ala Gln

Pro Val Gln Asn Lys Pro Gln Lys Val Gln Thr 85 90

95 Pro Asp Lys Gln Pro Leu Arg Pro Leu Val Pro Asp

Ala Ser Lys Gln 100 105 110 Arg Leu Met Glu Asn

Thr Glu Asp Trp Arg Pro Arg Pro Gly Thr Gly 115

120 125 Gln Ser Arg Ser Phe Arg Ile Leu Ala His

Leu Thr Gly Thr Glu Phe 130 135 140 Met Gln Asp
```

-continued

```
Pro Asp Glu Glu His Leu Lys Lys Ser Ser Gln Val

Pro 145 150 155 160 Arg Thr Glu Ala Pro Ala Pro

Ala Ser Ser Thr Pro Gln Glu Pro Trp 165 170 175

Pro Gly Pro Thr Ala Pro Ser Pro Thr Ser Arg Pro

Pro Trp Ala Val 180 185 190 Asp Pro Ala Phe Ala

Glu Arg Tyr Ala Pro Asp Lys Thr Ser Thr Val 195

200 205 Leu Thr Arg His Ser Gln Pro Ala Thr Pro

Thr Pro Leu Gln Ser Arg 210 215 220 Thr Ser Ile

Val Gln Ala Ala Ala Gly Gly Val Pro Gly Gly Gly

Ser 225 230 235 240 Asn Asn Gly Lys Thr Pro Val

Cys His Gln Cys His Gln Val Ile Arg 245 250 255

Ala Arg Tyr Leu Val Ala Leu Gly His Ala Tyr His

Pro Glu Glu Phe 260 265 270 Val Cys Ser Gln Cys

Gly Lys Val Leu Glu Glu Gly Gly Phe Phe Glu 275

280 285 Glu Lys Gly Ala Ile Phe Cys Pro Pro Cys

Tyr Asp Val Arg Tyr Ala 290 295 300 Pro Ser Cys

Ala Lys Cys Lys Lys Lys Ile Thr Gly Glu Ile Met
```

-continued

```
His 305 310 315 320 Ala Leu Lys Met Thr Trp His

Val Leu Cys Phe Thr Cys Ala Ala Cys 325 330 335

Lys Thr Pro Ile Arg Asn Arg Ala Phe Tyr Met Glu

Glu Gly Val Pro 340 345 350 Tyr Cys Glu Arg Asp

Tyr Glu Lys Met Phe Gly Thr Lys Cys Gln Trp 355

360 365 Cys Asp Phe Lys Ile Asp Ala Gly Asp Arg

Phe Leu Glu Ala Leu Gly 370 375 380 Phe Ser Trp
```

-continued

```
His Asp Thr Cys Phe Val Cys Ala Ile Cys Gln Ile

Asn 385 390 395 400 Leu Glu Gly Lys Thr Phe Tyr

Ser Lys Lys Asp Arg Pro Leu Cys Lys 405 410 415

Ser His Ala Phe Ser His Val 420
```

This 423 amino acid protein demonstrates 100% homology to the protein shown in SEQ. ID NO. 10, except for the sequence in the highlighted area (amino acids 94-99), which are due to the nucleotide changes depicted above.

The second novel human heart cDNA sequence (SEQ. ID NO: 39) comprises 1575 bp:

```
5 CGACGCAGAG CAGCGCCCTG GCCGGGCCAA GCAGGAGCCG GCATCATGGA TTCCTTCAAG

60 GTAGTGCTGG AGGGGCCAGC ACCTTGGGGC TTCCGGCTGC AAGGGGGCAA GGACTTCAAT

120 GTGCCCCTCT CCATTTCCCG GCTCACTCCT GGGGGCAAAG CGGCGCAGGC CGGAGTGGCC

180 GTGGGTGACT GGGTGCTGAG CATCGATGGC GAGAATGCGG GTAGCCTCAC ACACATCGAA

240 GCTCAGAACA AGATCCGGGC CTGCGGGGAG CGCCTCAGCC TGGGCCTCAG CAGGGCCCAG

300 CCGGTTCAGA GCAAACCGCA GAAGGCCTCC GCCCCCGCCG CGGACCCTCC GCGGTACACC

360 TTTGCACCCA GCGTCTCCCT CAACAAGACG GCCCGGCCCT TTGGGGCGCC CCCGCCCGCT

420 GACAGCGCCC CGCAACAGAA TGGGTGCAGA CCCCTGACAA ACAGCCGCTC CGACCGCTGG

480 TCCCAGATGC CAGCAAGCAG CGGCTGATGG AGAACACAGA GGACTGGCGG CCGCGGCCGG

540 GGACAGGCCA GTCGCGTTCC TTCCGCATCC TTGCCCACCT CACAGGCACC GAGTTCATGC

600 AAGACCCGGA TGAGGAGCAC CTGAAGAAAT CAAGCCAGGT GCCCAGGACA GAAGCCCCAG

660 CCCCAGCCTC ATCTACACCC CAGGAGCCCT GGCCTGGCCC TACCGCCCCC AGCCCTACCA

720 GCCGCCCGCC CTGGGCTGTG GACCCTGCGT TTGCCGAGCG CTATGCCCCG GACAAAACGA

780 GCACAGTGCT GACCCGGCAC AGCCAGCCGG CCACGCCCAC GCCGCTGCAG AGCCGCACCT

840 CCATTGTGCA GGCAGCTGCC GGAGGGGTGC CAGGAGGGGG CAGCAACAAC GGCAAGACTC

900 CCGTGTGTCA CCAGTGCCAC AAGGTCATCC GGGGCCGCTA CCTGGTGGCG TTGGGCCACG

960 CGTACCACCC GGAGGAGTTT GTGTGTAGCC AGTGTGGGAA GGTCCTGGAA GAGGGTGGCT

1020 TCTTTGAGGA GAAGGGCGCC ATCTTCTGCC CACCATGCTA TGACGTGCGC TATGCACCCA

1080 GCTGTGCCAA GTGCAAGAAG AAGATTACAG GCGAGATCAT GCACGCCCTG AAGATGACCT

1140 GGCACGTGCA CTGCTTTACC TGTGCTGCCT GCAAGACGCC CATCCGGAAC AGGGCCTTCT

1200 ACATGGAGGA GGGCGTGCCC TATTGCGAGC GAGACTATGA GAAGATGTTT GGCACGAAAT

1260 GCCATGGCTG TGACTTCAAG ATCGACGCTG GGGACCGCTT CCTGGAGGCC CTGGGCTTCA

1320 GCTGGCATGA CACCTGCTTC GTCTGTGCGA TATGTCAGAT CAACCTGGAA GGAAAGACCT

1380 TCTACTCCAA GAAGGACAGG CCTCTCTGCA AGAGCCATGC CTTCTCTCAT GTGTGAGCCC

1440 CTTCTGCCCA CAGCTGCCGC GGTGGCCCCT AGCCTGAGGG GCCTGGAGTC GTGGCCCTGC

1500 ATTTCTGGGT AGGGCTGGCA ATGGTTGCCT TAACCCTGGC TCCTGGCCCG AGCCTGGGCT

1560 CCCGGGCCCT GCCCA

1575
```

Reading frame shifts caused by the addition of a 17 bp fragment (bolded, italicized and underlined) results in an early translation stop codon at position 565-567 (underlined).

The derived amino acid sequence (SEQ. ID NO: 40) consists of 153 amino acids:

```
6 Met Asp Ser Phe Lys Val Val Leu Glu Gly Pro Ala
Pro Trp Gly Phe 1 5 10 15 Arg Leu Gln Gly Gly Lys
Asp Phe Asn Val Pro Leu Ser Ile Ser Arg 20 25 30
Leu Thr Pro Gly Gly Lys Ala Ala Gln Ala Gly Val
Ala Val Gly Asp 35 40 45 Trp Val Leu Ser Ile Asp
Gly Glu Asn Ala Gly Ser Leu Thr His Ile 50 55 60
Glu Ala Gln Asn Lys Ile Arg Ala Cys Gly Glu Arg
Leu Ser Leu Gly 65 70 75 80 Leu Ser Arg Ala Gln
Pro Val Gln Ser Lys Pro Gln Lys Ala Ser Ala 85 90
95 Pro Ala Ala Asp Pro Pro Arg Tyr Thr Phe Ala Pro
Ser Val Ser Leu 100 105 110 Asn Lys Thr Ala Arg
Pro Phe Gly Ala Pro Pro Pro Ala Asp Ser Ala 115
120 125 Pro Gln Gln Asn Gly Cys Arg Pro Leu Thr
Asn Ser Arg Ser Asp Arg 130 135 140 Trp Ser Gln
Met Pro Ala Ser Ser Gly 145 150
```

This protein demonstrates 100% homology to SEQ. ID NO: 10 until amino acid 94, where the addition of the 17 bp fragment depicted in the nucleotide sequence results in a frame shift. Over amino acids 94-153, the protein is not homologous to SEQ. ID NO: 10. Amino acids 154-457 in SEQ. ID NO: 10 are not present due to the early stop codon depicted in nucleotide sequence.

Example 42

Genomic HLMP-1 Nucleotide Sequence

Applicants have identified the genomic DNA sequence encoding HLMP-1, including putative regulatory elements associated with HLMP-1 expression. The entire genomic sequence is shown in SEQ. ID. NO: 41. This sequence was derived from AC023788 (clone RP11-564G9), Genome Sequencing Center, Washington University School of Medicine, St. Louis, Mo.

The putative promoter region for HLMP-1 spans nucleotides 2,660-8,733 in SEQ. ID NO: 41. This region comprises, among other things, at least ten potential glucocorticoid response elements ("GREs") (nucleotides 6148-6153, 6226-6231, 6247-6252, 6336-6341, 6510-6515, 6552-6557, 6727-6732, 6752-6757, 7738-7743, and 8255-8260), twelve potential Sma-2 homologues to Mothers against Drosophilla decapentaplegic ("SMAD") binding element sites (nucleotides 3569-3575, 4552-4558, 4582-4588, 5226-5232, 6228-6234, 6649-6655, 6725-6731, 6930-6936, 7379-7384, 7738-7742, 8073-8079, and 8378-8384), and three TATA boxes (nucleotides 5910-5913, 6932-6935, and 7380-7383). The three TATA boxes, all of the GRES, and eight of the SMAD binding elements ("SBEs") are grouped in the region spanning nucleotides 5,841-8,733 in SEQ. ID NO: 41. These regulatory elements can be used, for example, to regulate expression of exogenous nucleotide sequences encoding proteins involved in the process of bone formation. This would permit systemic administration of therapeutic factors or genes relating to bone formation and repair, as well as factors or genes associated with tissue differentiation and development.

In addition to the putative regulatory elements, 13 exons corresponding to the nucleotide sequence encoding HLMP-1 have been identified. These exons span the following nucleotides in SEQ. ID NO: 41: 7 Exon 1 8733-8767 Exon 2 9790-9895 Exon 3 13635-13787 Exon 4 13877-13907 Exon 5 14387-14502 Exon 6 15161-15297 Exon 7 15401-15437 Exon 8 16483-16545 Exon 9 16689-16923 Exon 10 18068-18248 Exon 11 22117-22240 Exon 12 22323-22440 Exon 13 22575-22911

In HLMP-2 there is another exon (Exon 5A), which spans nucleotides 14887-14904.

Example 43

Expression of HLMP-1 in Intervertebral Disc Cells

LIM mineralization protein-1 (LMP-1) is an intracellular protein that can direct cellular differentiation in osseous and non-osseous tissues. This example demonstrates that expressing human LMP-1 ("HLMP-1") in intervertebral disc cells increases proteoglycan synthesis and promotes a more chondrocytic phenotype. In addition, the effect of HLMP-1 expression on cellular gene expression was demonstrated by measuring Aggrecan and BMP-2 gene expression. Lumbar intervertebral disc cells were harvested from Sprague-Dawley rats by gentle enzymatic digestion and cultured in monolayer in DMEM/F12 supplemented with 10% FBS. These cells were then split into 6 well plates at approximately 200,000 cells per well and cultured for about 6 days until the cells reached approximately 300,000 cells per well. The culture media was changed to 1% FBS DMEM/F12 and this was considered Day 0.

Replication deficient Type 5 adenovirus comprising a HLMP-1 cDNA operably linked to a cytomegalovirus ("CMV") promoter has been previously described, for example, in U.S. Pat. No. 6,300,127. The negative control adenovirus was identical except the HLMP-1 cDNA was replaced by LacZ cDNA. For a positive control, uninfected cultures were incubated in the continuous presence of BMP-2 at a concentration of 100 nanograms/milliliter.

On Day 0, the cultures were infected with adenovirus for 30 minutes at 37° C. in 300 microliters of media containing 1% FBS. Fluorescence Activated Cell Sorter ("FACS") analysis of cells treated with adenovirus containing the green fluorescent protein ("GFP") gene ("AdGFP") was performed to determine the optimal dose range for expression of transgene. The cells were treated with adenovirus containing the human LMP-1 cDNA (AdHLMP-1) (at MOIs of 0, 100, 300, 1000, or 3000) or with adenovirus containing the LacZ marker gene (AdLacZ MOI of 1000) (negative control). The culture media was changed at day 3 and day 6 after infection.

Proteoglycan production was estimated by measuring the sulfated glycosaminoglycans (sGAG) present in the culture media (at day 0, 3, and 6) using a di-methyl-methylene blue ("DMMB") calorimetric assay.

For quantification of Aggrecan and BMP-2 mRNA, cells were harvested at day 6 and the mRNA extracted by the Trizol technique. The mRNA was converted to cDNA using reverse-transcriptase and used for real-time PCR, which allowed the relative abundance of Aggrecan and BMP-2 message to be determined. Real time primers were designed and tested for Aggrecan and BMP-2 in previous experiments. The Cyber-green technique was used. Standardization curves were used to quantitate mRNA abundance.

For transfected cells, cell morphology was documented with a light microscope. Cells became more rounded with AdHLMP-1 (MOI 1000) treatment, but not with AdLacZ treatment. AdLacZ infection did not significantly change cell morphology.

FACS analysis of rat disc cells infected with ADGFP at MOI of 1000 showed the highest percentage of cells infected (45%).

There was a dose dependent increase between sGAG production and AdhLMP-1 MOI. These data are seen in FIG. 1, which shows the production of sGAG after over-expressing HLMP-1 at different MOIs in rat disc cells in monolayer cultures. The results have been normalized to day 0 untreated cells. Error bars represent the standard error of the mean. As shown in FIG. 1, the sGAG production observed at day 3 was relatively minor, indicating a lag time between transfection and cellular production of GAG. Treatment with AdLacZ did not significantly change the sGAG production. As also shown in FIG. 1, the optimal dose of AdhLMP-1 was at a MOI of 1000, resulting in a 260% enhancement of sGAG production over the untreated controls at day 6. Higher or lower doses of AdhLMP-1 lead to a diminished response.

Figure 2:
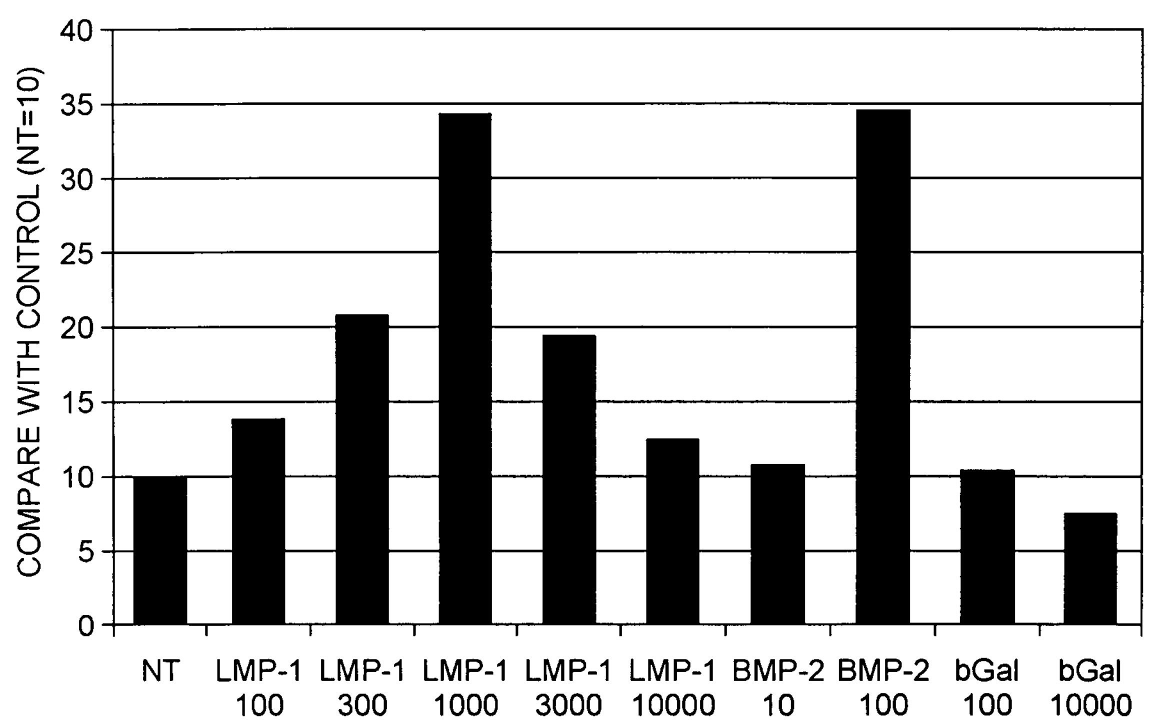
FIG. 2 is a chart showing the dose response of rat intervertebral disc cells six days after infection with different MOI of AdHLMP-1.

The effect of AdhLMP-1 dosage (MOI) on sGAG production is further illustrated in FIG. 2. FIG. 2 is a chart showing rat disc sGAG levels at day 6 after treatment with AdhLMP-1 at different MOIs. As can be seen from FIG. 2, the optimal dose of AdhLMP-1 was at a MOI of 1000.

Figure 3:
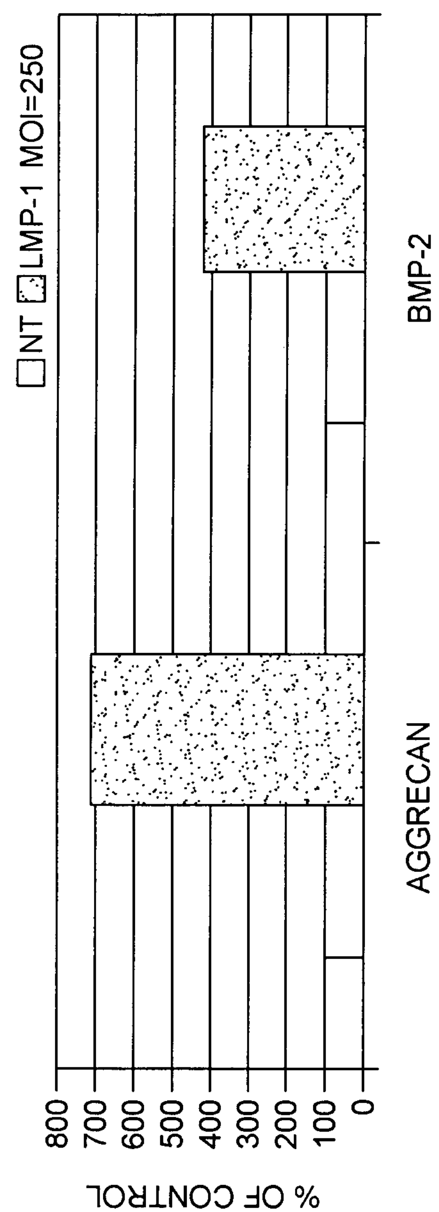
FIG. 3 is a chart showing the expression of Aggrecan and BMP-2 mRNA by AdHLMP-1 transfected rat intervertebral disc cells six days following transfection with an MOI of 250 virions/cell.
Figure 4A:
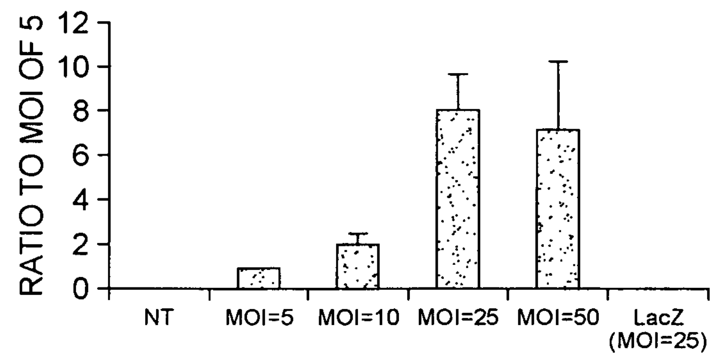
FIG. 4A is a chart showing HLMP-1 mRNA expression 12 hours after infection with Ad-hLMP-1 at different MOIs.
Figure 4B:
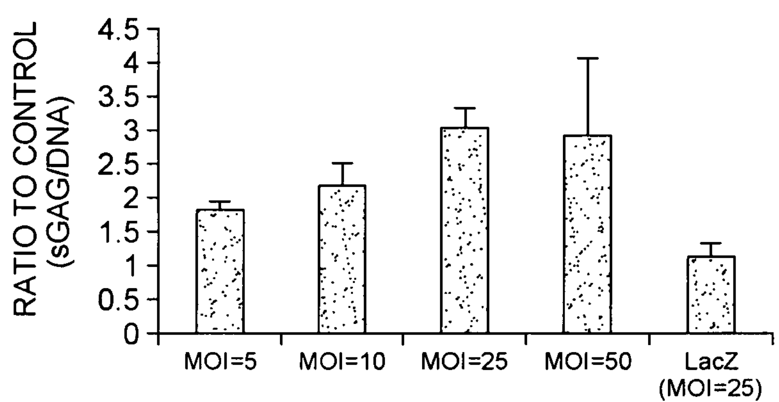
FIG. 4B is a chart showing the production of sGAG in medium from 3 to 6 days after infection. DMMB assay was used to quantitate total sGAG production between days 3 to 6 after infection. The data in FIG. 4B is normalized to the control (i.e., no treatment) group. As can be seen from FIG. 4B, there was a dose dependent increase in sGAG. with the peak of approximately three fold increase above control reached with a MOI of 25 and 50. The negative control, Ad-LacZ at a MOI of 25, lead to no increase in sGAG.
Figure 5:
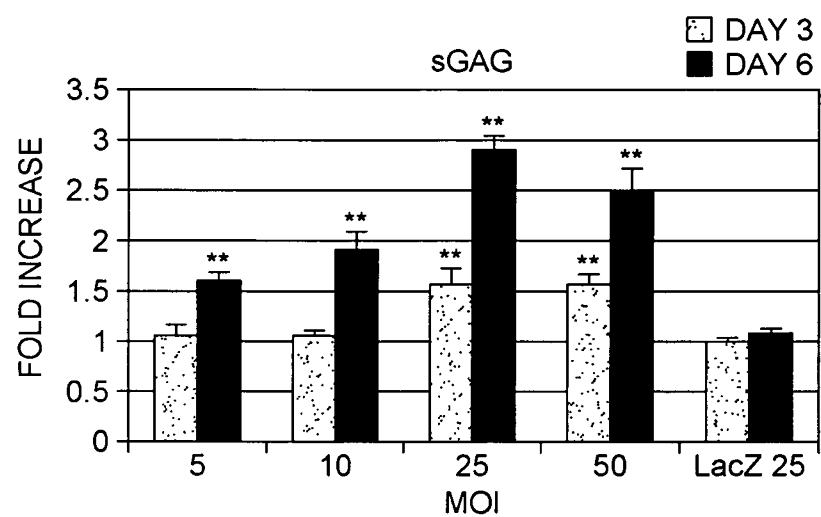
FIG. 5 is a chart showing time course changes of the production of sGAG. As can be seen from FIG. 5, on day 3 sGAG production increased significantly at a MOI of 25 and 50. On day 6 there was a dose dependent increase in sGAG production in response to AdLMP-1. The plateau level of sGAG increase was achieved at a MOI of 25. As can also be seen from FIG. 5, treatment with AdLacZ ("LacZ") did not significantly change the sGAG production. Each result is expressed as mean with SD for six to nine samples.
Figure 6A:
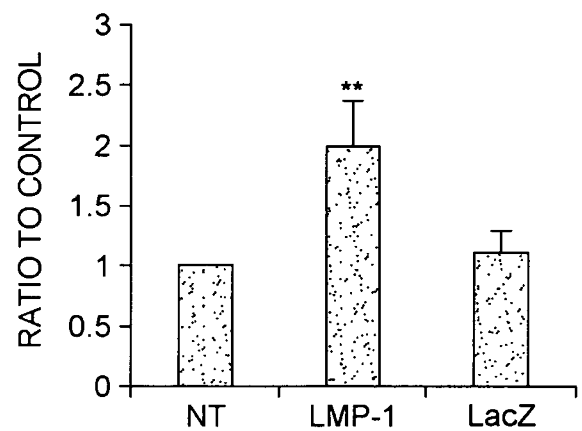
FIGS. 6A and 6B are charts showing gene response to LMP-1 over-expression in rat annulus fibrosus cells for aggrecan and BMP-2, respectively. Quantitative realtime PCR was performed on day 3 after infection with Ad-LMP-1 ("LMP-1") at a MOI of 25. As can be seen from FIGS. 6A and 6B, the gene expression of aggrecan and BMP-2 increased significantly after infection with Ad-LMP-1 compared to the untreated control ("NT"). Further, treatment with AdLacZ ("LacZ") at a MOI of 25 did not significantly change the gene expression of either aggrecan or BMP-2 compared to the untreated control.
Figure 6B:
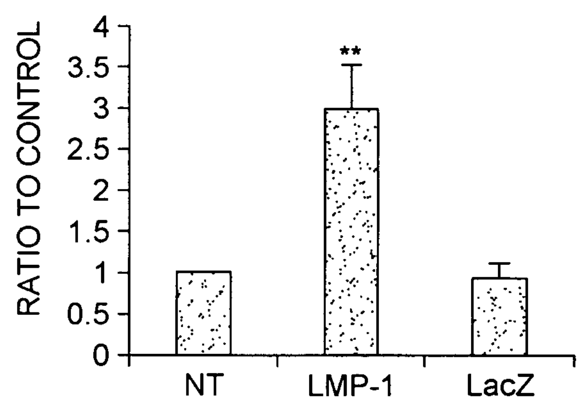
Figure 7:
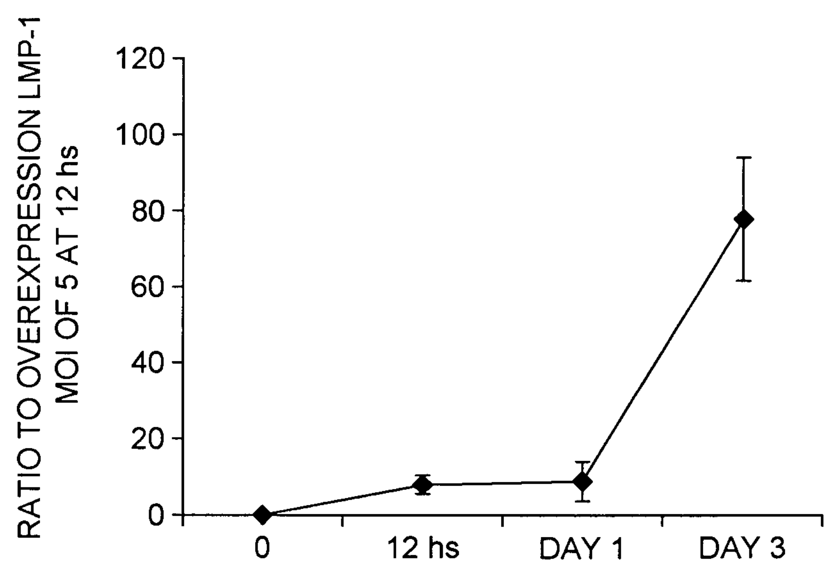
FIG. 7 is a graph showing the time course of HLMP-1 mRNA levels in rat annulus fibrosus cells after infection with AdLMP-1 at a MOI of 25. The data is expressed as a fold increase above a MOI of 5 of AdLMP-1 after standardization using 18S and replication coefficient of over-expression LMP-1 primer. As can be seen from FIG. 7, HLMP-1 mRNA was upregulated significantly as early as 12 hours after infection. Further, there was a marked increase of expression levels between day 1 and day 3. Each result in FIG. 7 is expressed as mean with SD for six samples.
Figure 8:
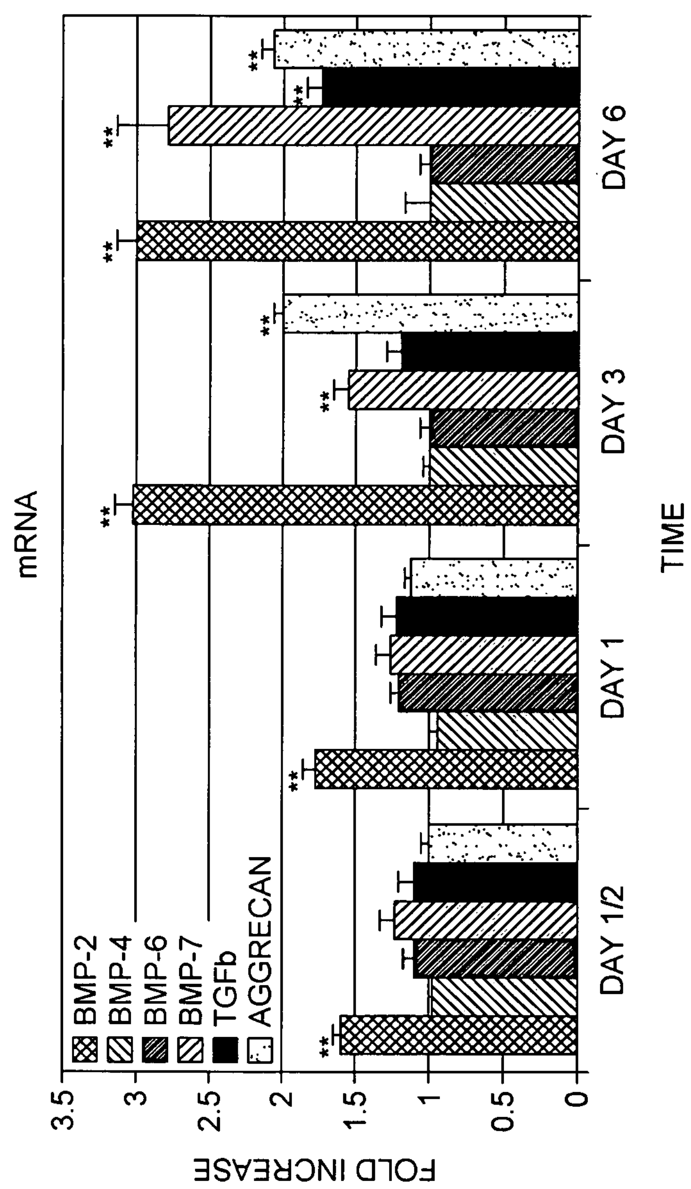
FIG. 8 is a chart showing changes in mRNA levels of BMPs and aggrecan in response to HLMP-1 over-expression. The mRNA levels of BMP-2, BMP-4, BMP-6, BMP7, and aggrecan were determined with realtime-PCR at different time points after infection with Ad-hLMP-1 at a MOI of 25. As can be seen from FIG. 8, BMP-2 mRNA was upregulated significantly as early as 12 hours after infection with AdLMP-1. On the other hand, Aggrecan mRNA was not upregulated until 3 day after infection. Each data point is expressed as mean with SD for six samples.
Figure 9:
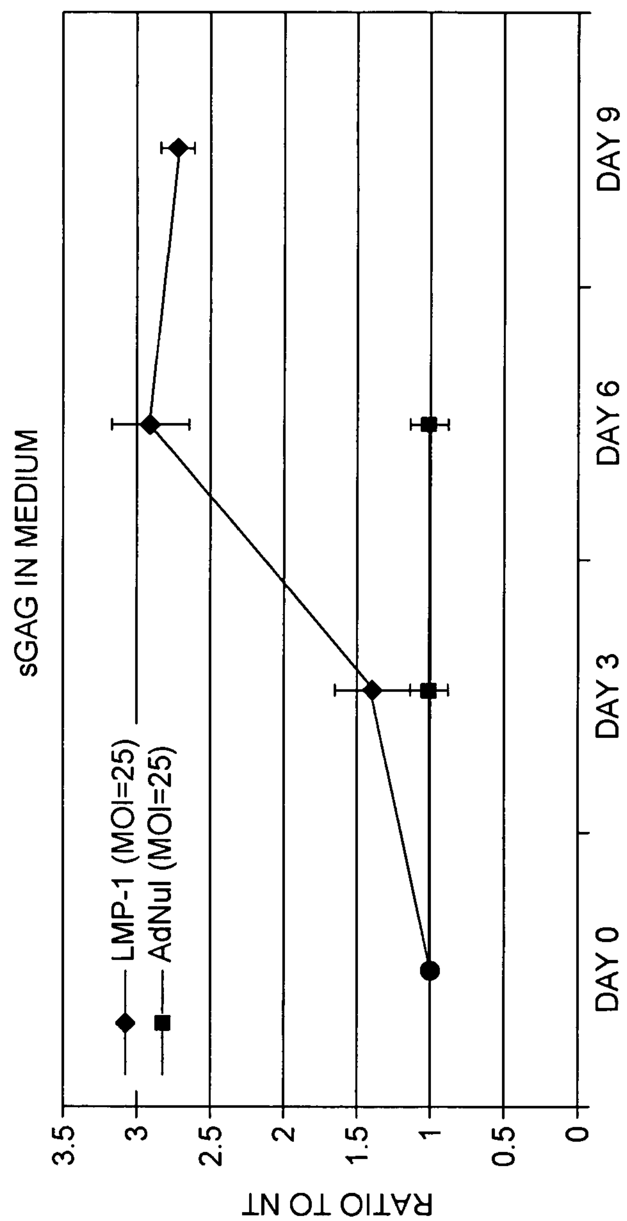
FIG. 9 is a graph showing the time course of sGAG production enhancement in response to HLMP-1 expression. For the data in FIG. 9, rat annulus cells were infected with Ad-hLMP-1 at a MOI of 25. The media was changed every three days after infection and assayed for sGAG with the DMMB assay. This data shows that sGAG production reaches a plateau at day 6 and is substantially maintained at day 9.
Figure 10:
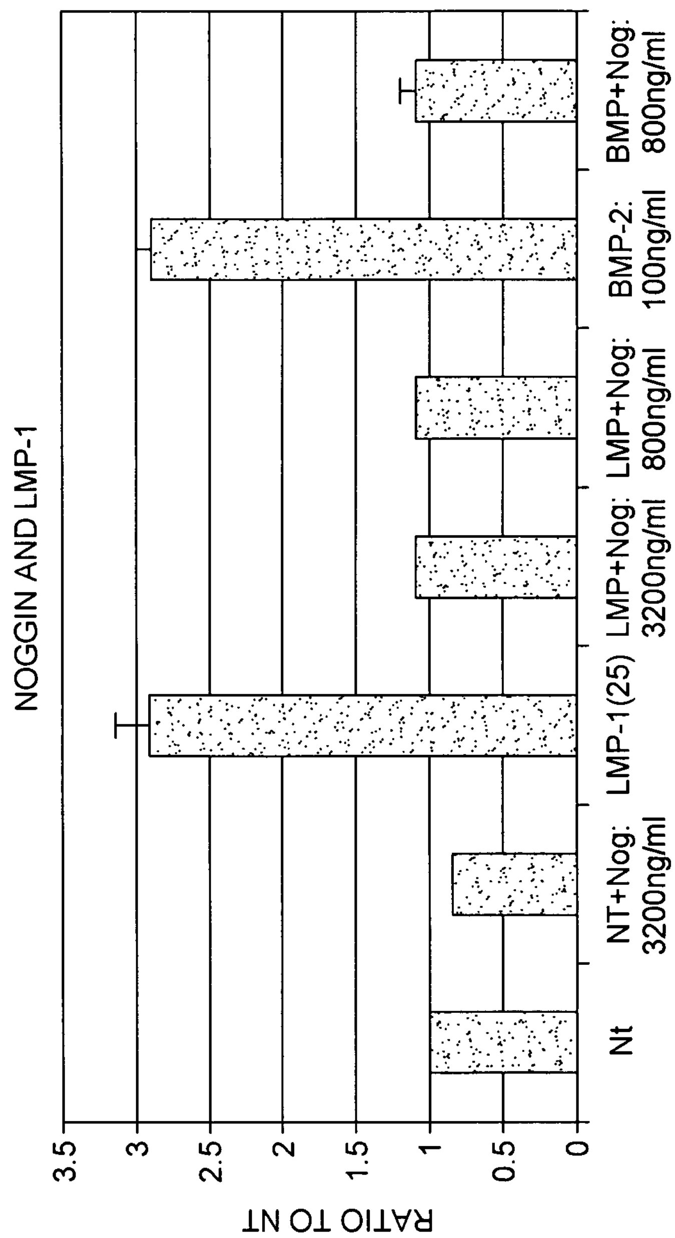
FIG. 10 is a chart showing that the LMP-l mediated increase in sGAG production is blocked by noggin.
Figure 11:
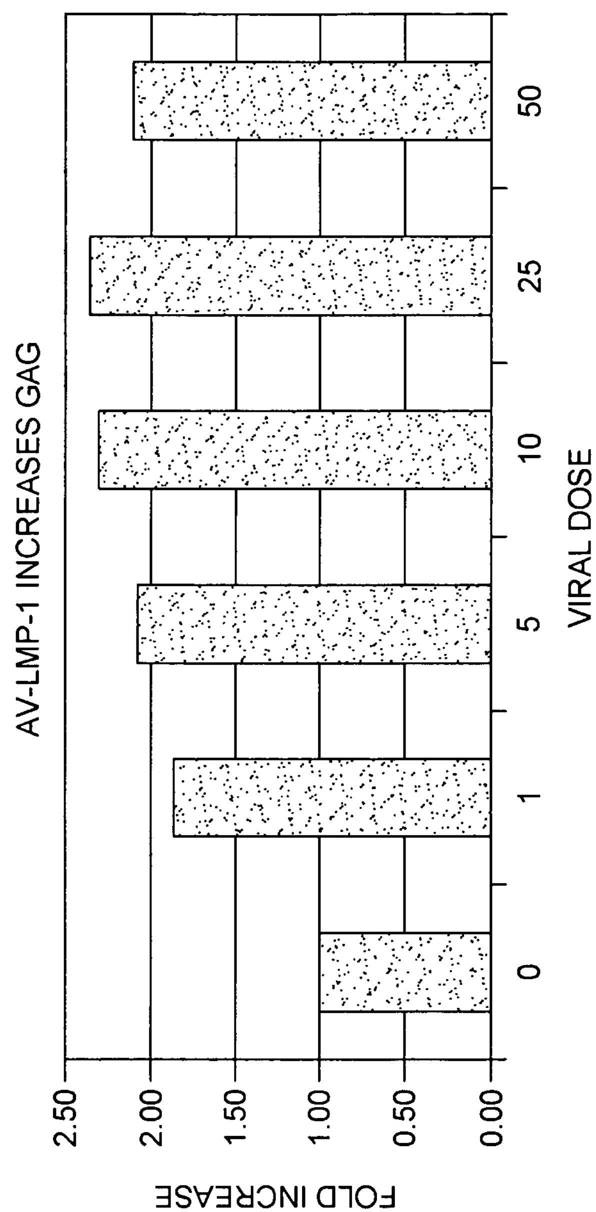
FIG. 11 is a graph showing the effect of LMP-1 on sGAG in media after day 6 of culture in monolayer. The data points are represented as fold increase above untreated cells.

Aggrecan and BMP-2 mRNA production is seen in FIG. 3. This figure demonstrates the increase in Aggrecan and BMP-2 mRNA after over-expression of HLMP-1. Real-time PCR of mRNA extracted from rat disc cells at day 6 was performed comparing the no-treatment ("NT") cells with cells treated with ADhLMP-1 at a MOI of 250. The data in FIG. 3 are represented as a percentage increase over the untreated sample. As illustrated in FIG. 3, a significant increase in Aggrecan and BMP-2 mRNA was noted following AdhLMP-1 treatment. The increase in BMP-2 expression suggests that BMP-2 is a down-stream gene that mediates HLMP-1 stimulation of proteoglycan synthesis.

These data demonstrate that transfection with AdhLMP-1 is effective in increasing proteoglycan synthesis of intervertebral disc cells. The dose of virus leading to the highest transgene expression (MOI 1000) also leads to the highest induction of sGAG, suggesting a correlation between HLMP-1 expression and sGAG induction. These data indicate that HLMP-1 gene therapy is a method of increasing proteoglycan synthesis in the intervertebral disc, and that HLMP-1 is a agent for treating disc disease.

| | |
|---|---|
| Aggrecan (forward) | AGGATGGCTTCCACCAGTGC |
| Aggrecan (reverse) | TGCGTAAAAGACCTCACCCTCC |
| BMP-2 (forward) | CACAAGTCAGTGGGAGAGC |
| BMP-2 (reverse) | GCTTCCGCTGTTTGTGTTTG |
| GAPDH (forward) | ACCACAGTCCATGCCATCAC |
| GAPDH (reverse) | TCCACCACCCTGTTGCTGTA |

GAPDH in Table 2 denotes glyceraldehyde phosphate dehydrogenase.

TABLE 3

Primer and Probe sequences for Real-time PCR of TaqMan ®

| Primer | Sequence |
|---|---|
| Overexpression LMP-1 (forward) | AATACGACTCACTATAGGGCTCGA |
| Overexpression LMP-1 (reverse) | GGAAGCCCCAAGGTGCT |
| Overexpression LMP-1 (probe) | -FAM-AGCCGGCATCATGGATTCCTTCAA-TAMRA |

TaqMan® Ribosomal RNA Control Reagents (Part number 4308329, Applied Biosystems, Foster City, Calif., U.S.A.) were used for the forward primer, reverse primer and probe of 18S ribosomal RNA (rRNA) gene.

All cited publications and patents are hereby incorporated by reference in their entirety.

While the foregoing specification teaches the principles of the present invention, with examples provided for the purpose of illustration, it will be appreciated by one skilled in the art from reading this disclosure that various changes in form and detail can be made without departing from the true scope of the invention.

The invention claimed is:

1. A method of producing a histidine-tagged LIM mineralization protein in a recombinant human host cell, which comprises:

transfecting human host cell with an isolated nucleic acid molecule encoding the histidine-tagged LIM mineralization protein, culturing said cell under conditions promoting the expression of the LIM mineralization protein in said cell; and, purifying the LIM mineralization protein comprising the steps of fractionation by gel filtration prior to metal affinity chromatography, wherein said fractionalization includes:

suspending the LIM mineralization protein in a 20 mM phosphate lysis buffer, the phosphate lysis buffer comprising pH 7.0 containing 50 mM Tris-HCl, pH 7.5 and 5 M NaCL, spinning the LIM mineralization protein in a centrifuge at 10,000 g at 4° C. to produce a supernatant, applying the supernatant onto a gel filtration column preloaded with low and high molecular weight protein markers at a low flow rate, the flow rate comprising 1 ml/minute, and wherein said metal affinity chromatography includes:

applying the at least one fraction onto a metal affinity column, washing non-specific and low affinity proteins from the metal affinity column with a first phosphate buffer, eluting affinity-bound proteins from the metal affinity column with a second phosphate buffer, concentrating the affinity-bound proteins, and dialyzing the concentrated affinity-bound proteins to produce a LIM mineralization protein that is substantially free of any carbohydrate moiety, wherein the method is performed in vitro.

2. The method of claim 1, wherein it further comprise a step of assessing the post-translational modification of the expressed protein.

3. The method of claim 2, wherein the post-translational modification of the expressed protein is post-translational glycosylation.

4. The method of claim 1, wherein the affinity-bound proteins are dialyzed against 20 mM Tris-HCl, pH 7.5 at 4° C.

5. The method of claim 4, wherein the metal affinity column is a Ni++-nitriloacetic acid agarose column.

6. The method of claim 1, wherein the carbohydrate moiety is hexosamines.

7. The method of claim 6, wherein the isolated nucleic acid: hybridizes under standard conditions to a nucleic acid molecule complementary to the full length of SEQ. ID NO: 25; and/or hybridizes under highly stringent conditions to a nucleic acid molecule complementary to the full length of SEQ. ID NO: 26.

8. The method of claim 1, wherein the isolated nucleic acid: hybridizes under standard conditions to a nucleic acid molecule complementary to the full length of SEQ.ID NO: 25; and/or hybridizes under highly stringent conditions to a nucleic acid molecule complementary to the full length of SEQ. ID NO: 26.

9. The method of claim 1, wherein the nucleic acid is in an expression vector.

10. The method of claim 9, wherein the expression vector is a plasmid.

11. The method of claim 9, wherein the vector is a virus.

12. The method of claim 11, wherein the virus is an adenovirus.

13. The method of claim 11, wherein the virus is a retrovirus.

14. The method according to claim 1, wherein the LIM mineralization protein is selected from the group consisting of LMP-1, RLMP, HLMP-1, HLMP-1s, HLMP-2, and HLMP-3.

15. The method according to claim 14, wherein the LIM mineralization protein is HLMP-1 and is transcribed by the isolated nucleic acid which hybridizes under standard conditions to a nucleic acid molecule complementary to the full length of SEQ. ID NO: 25; and/or hybridizes under highly stringent conditions to a nucleic acid molecule complementary to the full length of SEQ. ID NO: 26.

16. A method of assessing the post-translational glycosylation of a histidine-tagged LIM mineralization protein in a human host cell comprising transfecting a human host cell with an isolated nucleic acid molecule encoding the histidine-tagged LIM mineralization protein, culturing the human host cell under conditions promoting the expression of the LIM mineralization protein in said cell; and, purifying the LIM mineralization protein comprising the steps of fractionation by gel filtration prior to metal affinity chromatography, and determining the post-translational glycosylation of the LIM mineralization protein, wherein the LIM mineralization protein is substantially free of any carbohydrate moiety;

wherein said fractionalization includes:

suspending the LIM mineralization protein in a 20 mM phosphate lysis buffer, the phosphate lysis buffer comprising pH 7.0 containing 50 mM Tris-HCl, pH 7.5 and 5 M NaCL, spinning the LIM mineralization protein in a centrifuge at 10,000 g at 4° C. to produce a supernatant, applying the supernatant onto a gel filtration column preloaded with low and high molecular weight protein markers at a low flow rate, the flow rate comprising 1 ml/minute, and wherein said metal affinity chromatography includes:

applying the at least one fraction onto a metal affinity column, washing non-specific and low affinity proteins from the metal affinity column with a first phosphate buffer, eluting affinity-bound proteins from the metal affinity column with a second phosphate buffer, concentrating the affinity-bound proteins, and dialyzing the concentrated affinity-bound proteins to produce a LIM mineralization protein that is substantially free of any carbohydrate moiety, wherein the method is performed in vitro.

17. The method of claim 16, wherein the affinity-bound proteins are dialyzed against 20 mM Tris-HCl, pH 7.5 at 4° C.

18. The method of claim 16, wherein the metal affinity column is a Ni++-nitriloacetic acid agarose column.

19. The method of claim 16, wherein the isolated nucleic acid hybridizes under standard conditions to a nucleic acid molecule complementary to the full length of SEQ. ID NO: 25 and/or hybridizes under highly stringent conditions to a nucleic acid molecule complementary to the full length of SEQ. ID NO: 26.

20. The method of claim 16, wherein the carbohydrate moiety is hexosamines; and wherein the isolated nucleic acid hybridizes under standard conditions to a nucleic acid molecule complementary to the full length of SEQ. ID NO: 25 and/or hybridizes under highly stringent conditions to a nucleic acid molecule complementary to the full length of SEQ. ID NO: 26.

21. The method of claim 20, wherein the nucleic acid molecule is in an expression vector.

22. The method of claim 21, wherein the vector is a virus.

23. The method of claim 22, wherein the virus is an adenovirus.

24. The method of claim 22, wherein the virus is a retrovirus.

25. The method of claim 1, wherein the human host cell is A549 cell.

26. The method of claim 16, wherein the human host cell is A549 cell.

* * * * *

SEQUENCE LISTING

```
<160> NUMBER OF SEQ ID NOS: 74

<210> SEQ ID NO 1
<211> LENGTH: 457
<212> TYPE: PRT
<213> ORGANISM: Rattus norvegicus

<400> SEQUENCE: 1

Met Asp Ser Phe Lys Val Val Leu Glu Gly Pro Ala Pro Trp Gly Phe
  1               5                  10                  15

Arg Leu Gln Gly Gly Lys Asp Phe Asn Val Pro Leu Ser Ile Ser Arg
             20                  25                  30

Leu Thr Pro Gly Gly Lys Ala Ala Gln Ala Gly Val Ala Val Gly Asp
         35                  40                  45

Trp Val Leu Ser Ile Asp Gly Glu Asn Ala Gly Ser Leu Thr His Ile
     50                  55                  60
```

```
Glu Ala Gln Asn Lys Ile Arg Ala Cys Gly Glu Arg Leu Ser Leu Gly
 65                  70                  75                  80

Leu Ser Arg Ala Gln Pro Ala Gln Ser Lys Pro Gln Lys Ala Leu Thr
                 85                  90                  95

Pro Pro Ala Asp Pro Pro Arg Tyr Thr Phe Ala Pro Ser Ala Ser Leu
            100                 105                 110

Asn Lys Thr Ala Arg Pro Phe Gly Ala Pro Pro Pro Thr Asp Ser Ala
        115                 120                 125

Leu Ser Gln Asn Gly Gln Leu Leu Arg Gln Leu Val Pro Asp Ala Ser
    130                 135                 140

Lys Gln Arg Leu Met Glu Asn Thr Glu Asp Trp Arg Pro Arg Pro Gly
145                 150                 155                 160

Thr Gly Gln Ser Arg Ser Phe Arg Ile Leu Ala His Leu Thr Gly Thr
                165                 170                 175

Glu Phe Met Gln Asp Pro Asp Glu Glu Phe Met Lys Lys Ser Ser Gln
            180                 185                 190

Val Pro Arg Thr Glu Ala Pro Ala Pro Ala Ser Thr Ile Pro Gln Glu
        195                 200                 205

Ser Trp Pro Gly Pro Thr Thr Pro Ser Pro Thr Ser Arg Pro Pro Trp
    210                 215                 220

Ala Val Asp Pro Ala Phe Ala Glu Arg Tyr Ala Pro Asp Lys Thr Ser
225                 230                 235                 240

Thr Val Leu Thr Arg His Ser Gln Pro Ala Thr Pro Thr Pro Leu Gln
                245                 250                 255

Asn Arg Thr Ser Ile Val Gln Ala Ala Ala Gly Gly Gly Thr Gly Gly
            260                 265                 270

Gly Ser Asn Asn Gly Lys Thr Pro Val Cys His Gln Cys His Lys Ile
        275                 280                 285

Ile Arg Gly Arg Tyr Leu Val Ala Leu Gly His Ala Tyr His Pro Glu
    290                 295                 300

Glu Phe Val Cys Ser Gln Cys Gly Lys Val Leu Glu Glu Gly Gly Phe
305                 310                 315                 320

Phe Glu Glu Lys Gly Ala Ile Phe Cys Pro Ser Cys Tyr Asp Val Arg
                325                 330                 335

Tyr Ala Pro Ser Cys Ala Lys Cys Lys Lys Lys Ile Thr Gly Glu Ile
            340                 345                 350

Met His Ala Leu Lys Met Thr Trp His Val Pro Cys Phe Thr Cys Ala
        355                 360                 365

Ala Cys Lys Thr Pro Ile Arg Asn Arg Ala Phe Tyr Met Glu Glu Gly
    370                 375                 380

Ala Pro Tyr Cys Glu Arg Asp Tyr Glu Lys Met Phe Gly Thr Lys Cys
385                 390                 395                 400

Arg Gly Cys Asp Phe Lys Ile Asp Ala Gly Asp Arg Phe Leu Glu Ala
                405                 410                 415

Leu Gly Phe Ser Trp His Asp Thr Cys Phe Val Cys Ala Ile Cys Gln
            420                 425                 430

Ile Asn Leu Glu Gly Lys Thr Phe Tyr Ser Lys Lys Asp Lys Pro Leu
        435                 440                 445

Cys Lys Ser His Ala Phe Ser His Val
    450                 455
```

<210> SEQ ID NO 2
<211> LENGTH: 1696
<212> TYPE: DNA

<213> ORGANISM: Rattus norvegicus

<400> SEQUENCE: 2

```
gcacgaggat cccagcgcgg ctcctggagg ccgccaggca gccgcccagc cgggcattca     60

ggagcaggta ccatggattc cttcaaggta gtgctggagg gacctgcccc ttggggcttc    120

cgtctgcaag gggcaagga cttcaacgtg cccctctcca tctctcggct cactcctgga    180

ggcaaggccg cacaggccgg tgtggccgtg ggagactggg tactgagtat cgacggtgag    240

aacgccggaa gcctcacaca cattgaagcc cagaacaaga tccgtgcctg tggggagcgc    300

ctcagcctgg gtcttagcag agcccagcct gctcagagca aaccacagaa ggccctgacc    360

cctcccgccg accccccgag gtacactttt gcaccaagcg cctccctcaa caagacggcc    420

cggcccttcg gggcaccccc acctactgac agcgccctgt cgcagaatgg acagctgctc    480

agacagctgg tccctgatgc cagcaagcag cggctgatgg agaatactga agactggcgc    540

ccgcggccag ggacaggcca gtcccgttcc ttccgcatcc ttgctcacct cacgggcaca    600

gagttcatgc aagacccgga tgaggaattc atgaagaagt caagccaggt gcccaggaca    660

gaagccccag ccccagcctc aaccataccc caggaatcct ggcctggccc caccaccccc    720

agccccacca gccgcccacc ctgggccgta gatcctgcat ttgctgagcg ctatgcccca    780

gacaaaacca gcacagtgct gacccgacac agccagccag ccacacctac gcctctgcag    840

aaccgcacct ccatagttca ggctgcagct ggagggggca caggaggagg cagcaacaat    900

ggcaagacgc ctgtatgcca ccagtgccac aagatcatcc gcggccgata cctggtagca    960

ctgggccacg cgtaccatcc tgaggaattt gtgtgcagcc agtgtgggaa ggtcctggaa   1020

gagggtggct tcttcgagga gaagggagct atcttttgcc cctcctgcta tgatgtgcgc   1080

tatgcaccca gctgtgccaa atgcaagaag aagatcactg gagagatcat gcatgcgctg   1140

aagatgacct ggcatgttcc ctgcttcacc tgtgcagcct gcaaaacccc tatccgcaac   1200

agggctttct acatggagga gggggctccc tactgcgagc gagattacga gaagatgttt   1260

ggcacaaagt gtcgcggctg tgacttcaag atcgatgccg gggaccgttt cctggaagcc   1320

ctgggtttca gctggcatga tacgtgtttt gtttgcgcaa tatgtcaaat caacttggaa   1380

ggaaagacct tctactccaa gaaggacaag cccctgtgca agagccatgc cttttcccac   1440

gtatgagcac ctcctcacac tactgccacc ctactctgcc agaagggtga taaaatgaga   1500

gagctctctc tccctcgacc tttctgggtg gggctggcag ccattgtcct agccttggct   1560

cctggccaga tcctggggct ccctcctcac agtccccttt cccacacttc ctccaccacc   1620

accaccgtca ctcacaggtg ctagcctcct agccccagtt cactctggtg tcacaataaa   1680

cctgtatgta gctgtg                                                   1696
```

<210> SEQ ID NO 3
<211> LENGTH: 260
<212> TYPE: DNA
<213> ORGANISM: Rattus norvegicus

<400> SEQUENCE: 3

```
ttctacatgg aggagggggc tccctactgc gagcgagatt acgagaagat gtttggcaca     60

aagtgtcgcg gctgtgactt caagatcgat gccggggacc gtttcctgga agccctgggt    120

ttcagctggc atgatacgtg ttttgtttgc gcaatatgtc aaatcaactt ggaaggaaag    180

accttctact ccaagaagga caagcccctg tgcaagagcc atgccttttc ccacgtatga    240

gcacctcctc acactactgc                                                260
```

<210> SEQ ID NO 4
<211> LENGTH: 16
<212> TYPE: DNA
<213> ORGANISM: Moloney murine leukemia virus

<400> SEQUENCE: 4
aagctttttt tttttg 16

<210> SEQ ID NO 5
<211> LENGTH: 13
<212> TYPE: DNA
<213> ORGANISM: Moloney murine leukemia virus

<400> SEQUENCE: 5
aagcttggct atg 13

<210> SEQ ID NO 6
<211> LENGTH: 223
<212> TYPE: DNA
<213> ORGANISM: Homo sapiens

<400> SEQUENCE: 6
atccttgctc acctcacggg caccgagttc atgcaagacc cggatgagga gcacctgaag 60
aaatcaagcc aggtgcccag gacagaagcc ccagccccag cctcatctac accccaggag 120
ccctggcctg gccctaccgc cccagccct accagccgcc cgccctgggc tgtggaccct 180
gcgtttgccg agcgctatgc cccagacaaa accagcacag tgc 223

<210> SEQ ID NO 7
<211> LENGTH: 717
<212> TYPE: DNA
<213> ORGANISM: Homo sapiens

<400> SEQUENCE: 7
atggattcct tcaaggtagt gctggagggg ccagcacctt ggggcttccg gctgcaaggg 60
ggcaaggact tcaatgtgcc cctctccatt tcccggctca ctcctggggg caaagcggcg 120
caggccggag tggccgtggg tgactgggtg ctgagcatcg atggcgagaa tgcgggtagc 180
ctcacacaca tcgaagctca gaacaagatc cgggcctgcg gggagcgcct cagcctgggc 240
ctcagcaggg cccagccggt tcagagcaaa ccgcagaagg cctccgcccc cgccgcggac 300
cctccgcggt acacctttgc acccagcgtc tccctcaaca agacggcccg gccctttggg 360
gcgcccccgc ccgctgacag cgccccgcaa cagaatggac agccgctccg accgctggtc 420
ccagatgcca gcaagcagcg gctgatggag aacacagagg actggcggcc gcggccgggg 480
acaggccagt cgcgttcctt ccgcatcctt gcccacctca caggcaccga gttcatgcaa 540
gacccggatg aggagcacct gaagaaatca agccaggtgc ccaggacaga agccccagcc 600
ccagcctcat ctacacccca ggagccctgg cctggcccta ccgcccccag ccctaccagc 660
cgcccgccct gggctgtgga ccctgcgttt gccgagcgct atgccccgga caaaacg 717

<210> SEQ ID NO 8
<211> LENGTH: 1488
<212> TYPE: DNA
<213> ORGANISM: Homo sapiens

<400> SEQUENCE: 8
atcgatggcg agaatgcggg tagcctcaca cacatcgaag ctcagaacaa gatccgggcc 60

```
tgcggggagc gcctcagcct gggcctcagc agggcccagc cggttcagag caaaccgcag    120

aaggcctccg cccccgccgc ggaccctccg cggtacacct ttgcacccag cgtctccctc    180

aacaagacgg cccggccctt tggggcgccc ccgcccgctg acagcgcccc gcaacagaat    240

ggacagccgc tccgaccgct ggtcccagat gccagcaagc agcggctgat ggagaacaca    300

gaggactggc ggccgcggcc ggggacaggc cagtcgcgtt ccttccgcat ccttgcccac    360

ctcacaggca ccgagttcat gcaagacccg gatgaggagc acctgaagaa atcaagccag    420

gtgcccagga cagaagcccc agccccagcc tcatctacac cccaggagcc ctggcctggc    480

cctaccgccc ccagccctac cagccgcccg ccctgagctg tggaccctgc gtttgccgag    540

cgctatgccc cggacaaaac gagcacagtg ctgacccggc acagccagcc ggccacgccc    600

acgccgctgc agagccgcac ctccattgtg caggcagctg ccggaggggt gccaggaggg    660

ggcagcaaca acggcaagac tcccgtgtgt caccagtgcc acaaggtcat ccggggccgc    720

tacctggtgg cgttgggcca cgcgtaccac ccggaggagt ttgtgtgtag ccagtgtggg    780

aaggtcctgg aagagggtgg cttctttgag gagaagggcg ccatcttctg cccaccatgc    840

tatgacgtgc gctatgcacc cagctgtgcc aagtgcaaga agaagattac aggcgagatc    900

atgcacgccc tgaagatgac ctggcacgtg cactgcttta cctgtgctgc ctgcaagacg    960

cccatccgga acagggcctt ctacatggag gagggcgtgc cctattgcga gcgagactat   1020

gagaagatgt ttggcacgaa atgccatggc tgtgacttca agatcgacgc tggggaccgc   1080

ttcctggagg ccctgggctt cagctggcat gacacctgct tcgtctgtgc gatatgtcag   1140

atcaacctgg aaggaaagac cttctactcc aagaaggaca ggcctctctg caagagccat   1200

gccttctctc atgtgtgagc cccttctgcc cacagctgcc gcggtggccc ctagcctgag   1260

gggcctggag tcgtggccct gcatttctgg gtagggctgg caatggttgc cttaaccctg   1320

gctcctggcc cgagcctggg ctcccgggcc cctgcccacc caccttatcc tcccacccca   1380

ctccctccac caccacagca caccggtgct ggccacacca gccccctttc acctccagtg   1440

ccacaataaa cctgtaccca gctgaattcc aaaaaatcca aaaaaaaa                1488


<210> SEQ ID NO 9
<211> LENGTH: 1644
<212> TYPE: DNA
<213> ORGANISM: Homo sapiens

<400> SEQUENCE: 9

atggattcct tcaaggtagt gctggagggg ccagcacctt ggggcttccg gctgcaaggg     60

ggcaaggact tcaatgtgcc cctctccatt tcccggctca ctcctggggg caaagcggcg    120

caggccggag tggccgtggg tgactgggtg ctgagcatcg atggcgagaa tgcgggtagc    180

ctcacacaca tcgaagctca gaacaagatc cgggcctgcg gggagcgcct cagcctgggc    240

ctcagcaggg cccagccggt tcagagcaaa ccgcagaagg cctccgcccc cgccgcggac    300

cctccgcggt acacctttgc acccagcgtc tccctcaaca agacggcccg gccctttggg    360

gcgcccccgc ccgctgacag cgccccgcaa cagaatggac agccgctccg accgctggtc    420

ccagatgcca gcaagcagcg gctgatggag aacacagagg actggcggcc gcggccgggg    480

acaggccagt cgcgttcctt ccgcatcctt gcccacctca caggcaccga gttcatgcaa    540

gacccggatg aggagcacct gaagaaatca agccaggtgc ccaggacaga agccccagcc    600

ccagcctcat ctacacccca ggagccctgg cctggcccta ccgcccccag ccctaccagc    660

cgcccgccct gggctgtgga ccctgcgttt gccgagcgct atgccccgga caaaacgagc    720
```

```
acagtgctga cccggcacag ccagccggcc acgcccacgc cgctgcagag ccgcacctcc    780

attgtgcagg cagctgccgg aggggtgcca ggagggggca gcaacaacgg caagactccc    840

gtgtgtcacc agtgccacaa ggtcatccgg ggccgctacc tggtggcgtt gggccacgcg    900

taccacccgg aggagtttgt gtgtagccag tgtgggaagg tcctggaaga gggtggcttc    960

tttgaggaga agggcgccat cttctgccca ccatgctatg acgtgcgcta tgcacccagc   1020

tgtgccaagt gcaagaagaa gattacaggc gagatcatgc acgccctgaa gatgacctgg   1080

cacgtgcact gctttacctg tgctgcctgc aagacgccca tccggaacag ggccttctac   1140

atggaggagg gcgtgcccta ttgcgagcga gactatgaga agatgtttgg cacgaaatgc   1200

catggctgtg acttcaagat cgacgctggg gaccgcttcc tggaggccct gggcttcagc   1260

tggcatgaca cctgcttcgt ctgtgcgata tgtcagatca acctggaagg aaagaccttc   1320

tactccaaga aggacaggcc tctctgcaag agccatgcct tctctcatgt gtgagcccct   1380

tctgcccaca gctgccgcgg tggcccctag cctgaggggc ctggagtcgt ggccctgcat   1440

ttctgggtag ggctggcaat ggttgcctta accctggctc ctggcccgag cctgggctcc   1500

cgggcccctg cccacccacc ttatcctccc accccactcc ctccaccacc acagcacacc   1560

ggtgctggcc acaccagccc cctttcacct ccagtgccac aataaacctg tacccagctg   1620

aattccaaaa aatccaaaaa aaaa                                          1644
```

```
<210> SEQ ID NO 10
<211> LENGTH: 457
<212> TYPE: PRT
<213> ORGANISM: Homo sapiens

<400> SEQUENCE: 10

Met Asp Ser Phe Lys Val Val Leu Glu Gly Pro Ala Pro Trp Gly Phe
  1               5                  10                  15

Arg Leu Gln Gly Gly Lys Asp Phe Asn Val Pro Leu Ser Ile Ser Arg
             20                  25                  30

Leu Thr Pro Gly Gly Lys Ala Ala Gln Ala Gly Val Ala Val Gly Asp
         35                  40                  45

Trp Val Leu Ser Ile Asp Gly Glu Asn Ala Gly Ser Leu Thr His Ile
     50                  55                  60

Glu Ala Gln Asn Lys Ile Arg Ala Cys Gly Glu Arg Leu Ser Leu Gly
 65                  70                  75                  80

Leu Ser Arg Ala Gln Pro Val Gln Ser Lys Pro Gln Lys Ala Ser Ala
                 85                  90                  95

Pro Ala Ala Asp Pro Pro Arg Tyr Thr Phe Ala Pro Ser Val Ser Leu
            100                 105                 110

Asn Lys Thr Ala Arg Pro Phe Gly Ala Pro Pro Pro Ala Asp Ser Ala
        115                 120                 125

Pro Gln Gln Asn Gly Gln Pro Leu Arg Pro Leu Val Pro Asp Ala Ser
    130                 135                 140

Lys Gln Arg Leu Met Glu Asn Thr Glu Asp Trp Arg Pro Arg Pro Gly
145                 150                 155                 160

Thr Gly Gln Ser Arg Ser Phe Arg Ile Leu Ala His Leu Thr Gly Thr
                165                 170                 175

Glu Phe Met Gln Asp Pro Asp Glu Glu His Leu Lys Lys Ser Ser Gln
            180                 185                 190

Val Pro Arg Thr Glu Ala Pro Ala Pro Ala Ser Ser Thr Pro Gln Glu
        195                 200                 205
```

```
Pro Trp Pro Gly Pro Thr Ala Pro Ser Pro Thr Ser Arg Pro Pro Trp
    210                 215                 220

Ala Val Asp Pro Ala Phe Ala Glu Arg Tyr Ala Pro Asp Lys Thr Ser
225                 230                 235                 240

Thr Val Leu Thr Arg His Ser Gln Pro Ala Thr Pro Thr Pro Leu Gln
                245                 250                 255

Ser Arg Thr Ser Ile Val Gln Ala Ala Ala Gly Gly Val Pro Gly Gly
            260                 265                 270

Gly Ser Asn Asn Gly Lys Thr Pro Val Cys His Gln Cys His Lys Val
        275                 280                 285

Ile Arg Gly Arg Tyr Leu Val Ala Leu Gly His Ala Tyr His Pro Glu
    290                 295                 300

Glu Phe Val Cys Ser Gln Cys Gly Lys Val Leu Glu Glu Gly Gly Phe
305                 310                 315                 320

Phe Glu Glu Lys Gly Ala Ile Phe Cys Pro Pro Cys Tyr Asp Val Arg
                325                 330                 335

Tyr Ala Pro Ser Cys Ala Lys Cys Lys Lys Lys Ile Thr Gly Glu Ile
            340                 345                 350

Met His Ala Leu Lys Met Thr Trp His Val His Cys Phe Thr Cys Ala
        355                 360                 365

Ala Cys Lys Thr Pro Ile Arg Asn Arg Ala Phe Tyr Met Glu Glu Gly
    370                 375                 380

Val Pro Tyr Cys Glu Arg Asp Tyr Glu Lys Met Phe Gly Thr Lys Cys
385                 390                 395                 400

His Gly Cys Asp Phe Lys Ile Asp Ala Gly Asp Arg Phe Leu Glu Ala
                405                 410                 415

Leu Gly Phe Ser Trp His Asp Thr Cys Phe Val Cys Ala Ile Cys Gln
            420                 425                 430

Ile Asn Leu Glu Gly Lys Thr Phe Tyr Ser Lys Lys Asp Arg Pro Leu
        435                 440                 445

Cys Lys Ser His Ala Phe Ser His Val
    450                 455
```

<210> SEQ ID NO 11
<211> LENGTH: 22
<212> TYPE: DNA
<213> ORGANISM: Rattus norvegicus

<400> SEQUENCE: 11
gccagggttt tcccagtcac ga 22

<210> SEQ ID NO 12
<211> LENGTH: 22
<212> TYPE: DNA
<213> ORGANISM: Rattus norvegicus

<400> SEQUENCE: 12
gccagggttt tcccagtcac ga 22

<210> SEQ ID NO 13
<211> LENGTH: 22
<212> TYPE: DNA
<213> ORGANISM: Homo sapiens

<400> SEQUENCE: 13
tcttagcaga gcccagcctg ct 22

<210> SEQ ID NO 14
<211> LENGTH: 22
<212> TYPE: DNA
<213> ORGANISM: Homo sapiens

<400> SEQUENCE: 14
gcatgaactc tgtgcccgtg ag 22

<210> SEQ ID NO 15
<211> LENGTH: 20
<212> TYPE: DNA
<213> ORGANISM: Rattus norvegicus

<400> SEQUENCE: 15
atccttgctc acctcacggg 20

<210> SEQ ID NO 16
<211> LENGTH: 22
<212> TYPE: DNA
<213> ORGANISM: Rattus norvegicus

<400> SEQUENCE: 16
gcactgtgct ggttttgtct gg 22

<210> SEQ ID NO 17
<211> LENGTH: 23
<212> TYPE: DNA
<213> ORGANISM: Homo sapiens

<400> SEQUENCE: 17
catggattcc ttcaaggtag tgc 23

<210> SEQ ID NO 18
<211> LENGTH: 20
<212> TYPE: DNA
<213> ORGANISM: Homo sapiens

<400> SEQUENCE: 18
gttttgtctg gggcagagcg 20

<210> SEQ ID NO 19
<211> LENGTH: 44
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 19
ctaatacgac tcactatagg gctcgagcgg ccgcccgggc aggt 44

<210> SEQ ID NO 20
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 20
ccatcctaat acgactcact atagggc 27

<210> SEQ ID NO 21
<211> LENGTH: 765

```
<212> TYPE: DNA
<213> ORGANISM: Homo sapiens

<400> SEQUENCE: 21

ccgttgtttg taaaacgacg cagagcagcg ccctggccgg gccaagcagg agccggcatc      60

atggattcct tcaaggtagt gctggagggg ccagcacctt ggggcttccg gctgcaaggg     120

ggcaaggact tcaatgtgcc ctcctccatt tcccggctca cctctggggg caaggccgtg     180

caggccggag tggccgtaag tgactgggtg ctgagcatcg atggcgagaa tgcgggtagc     240

ctcacacaca tcgaagctca gaacaagatc cgggcctgcg gggagcgcct cagcctgggc     300

ctcaacaggg cccagccggt tcagaacaaa ccgcaaaagg cctccgcccc cgccgcggac     360

cctccgcggt acacctttgc accaagcgtc tccctcaaca agacggcccg gcccttgggg     420

gcgcccccgc ccgctgacag cgccccgcag cagaatggac agccgctccg accgctggtc     480

ccagatgcca gcaagcagcg gctgatggag aacacagagg actggcggcc gcggccgggg     540

acaggccagt gccgttcctt tcgcatcctt gctcacctta caggcaccga gttcatgcaa     600

gacccggatg aggagcacct gaagaaatca agccaggtgc ccaggacaga agccccagcc     660

ccagcctcat ctacacccca ggagccctgg cctggcccta ccgcccccag ccctaccagc     720

cgcccgccct gggctgtgga ccctgcgttt gccgagcgct atgcc                     765


<210> SEQ ID NO 22
<211> LENGTH: 1689
<212> TYPE: DNA
<213> ORGANISM: Homo sapiens

<400> SEQUENCE: 22

cgacgcagag cagcgccctg gccgggccaa gcaggagccg gcatcatgga ttccttcaag      60

gtagtgctgg aggggccagc accttggggc ttccggctgc aagggggcaa ggacttcaat     120

gtgcccctct ccatttcccg gctcactcct gggggcaaag cggcgcaggc cggagtggcc     180

gtgggtgact gggtgctgag catcgatggc gagaatgcgg gtagcctcac acacatcgaa     240

gctcagaaca agatccgggc ctgcggggag cgcctcagcc tgggcctcag cagggcccag     300

ccggttcaga gcaaaccgca gaaggcctcc gcccccgccg cggaccctcc gcggtacacc     360

tttgcaccca gcgtctccct caacaagacg gcccggccct tggggcgcc cccgcccgct      420

gacagcgccc cgcaacagaa tggacagccg ctccgaccgc tggtcccaga tgccagcaag     480

cagcggctga tggagaacac agaggactgg cggccgcggc cggggacagg ccagtcgcgt     540

tccttccgca tccttgccca cctcacaggc accgagttca tgcaagaccc ggatgaggag     600

cacctgaaga aatcaagcca ggtgcccagg acagaagccc cagccccagc ctcatctaca     660

ccccaggagc cctggcctgg ccctaccgcc cccagcccta ccagccgccc gccctgggct     720

gtggaccctg cgtttgccga gcgctatgcc ccggacaaaa cgagcacagt gctgacccgg     780

cacagccagc cggccacgcc cacgccgctg cagagccgca cctccattgt gcaggcagct     840

gccggagggg tgccaggagg gggcagcaac aacggcaaga ctcccgtgtg tcaccagtgc     900

cacaaggtca tccggggccg ctacctggtg gcgttgggcc acgcgtacca cccggaggag     960

tttgtgtgta gccagtgtgg gaaggtcctg gaagagggtg gcttctttga ggagaagggc    1020

gccatcttct gcccaccatg ctatgacgtg cgctatgcac ccagctgtgc caagtgcaag    1080

aagaagatta caggcgagat catgcacgcc ctgaagatga cctggcacgt gcactgcttt    1140

acctgtgctg cctgcaagac gcccatccgg aacagggcct tctacatgga ggagggcgtg    1200
```

```
ccctattgcg agcgagacta tgagaagatg tttggcacga aatgccatgg ctgtgacttc   1260

aagatcgacg ctggggaccg cttcctggag gccctgggct tcagctggca tgacacctgc   1320

ttcgtctgtg cgatatgtca gatcaacctg gaaggaaaga ccttctactc caagaaggac   1380

aggcctctct gcaagagcca tgccttctct catgtgtgag ccccttctgc ccacagctgc   1440

cgcggtggcc cctagcctga ggggcctgga gtcgtggccc tgcatttctg ggtagggctg   1500

gcaatggttg ccttaaccct ggctcctggc ccgagcctgg gctcccgggc ccctgcccac   1560

ccaccttatc ctcccacccc actccctcca ccaccacagc acaccggtgc tggccacacc   1620

agccccccttt cacctccagt gccacaataa acctgtaccc agctgaattc caaaaaatcc   1680

aaaaaaaaa                                                            1689


<210> SEQ ID NO 23
<211> LENGTH: 22
<212> TYPE: DNA
<213> ORGANISM: Homo sapiens

<400> SEQUENCE: 23

gcactgtgct cgttttgtcc gg                                               22


<210> SEQ ID NO 24
<211> LENGTH: 21
<212> TYPE: DNA
<213> ORGANISM: Homo sapiens

<400> SEQUENCE: 24

tccttgctca cctcacgggc a                                                21


<210> SEQ ID NO 25
<211> LENGTH: 30
<212> TYPE: DNA
<213> ORGANISM: Homo sapiens

<400> SEQUENCE: 25

tcctcatccg ggtcttgcat gaactcggtg                                       30


<210> SEQ ID NO 26
<211> LENGTH: 28
<212> TYPE: DNA
<213> ORGANISM: Homo sapiens

<400> SEQUENCE: 26

gcccccgccc gctgacagcg ccccgcaa                                         28


<210> SEQ ID NO 27
<211> LENGTH: 24
<212> TYPE: DNA
<213> ORGANISM: Homo sapiens

<400> SEQUENCE: 27

tccttgctca cctcacgggc accg                                             24


<210> SEQ ID NO 28
<211> LENGTH: 22
<212> TYPE: DNA
<213> ORGANISM: Homo sapiens

<400> SEQUENCE: 28

gtaatacgac tcactatagg gc                                               22
```

<210> SEQ ID NO 29
<211> LENGTH: 23
<212> TYPE: DNA
<213> ORGANISM: Rattus norvegicus

<400> SEQUENCE: 29
gcggctgatg gagaatactg aag 23

<210> SEQ ID NO 30
<211> LENGTH: 23
<212> TYPE: DNA
<213> ORGANISM: Rattus norvegicus

<400> SEQUENCE: 30
atcttgtggc actggtggca tac 23

<210> SEQ ID NO 31
<211> LENGTH: 22
<212> TYPE: DNA
<213> ORGANISM: Rattus norvegicus

<400> SEQUENCE: 31
tgtgtcgggt cagcactgtg ct 22

<210> SEQ ID NO 32
<211> LENGTH: 1620
<212> TYPE: DNA
<213> ORGANISM: Homo sapiens

<400> SEQUENCE: 32
atggattcct tcaaggtagt gctggagggg ccagcacctt ggggcttccg gctgcaaggg 60
ggcaaggact tcaatgtgcc cctctccatt tcccggctca ctcctggggg caaagcggcg 120
caggccggag tggccgtggg tgactgggtg ctgagcatcg atggcgagaa tgcgggtagc 180
ctcacacaca tcgaagctca gaacaagatc cgggcctgcg gggagcgcct cagcctgggc 240
ctcagcaggg cccagccggt tcagagcaaa ccgcagaagg cctccgcccc cgccgcggac 300
cctccgcggt acacctttgc acccagcgtc tccctcaaca agacggcccg gccctttggg 360
gcgcccccgc ccgctgacag cgccccgcaa cagaatggac agccgctccg accgctggtc 420
ccagatgcca gcaagcagcg gctgatggag aacacagagg actggcggcc gcggccgggg 480
acaggccagt cgcgttcctt ccgcatcctt gcccacctca caggcaccga gttcatgcaa 540
gacccggatg aggagcacct gaagaaatca agccaggtgc ccaggacaga agccccagcc 600
ccagcctcat ctacacccca ggagccctgg cctggcccta ccgcccccag ccctaccagc 660
cgcccgccct gagctgtgga ccctgcgttt gccgagcgct atgccccgga caaaacgagc 720
acagtgctga cccggcacag ccagccggcc acgcccacgc cgctgcagag ccgcacctcc 780
attgtgcagg cagctgccgg aggggtgcca ggagggggca gcaacaacgg caagactccc 840
gtgtgtcacc agtgccacaa ggtcatccgg ggccgctacc tggtggcgtt gggccacgcg 900
taccacccgg aggagtttgt gtgtagccag tgtgggaagg tcctggaaga gggtggcttc 960
tttgaggaga agggcgccat cttctgccca ccatgctatg acgtgcgcta tgcacccagc 1020
tgtgccaagt gcaagaagaa gattacaggc gagatcatgc acgccctgaa gatgacctgg 1080
cacgtgcact gctttacctg tgctgcctgc aagacgccca tccggaacag ggccttctac 1140
atggaggagg gcgtgcccta ttgcgagcga gactatgaga agatgtttgg cacgaaatgc 1200
catggctgtg acttcaagat cgacgctggg gaccgcttcc tggaggccct gggcttcagc 1260

```
tggcatgaca cctgcttcgt ctgtgcgata tgtcagatca acctggaagg aaagaccttc   1320

tactccaaga aggacaggcc tctctgcaag agccatgcct tctctcatgt gtgagcccct   1380

tctgcccaca gctgccgcgg tggcccctag cctgaggggc ctggagtcgt ggccctgcat   1440

ttctgggtag ggctggcaat ggttgcctta accctggctc ctggcccgag cctgggctcc   1500

cgggcccctg cccacccacc ttatcctccc accccactcc ctccaccacc acagcacacc   1560

ggtgctggcc acaccagccc cctttcacct ccagtgccac aataaacctg tacccagctg   1620
```

<210> SEQ ID NO 33
<211> LENGTH: 1665
<212> TYPE: DNA
<213> ORGANISM: Homo sapiens

<400> SEQUENCE: 33

```
cgacgcagag cagcgccctg gccgggccaa gcaggagccg gcatcatgga ttccttcaag     60

gtagtgctgg aggggccagc accttggggc ttccggctgc aagggggcaa ggacttcaat    120

gtgcccctct ccatttcccg gctcactcct gggggcaaag cggcgcaggc cggagtggcc    180

gtgggtgact gggtgctgag catcgatggc gagaatgcgg gtagcctcac acacatcgaa    240

gctcagaaca agatccgggc ctgcggggag cgcctcagcc tgggcctcag cagggcccag    300

ccggttcaga gcaaaccgca gaaggcctcc gcccccgccg cggaccctcc gcggtacacc    360

tttgcaccca gcgtctccct caacaagacg gcccggccct ttggggcgcc cccgcccgct    420

gacagcgccc cgcaacagaa tggacagccg ctccgaccgc tggtcccaga tgccagcaag    480

cagcggctga tggagaacac agaggactgg cggccgcggc cggggacagg ccagtcgcgt    540

tccttccgca tccttgccca cctcacaggc accgagttca tgcaagaccc ggatgaggag    600

cacctgaaga aatcaagcca ggtgcccagg acagaagccc cagccccagc ctcatctaca    660

ccccaggagc cctggcctgg ccctaccgcc cccagcccta ccagccgccc gccctgagct    720

gtggaccctg cgtttgccga gcgctatgcc ccggacaaaa cgagcacagt gctgacccgg    780

cacagccagc cggccacgcc cacgccgctg cagagccgca cctccattgt gcaggcagct    840

gccggagggg tgccaggagg gggcagcaac aacggcaaga ctcccgtgtg tcaccagtgc    900

cacaaggtca tccggggccg ctacctggtg gcgttgggcc acgcgtacca cccggaggag    960

tttgtgtgta gccagtgtgg gaaggtcctg gaagagggtg gcttctttga ggagaagggc   1020

gccatcttct gcccaccatg ctatgacgtg cgctatgcac ccagctgtgc caagtgcaag   1080

aagaagatta caggcgagat catgcacgcc ctgaagatga cctggcacgt gcactgcttt   1140

acctgtgctg cctgcaagac gcccatccgg aacagggcct tctacatgga ggagggcgtg   1200

ccctattgcg agcgagacta tgagaagatg tttggcacga aatgccatgg ctgtgacttc   1260

aagatcgacg ctggggaccg cttcctggag gccctgggct tcagctggca tgacacctgc   1320

ttcgtctgtg cgatatgtca gatcaacctg gaaggaaaga ccttctactc caagaaggac   1380

aggcctctct gcaagagcca tgccttctct catgtgtgag ccccttctgc ccacagctgc   1440

cgcggtggcc cctagcctga ggggcctgga gtcgtggccc tgcatttctg ggtagggctg   1500

gcaatggttg ccttaaccct ggctcctggc ccgagcctgg gctcccgggc ccctgcccac   1560

ccaccttatc ctcccacccc actccctcca ccaccacagc acaccggtgc tggccacacc   1620

agcccccttt cacctccagt gccacaataa acctgtaccc agctg                  1665
```

<210> SEQ ID NO 34
<211> LENGTH: 223

<212> TYPE: PRT
<213> ORGANISM: Homo sapiens

<400> SEQUENCE: 34

```
Met Asp Ser Phe Lys Val Val Leu Glu Gly Pro Ala Pro Trp Gly Phe
  1               5                  10                  15

Arg Leu Gln Gly Gly Lys Asp Phe Asn Val Pro Leu Ser Ile Ser Arg
             20                  25                  30

Leu Thr Pro Gly Gly Lys Ala Ala Gln Ala Gly Val Ala Val Gly Asp
         35                  40                  45

Trp Val Leu Ser Ile Asp Gly Glu Asn Ala Gly Ser Leu Thr His Ile
     50                  55                  60

Glu Ala Gln Asn Lys Ile Arg Ala Cys Gly Glu Arg Leu Ser Leu Gly
 65                  70                  75                  80

Leu Ser Arg Ala Gln Pro Val Gln Ser Lys Pro Gln Lys Ala Ser Ala
                 85                  90                  95

Pro Ala Ala Asp Pro Pro Arg Tyr Thr Phe Ala Pro Ser Val Ser Leu
            100                 105                 110

Asn Lys Thr Ala Arg Pro Phe Gly Ala Pro Pro Pro Ala Asp Ser Ala
        115                 120                 125

Pro Gln Gln Asn Gly Gln Pro Leu Arg Pro Leu Val Pro Asp Ala Ser
    130                 135                 140

Lys Gln Arg Leu Met Glu Asn Thr Glu Asp Trp Arg Pro Arg Pro Gly
145                 150                 155                 160

Thr Gly Gln Ser Arg Ser Phe Arg Ile Leu Ala His Leu Thr Gly Thr
                165                 170                 175

Glu Phe Met Gln Asp Pro Asp Glu Glu His Leu Lys Lys Ser Ser Gln
            180                 185                 190

Val Pro Arg Thr Glu Ala Pro Ala Pro Ala Ser Ser Thr Pro Gln Glu
        195                 200                 205

Pro Trp Pro Gly Pro Thr Ala Pro Ser Pro Thr Ser Arg Pro Pro
    210                 215                 220
```

<210> SEQ ID NO 35
<211> LENGTH: 20
<212> TYPE: DNA
<213> ORGANISM: Homo sapiens

<400> SEQUENCE: 35

```
gagccggcat catggattcc                                                   20
```

<210> SEQ ID NO 36
<211> LENGTH: 20
<212> TYPE: DNA
<213> ORGANISM: Homo sapiens

<400> SEQUENCE: 36

```
gctgcctgca caatggaggt                                                   20
```

<210> SEQ ID NO 37
<211> LENGTH: 1456
<212> TYPE: DNA
<213> ORGANISM: Homo sapiens

<400> SEQUENCE: 37

```
cgacgcagag cagcgccctg gccgggccaa gcaggagccg gcatcatgga ttccttcaag      60

gtagtgctgg aggggccagc accttggggc ttccggctgc aagggggcaa ggacttcaat     120
```

```
gtgcccctct ccatttcccg gctcactcct gggggcaaag cggcgcaggc cggagtggcc    180

gtgggtgact gggtgctgag catcgatggc gagaatgcgg gtagcctcac acacatcgaa    240

gctcagaaca agatccgggc ctgcggggag cgcctcagcc tgggcctcag cagggcccag    300

ccggttcaga gcaaaccgca gaaggtgcag acccctgaca aacagccgct ccgaccgctg    360

gtcccagatg ccagcaagca gcggctgatg gagaacacag aggactggcg gccgcggccg    420

gggacaggcc agtcgcgttc cttccgcatc cttgcccacc tcacaggcac cgagttcatg    480

caagacccgg atgaggagca cctgaagaaa tcaagccagg tgcccaggac agaagcccca    540

gccccagcct catctacacc ccaggagccc tggcctggcc ctaccgcccc cagccctacc    600

agccgcccgc cctgggctgt ggaccctgcg tttgccgagc gctatgcccc ggacaaaacg    660

agcacagtgc tgacccggca cagccagccg gccacgccca cgccgctgca gagccgcacc    720

tccattgtgc aggcagctgc cggagggggtg ccaggagggg gcagcaacaa cggcaagact    780

cccgtgtgtc accagtgcca caaggtcatc cggggccgct acctggtggc gttgggccac    840

gcgtaccacc cggaggagtt tgtgtgtagc cagtgtggga aggtcctgga agagggtggc    900

ttctttgagg agaagggcgc catcttctgc ccaccatgct atgacgtgcg ctatgcaccc    960

agctgtgcca agtgcaagaa gaagattaca ggcgagatca tgcacgccct gaagatgacc   1020

tggcacgtgc actgctttac ctgtgctgcc tgcaagacgc ccatccggaa cagggccttc   1080

tacatggagg agggcgtgcc ctattgcgag cgagactatg agaagatgtt tggcacgaaa   1140

tgccatggct gtgacttcaa gatcgacgct ggggaccgct tcctggaggc cctgggcttc   1200

agctggcatg acacctgctt cgtctgtgcg atatgtcaga tcaacctgga aggaaagacc   1260

ttctactcca agaaggacag gcctctctgc aagagccatg ccttctctca tgtgtgagcc   1320

ccttctgccc acagctgccg cggtggcccc tagcctgagg ggcctggagt cgtggccctg   1380

catttctggg tagggctggc aatggttgcc ttaaccctgg ctcctggccc gagcctgggc   1440

tcccgggccc tgccca                                                     1456
```

<210> SEQ ID NO 38
<211> LENGTH: 423
<212> TYPE: PRT
<213> ORGANISM: Homo sapiens

<400> SEQUENCE: 38

```
Met Asp Ser Phe Lys Val Val Leu Glu Gly Pro Ala Pro Trp Gly Phe
  1               5                  10                  15

Arg Leu Gln Gly Gly Lys Asp Phe Asn Val Pro Leu Ser Ile Ser Arg
             20                  25                  30

Leu Thr Pro Gly Gly Lys Ala Ala Gln Ala Gly Val Ala Val Gly Asp
         35                  40                  45

Trp Val Leu Ser Ile Asp Gly Glu Asn Ala Gly Ser Leu Thr His Ile
     50                  55                  60

Glu Ala Gln Asn Lys Ile Arg Ala Cys Gly Glu Arg Leu Ser Leu Gly
 65                  70                  75                  80

Leu Ser Arg Ala Gln Pro Val Gln Asn Lys Pro Gln Lys Val Gln Thr
                 85                  90                  95

Pro Asp Lys Gln Pro Leu Arg Pro Leu Val Pro Asp Ala Ser Lys Gln
            100                 105                 110

Arg Leu Met Glu Asn Thr Glu Asp Trp Arg Pro Arg Pro Gly Thr Gly
        115                 120                 125

Gln Ser Arg Ser Phe Arg Ile Leu Ala His Leu Thr Gly Thr Glu Phe
```

```
    130                 135                 140

Met Gln Asp Pro Asp Glu Glu His Leu Lys Lys Ser Ser Gln Val Pro
145                 150                 155                 160

Arg Thr Glu Ala Pro Ala Pro Ala Ser Ser Thr Pro Gln Glu Pro Trp
                165                 170                 175

Pro Gly Pro Thr Ala Pro Ser Pro Thr Ser Arg Pro Pro Trp Ala Val
            180                 185                 190

Asp Pro Ala Phe Ala Glu Arg Tyr Ala Pro Asp Lys Thr Ser Thr Val
        195                 200                 205

Leu Thr Arg His Ser Gln Pro Ala Thr Pro Thr Pro Leu Gln Ser Arg
    210                 215                 220

Thr Ser Ile Val Gln Ala Ala Ala Gly Gly Val Pro Gly Gly Gly Ser
225                 230                 235                 240

Asn Asn Gly Lys Thr Pro Val Cys His Gln Cys His Gln Val Ile Arg
                245                 250                 255

Ala Arg Tyr Leu Val Ala Leu Gly His Ala Tyr His Pro Glu Glu Phe
            260                 265                 270

Val Cys Ser Gln Cys Gly Lys Val Leu Glu Glu Gly Gly Phe Phe Glu
        275                 280                 285

Glu Lys Gly Ala Ile Phe Cys Pro Pro Cys Tyr Asp Val Arg Tyr Ala
    290                 295                 300

Pro Ser Cys Ala Lys Cys Lys Lys Lys Ile Thr Gly Glu Ile Met His
305                 310                 315                 320

Ala Leu Lys Met Thr Trp His Val Leu Cys Phe Thr Cys Ala Ala Cys
                325                 330                 335

Lys Thr Pro Ile Arg Asn Arg Ala Phe Tyr Met Glu Glu Gly Val Pro
            340                 345                 350

Tyr Cys Glu Arg Asp Tyr Glu Lys Met Phe Gly Thr Lys Cys Gln Trp
        355                 360                 365

Cys Asp Phe Lys Ile Asp Ala Gly Asp Arg Phe Leu Glu Ala Leu Gly
    370                 375                 380

Phe Ser Trp His Asp Thr Cys Phe Val Cys Ala Ile Cys Gln Ile Asn
385                 390                 395                 400

Leu Glu Gly Lys Thr Phe Tyr Ser Lys Lys Asp Arg Pro Leu Cys Lys
                405                 410                 415

Ser His Ala Phe Ser His Val
            420
```

<210> SEQ ID NO 39
<211> LENGTH: 1575
<212> TYPE: DNA
<213> ORGANISM: Homo sapiens

<400> SEQUENCE: 39

```
cgacgcagag cagcgccctg gccgggccaa gcaggagccg gcatcatgga ttccttcaag     60

gtagtgctgg aggggccagc accttggggc ttccggctgc aagggggcaa ggacttcaat    120

gtgcccctct ccatttcccg gctcactcct gggggcaaag cggcgcaggc cggagtggcc    180

gtgggtgact gggtgctgag catcgatggc gagaatgcgg gtagcctcac acacatcgaa    240

gctcagaaca agatccgggc ctgcggggag cgcctcagcc tgggcctcag cagggcccag    300

ccggttcaga gcaaaccgca gaaggcctcc gcccccgccg cggaccctcc gcggtacacc    360

tttgcaccca gcgtctccct caacaagacg gcccggccct ttggggcgcc cccgcccgct    420

gacagcgccc cgcaacagaa tgggtgcaga cccctgacaa acagccgctc cgaccgctgg    480
```

```
tcccagatgc cagcaagcag cggctgatgg agaacacaga ggactggcgg ccgcggccgg    540

ggacaggcca gtcgcgttcc ttccgcatcc ttgcccacct cacaggcacc gagttcatgc    600

aagacccgga tgaggagcac ctgaagaaat caagccaggt gcccaggaca gaagccccag    660

ccccagcctc atctacaccc caggagccct ggcctggccc taccgccccc agccctacca    720

gccgcccgcc ctgggctgtg gaccctgcgt ttgccgagcg ctatgccccg gacaaaacga    780

gcacagtgct gacccggcac agccagccgg ccacgcccac gccgctgcag agccgcacct    840

ccattgtgca ggcagctgcc ggaggggtgc caggaggggg cagcaacaac ggcaagactc    900

ccgtgtgtca ccagtgccac aaggtcatcc ggggccgcta cctggtggcg ttgggccacg    960

cgtaccaccc ggaggagttt gtgtgtagcc agtgtgggaa ggtcctggaa gagggtggct   1020

tctttgagga gaagggcgcc atcttctgcc caccatgcta tgacgtgcgc tatgcaccca   1080

gctgtgccaa gtgcaagaag aagattacag gcgagatcat gcacgccctg aagatgacct   1140

ggcacgtgca ctgctttacc tgtgctgcct gcaagacgcc catccggaac agggccttct   1200

acatggagga gggcgtgccc tattgcgagc gagactatga gaagatgttt ggcacgaaat   1260

gccatggctg tgacttcaag atcgacgctg gggaccgctt cctggaggcc ctgggcttca   1320

gctggcatga cacctgcttc gtctgtgcga tatgtcagat caacctggaa ggaaagacct   1380

tctactccaa gaaggacagg cctctctgca agagccatgc cttctctcat gtgtgagccc   1440

cttctgccca cagctgccgc ggtggcccct agcctgaggg gcctggagtc gtggccctgc   1500

atttctgggt agggctggca atggttgcct taaccctggc tcctggcccg agcctgggct   1560

cccgggccct gccca                                                    1575
```

<210> SEQ ID NO 40
<211> LENGTH: 153
<212> TYPE: PRT
<213> ORGANISM: Homo sapiens

<400> SEQUENCE: 40

```
Met Asp Ser Phe Lys Val Val Leu Glu Gly Pro Ala Pro Trp Gly Phe
  1               5                  10                  15

Arg Leu Gln Gly Gly Lys Asp Phe Asn Val Pro Leu Ser Ile Ser Arg
             20                  25                  30

Leu Thr Pro Gly Gly Lys Ala Ala Gln Ala Gly Val Ala Val Gly Asp
         35                  40                  45

Trp Val Leu Ser Ile Asp Gly Glu Asn Ala Gly Ser Leu Thr His Ile
     50                  55                  60

Glu Ala Gln Asn Lys Ile Arg Ala Cys Gly Glu Arg Leu Ser Leu Gly
 65                  70                  75                  80

Leu Ser Arg Ala Gln Pro Val Gln Ser Lys Pro Gln Lys Ala Ser Ala
                 85                  90                  95

Pro Ala Ala Asp Pro Pro Arg Tyr Thr Phe Ala Pro Ser Val Ser Leu
            100                 105                 110

Asn Lys Thr Ala Arg Pro Phe Gly Ala Pro Pro Pro Ala Asp Ser Ala
        115                 120                 125

Pro Gln Gln Asn Gly Cys Arg Pro Leu Thr Asn Ser Arg Ser Asp Arg
    130                 135                 140

Trp Ser Gln Met Pro Ala Ser Ser Gly
145                 150
```

<210> SEQ ID NO 41

<211> LENGTH: 24740
<212> TYPE: DNA
<213> ORGANISM: Homo sapiens
<220> FEATURE:
<221> NAME/KEY: modified_base
<222> LOCATION: (1)..(6)
<223> OTHER INFORMATION: a, c, g, t, unknown or other
<220> FEATURE:
<221> NAME/KEY: modified_base
<222> LOCATION: (8101)
<223> OTHER INFORMATION: a, c, g, t, unknown or other

<400> SEQUENCE: 41
nnnnnntgta ttttatcata ttttaaaaat caaaaaacaa aaggcagttg aggttaggca 60
tggaggttcg tgcctgtaat cccagcactt tgggaagccg aagcacgtgg atcacctgag 120
gtcaggagtt cgagaccagc ctgcccaata tggtaaaacc ctgtctctac taaaaataca 180
aaaaattagc caggcatggt ggtgggcacc tgtaatccca gctacttggg agactgaggc 240
aggagaatca cttaaacccg ggaggcgggc tgggcgcggt ggctcatgcc tgtaatccca 300
gcactttggg aggccgagac aggcggatca tgaggtcagg agatcgagat catcctggct 360
aacatggtga aaccccatct ctactaaaaa tacaaaaaaa attagccagg cctggtggcg 420
ggcacctgta gtcccagcta cttgggaggc tgaggcagga gaatggcgtg aacctgggag 480
gcggcgttgc agtgagccaa gatcgcgcca ctgcactcca gcctgggcga caagagtgag 540
actccatctt aaagaaaaaa aacaaacccg ggaggcggaa attgcagtca gccgagatct 600
cgccattgca ctcaagtatg ggtgacagag caagactcca tgtcaaaaaa aaaggcagtt 660
gacaggagca aggagcctgg tgaggaagct gtggcatttg acccggctgt gttgctatgg 720
gccagggtgg tgctagtaga ggagctgagt gggaaagagc acaggggaca tgctgaaggc 780
ctgggtgtgg ggatgaggca gagattgggg gcaccttgca gggtcatagc aggtggctgt 840
ggtgagatgg aggaagacac ctggggtact gctctaggct gtcagacata cagaagctgg 900
cccagccaag cccaggggct gcaagggaca tccttttgtg tccccagtga tctgcagctc 960
tcagacaccc tcaagcacag tgcctcttgc ccagcccagc actctcagtg gggagccagg 1020
tgggagaaca ggctcggaag gggacctagg cttatgcagc gagccgggca aagctggaac 1080
tggagcccag gcccctggat gccccctggc ttgtggagtt ctgggatact gaggggaggg 1140
gacagggcat gggagtgcgg tgctctcacc tttgacttga actcattccc caggggacag 1200
gggaggcctc ctcaggatcc acagatgccc agtctcccaa gaggggcctg gtccccatgg 1260
aggaaaactc catctactcc tcctggcagg aaggtaagtt ggaggacgtg caagggcagc 1320
ctcagccccc cacacccagg gctgggtctt tttgggactg acggagctgt cctggccacc 1380
tgccacagtg ggcgagtttc ccgtggtggt gcagaggact gaggccgcca cccgctgcca 1440
gctgaagggg ccggccctgc tggtgctggg cccagacgcc atccagctga gggaggccaa 1500
ggcacccagg ccctctacag ctggccctac cacttcctgc gcaagttcgg ctccgacaag 1560
gtgaggtgca ggggtgggaa agggtgaggg gctgacagcc tggaccctcc tgctaatccc 1620
cacccgtgtg ccctgtgccc agggcgtgtt ctcctttgag gccggccgtc gctgccactc 1680
gggtgagggc ctctttgcct tcagcacccc ctgtgcccct gacctgtgca gggctgtggc 1740
cggggccatc gccgccagcg ggagcggctg ccagagctga ccaggcccca gccctgcccc 1800
ctgccacggg ccacctctct gccctccctg gacacccccg gagagcttcg ggagatgcca 1860
ccaggacctg agccacccac gtccaggaaa atgcacctgg ccgagcccgg accccagagc 1920
ctgccgctac tgctaggccc ggagcccaac gatctggcgt ccgggctcta cgcttcagtg 1980

```
tgcaagcgtg ccagtgggcc cccaggcaat gagcacctct atgagaacct gtgtgtgctg   2040
gaggccagcc ccacgctgca cggtggggaa cctgagccgc acgagggccc cggcagccgc   2100
agccccacaa ccagtcccat ctaccacaac ggccaggact tgagctggcc cggcccggcc   2160
aacgacagta ccctggaggc ccagtaccgg cggctgctgg agctggatca ggtggagggc   2220
acaggccgcc ctgaccctca ggcaggtttc aaggccaagc tggtgaccct gctgagtcgt   2280
gagcggagga agggcccagc cccttgtgac cggccctgaa cgcccagcag agtggtggcc   2340
agaggggaga ggtgctcccc ctgggacagg agggtgggct ggtgggcaaa cattgggccc   2400
atgcagacac acgcctgtgt ccaccctggc ctgcaggaac aaggcaggcc gcctgtggag   2460
gacctcagcc ctgccctgcc ctcctcatga atagtgtgca gactcacaga taataaagct   2520
cagagcagct cccggcaggg gcactcacgg cacacgcccc tgcccacgtt cattgcggcc   2580
aacacaagca ccctgtgccg gttccagggg cacaggtgac ctgggcctta cctgccaccc   2640
gtgggctcaa acccactgca gcagacagac gggatggaaa tcattaggac tccatgttgc   2700
tctgcacggc cgagtgacac gaagaggcag gcggagggag ctgtgaggct tacttgtcag   2760
actcaggaag gagcaacatg agggcccaac tggagacccg gaggcccgag ctgggaggag   2820
gcagtggggg cggggtgcag gtggaaggga tttcagagac accctcgtcc aaaacacttg   2880
ttccctgctg aaactccaac aatttgcaga tacttctggg aaccccaggc gtcagtctcc   2940
tcatctgtaa aggagagaga accgatgacg tatcaggcat aatccttgat gagagtttgc   3000
tgcgtgccta ctcagtgcca ggcgctgggg gacacagccg tgttcaggac agccttggtc   3060
ctgttctccg ggagccgaca ttccaggggg agagaagttt cctgaagact tccatgctgc   3120
gttccctcct ctgctcctgc tcctggcgcc atcctaggag ccagccatgc acgcaagcgt   3180
catgcctcca gggctctgac tgcccagccc ctcaccgcaa ctccacctca gctgcacaca   3240
cccttggcac atcctgaacc tcattttcat gacggacaca caatttttgc tctctcctgt   3300
ccaagcctca tcctctggcc gccacctcct tccagctcac ttcctttagt gcggccagta   3360
ccgcccctgc ctaggcatgt cgacctgcag ggaccctttt ctggctcttc gaggcctctg   3420
cccaccatcc cctctttgtt ctccatagtc ccttccccct gttctctctc gtttcatctt   3480
actggtctgg caaagtcccc ggccttgggc gagccagacc tcctcagtgc ctgcacacag   3540
ctgcccacag ccagagaaat ccatttaagc agactgcctg catccttctt aacagtgcaa   3600
ggcaggcact ccctgccaca agagaccctg ttccctagta gggcagcttt tctcctcccc   3660
agaacctcct gtctatcccc acccaatgtc tcctcacagg catattgggg aaacaggtca   3720
ggctctccca ccgtatctgc aagtgtactg gcatccatct gtcttcttcc taccccctaca   3780
gtagaaacag tgtctgtccc cagctgtgct ctgatcccgg ctcctttcac ctcagagctt   3840
ggaaaattga gctgtcccca ctctctcctg cgcccattca tcctaccagc agcttttcca   3900
gccacacgca aacatgctct gtaatttcac attttaaacc ttcccttgac ctcacattcc   3960
tcttcggcca cctctgtttc tctgttcctc ttcacagcaa aaactgttca aaagagttgt   4020
tgattacttt catttccact ttctcacccc cattctctcc tcaattaact ctccttcatc   4080
cccatgatgc cattatgtgg cttttattag agtcaccaac cttattctcc aaaacaaaag   4140
caacaaggac tttgacttct cagcagcact cagctctggt tcttgaaaca cccccgttac   4200
ttgctattcc tcctacctca taacaatctc cttcccagcc tctactgctg ccttctctga   4260
gttcttccca gggtcctagg ctcagatgta gtgtagctca accctgctac acaaagaatc   4320
```

-continued

```
tcctgaaagc ctgtaaaaat gtccatgcat gttctgtgag tgatctacca agaaaataaa   4380
aaattttaaa aatcaaatgc ccatgcctgg gcccacacgc aggggctctg atttcatcag   4440
tctggtaggt gggttctggg catccacgct cactggattt ccggatgatt gtagtatgca   4500
gcctaggctg ggaaccactg gcctcagcaa gccagtcatt ctccaggtgt cacagaccct   4560
ctaggtgcta atgaccccga aggtctgtct tcagtgcaca cctccccctg agctccagat   4620
ttaggaatcc cactgcacac gagacatctg gatgtggaaa agacatctcc agatcccatg   4680
ggtgaaaggg ggttggggga atggagactc gtgttcttcc aggatgtgtg tggacacaga   4740
atgcaaagcc tggagggatg ctagagccat agggaggaag atttcggctc acttattcat   4800
gcaagcactt cctgatgggt aaggtcttag agcaagctga ggccaagagg cgggcagtcg   4860
aggtgctgct gcaggcaccc ccactcccta cagtggcaag cccaagccca gcccttggca   4920
gctcaaatcc caggacacgc tgaaggtcac ccagagagtc aggggcatgg ctagaaccag   4980
aacccaggac tctggggacc cagcatggca tcctttcctt cattacaaat ctgagctgct   5040
ttgtttccta gggatttctg tgatattcca aggggactgt gggaaagaaa gtccttggaa   5100
accaccagga cgctagaggc ctggcctgga gcctcaggag tctcggccac cagagggcgc   5160
tgggtccttg tccaggtcca gttgctacgc aggggctgcc tgtgctggga ggctccccag   5220
gggacacaga ccagagcctt gcaccagccc aaggaatggg agcctggggt cctctctgct   5280
ggaggactgc caggaccccc aggctgccgc ctcttccttt gctcatttgc tgtttcactt   5340
tgtcaatcct tcctttcttc gtgtgttcat tcacatccac tgtgtgctgg ccctggggaa   5400
atgttagata agacacatta gctgtgtgtc ttcattgtcc taacaaagaa cacaccctgg   5460
aaagagcacc gcagagagtc cccattcccc catctccctc cacacatgga atctggagat   5520
gccttttcca catccagatg tctctggtgc tgtgggattc ttaaataaac aaacatttca   5580
tacagaatgt gagatgatgg agatgctatg gggaaaagta aagcagaggg agggcctagt   5640
gtgtgatgcg ggtgaggcat ccagggattg ctgtttcagc tgtgatcagg aaaggccctg   5700
ggaggaggcc acatctgagc agagacctaa ataaagttgg aaacctgttg ctgagatatc   5760
tggagaagtg tttcaagggc cgggcaccgg gcatggtggc tcacgcctgt aatcccagca   5820
ctttgggagg ccaaggcagg tggatcgctg gaggtcagga gtttgagagc agcctgacca   5880
acatggagaa accccatctc tactaaacat ataaaaatta tccgggcatg gtggttcatg   5940
cctgtagtcc cagctactcg ggaggttgag gcaggagaat cacttgaacg tgggaggcag   6000
aggttgcagc aagccgagat cacaccactg cactccagcc tggatgacag agcgagactc   6060
cgtctcaaaa aaaaaaaaga aaagaaaaaa gaaaaaaaaa gaaaagtgtt tcaagcaggg   6120
gaactggcaa gtggagaggc cctgaggcag aaatatgctt ggcctgctgg aggaaatgtg   6180
agtgaggagg tcagggtggc tggagtggag ggagcgagtg gtaggagtca gacccagttt   6240
attcatattc tgtaggtctt aaggacttca gttttatttt gagtgcaata tgagcccact   6300
ggaatgctaa aagctgagag tgacatggtg ctgtgattct ggctttaaaa atatcacttt   6360
ggctgcttcg tgaagactct ggaaggggca agggtgaaag cagggatgcc cgttaggaga   6420
ccgttacagg ggcgcaggca caaaatggca gtggctggga caatggtggc agcagcggtt   6480
agatgtgaac atgttgaagg tggaatttgc agaatctggg ggaggacaga agagaaagga   6540
taacttcatc gtttctgctg aaccagttgg ataaatgttg gtggcacttc ttgaagtgag   6600
gaaggagtta ggaaggtggg aaaggcacaa gtttgaattg ggccatgatg gtctgagata   6660
cctagtacag tggttcccca accttttgg cagaagggac cgctttcatg gaagacaatt   6720
```

```
tttccacaga ctgggggtgg ggtggggatg gtttcagggt ggttcgagtg cagtacattt   6780
atcattagac tctttttttt tttttttttt tgagatagag tctcgctctg tcacccacac   6840
tggagtgcag tggagccatc ttggctcact acaacctctg ctgcccaggt tcaagtcatt   6900
ctcctgcctc agcctctcaa gtagctggga ttataggcat atgcgccacc acgcccagct   6960
aatttttgta tttttagtag agacggggtt tcaccatatt ggccaggatg gtctcgaact   7020
cctgacctca agtgatcctc ccccgcctca acctcccaaa gtgctggggt tacaggcgtg   7080
aaccactgca cccggcccat ttatcattag attctcataa ggaatgagca acctagatcc   7140
ctcgcatgca cagttcacaa tagggttcac gctcctatgg gagtctaatg ctgccgctgc   7200
actcagcttc tctggcttgc cgctgctcac cttctgctgt gcagcccagt tcctaacagg   7260
ccacaaacgg ggagttgggg acccctgatc tagtaaacat ctaggcaggg ttttggataa   7320
tggagttaga gttcctgggg agaggtcagg ctggccatga aacatgggat gcctttgcat   7380
ataggtggtg ttgaaagcca caggacagta cggggtctca gggggtgagc ataaagagag   7440
gcgacatcag atggccaagg ccagaggcag aggaggatgg gaaggagggg ccagtggggc   7500
agggggaagc tgtgaagcca gggaaaaagg gtgtttcgcg gaaaaggatc aacctggacc   7560
agtgctgccc ctaggcaggg caggatgaaa cttaaccacc acggattcca tggccccatg   7620
gcctccaggc cacaggggac cttgagaaga gagatctcag ggacgggtg cggacaagag   7680
cccgcctggc atggcttcaa gagataactg aaggaaagca agtggagacg cgataaacag   7740
acaactccct ggaggaattt tactctcgag aggagaatta aagggtagta gctggagagg   7800
gatgtggggt caagagaagg tctttaacga cgagaactct cacggcggtt tgtgcagaac   7860
agggtgggtg tgatgactgt ggatggagag gggagaactg cagcgactct gtcctaggag   7920
gaggtgatgg gccgggacca ccaagcgagt ggagggtgga cgccccttcc ctcaccccga   7980
cacccgcatg tgctcagtgt ccgtgccgcc ggccctagtg cctgggctga acgcggggcc   8040
gggactctga ggacgcctcc caggcgcgca gtccgtctgg ccaaggtgga gcgggacggc   8100
ngcttccgac ggtgcgcggg tcggctcggg gttgcaggga catccggcgt ccgctcctgc   8160
cctgttttcc tgccttcgca gagcgttgcg caactctagc tttaaacgcc cctgtccccc   8220
tcaacttgtc tcccccagcc cctctgattt acagattctg cagtccccga gggttgcgcc   8280
tacgataccg acactcgcgg cagcctgcga ggcgagtatg atcgtcccat ttttcggagt   8340
agcaaactaa ggttcagaga ctactatgtc ccaggtcggt ctggtttgaa ggtccgcttt   8400
cctctccctc cgccagcggg cggtgcgagg gactgggcga ggcagcgctt ccctaaggag   8460
gcgacccgca gccccggccc cctcccgact ccgccccgtt gcagggcccg ggtcggcgag   8520
gcctctcagc tctaagcccg acgggacttg gtgattgggc aggacggaag agctgggtgg   8580
ggctttccac cagcggagaa agtctagtgg gcgtggtcgc gacgagggcg tggcctggtg   8640
ccccgccccc gtccgcgcgc tcaaagtgga gggtggctgt gggggcgggg tcagaacact   8700
ggcggccgat cccaacgagg ctccctggag cccgacgcag agcagcgccc tggccgggcc   8760
aagcaggtat cgacgaccgc gcggggcgtc ttgggctgga ccaggcgggc gcccggggcc   8820
tgctgaggac cacaaagggc actgggggtc gtggtccagg ctgtgcttcc tcccgctggc   8880
cctggcccct gcctccgccc ccgcccccgc cttcctgccg ctaagccggc tgcggcgggg   8940
ccgattggcg cctgccggct tcctgcgccg gggccagtct aatgcatggg gcccgggcgg   9000
gggactaagg ggaaactgag tcacgtcggt gtgggagcag ttctgtgtgg gaggcaccac   9060
```

```
cccccactgg gctcggggaa ggatccccct ccaagctatg cttgagggtc ccagccccca   9120
tctgtctcca caggggccgc accccactcc cgccttcccc ttcttcagca cccaggggtc   9180
ccgccctggc tcccagcagc ctcgactggt cccggaatgg ctaggaggat ccgctgcagc   9240
cgcctccctc ccctcccctc ccctcccctc ccctcccctc ccctcccctc ccctcccctc   9300
cccctcgcgt cccaagcccc cgtgtgctcc ctccgctggc tctccgcaca gtgtcagctt   9360
acacgcctta tatagtccga gcaggctcca gccgcggcct gctgccggga cctgggggcg   9420
ggggagagga gagccggccc ctgactcacc cggaccgccc gaggctccag gctggcttgg   9480
ggggaggccg cgccagttta gtccctcggc ccacccctgg ttgcaaagaa cctcaagcct   9540
ggattcaggc acccctcacc gttccagtcc caaggggagg ggggctgctc ctgtctttcc   9600
aaagtgaggt ccgccagcca gcagcccagg ccagcctgac aaaatacctg cctcctatgg   9660
cttgggcgtg ctcaggggct gcccgtgcct gcctggcccc tgtccaaggc tggtatcctg   9720
agctggcccg gcctgcctgc ctgcccgccc accatgctgg ccactcacct tctcttctct   9780
cctctcagga gccggcatca tggattcctt caaagtagtg ctggaggggc cagcaccttg   9840
gggcttccgg ctgcaagggg gcaaggactt caatgtgccc ctctccattt cccgggtgag   9900
cctaggtttg gggagggggc tcccccagcg gtctttcggt gcttaggtct ccagagggtg   9960
atggggggag tcctaacagg agctggtcag gggccagcag gccaggagat gtctaggtcc  10020
ggagatgtag tggtacctgc ctgccacaag gactcccaat gaggtggata ctgggaggga  10080
gcacccaggc ttctccagcc ctgcactgta cccgatgctg ttctcccaag ctcctgtggc  10140
cacctctgag ggctggaggg aggctcattg tgcaggatgg gagcctaaca tttcaggagg  10200
tatctaaact tgaggtggca atgcttggag ccaggcccca ggcaggacac tgtgactata  10260
ggatttcact tcagcctcac tgccgcccag ggaatagcaa tcctcatccc gtttttccag  10320
atgagagaag aactcatgga gaggtggcgg ggctcgctca tcgagtccat ggtgaagcag  10380
ggattggaat tgaggcacag catggcgtac atttttttgtg ggtagaaggg gtctctcccc  10440
agcctatgta aggacccaca tccactgttc ccattcagga tgtggtggcc tttgacccca  10500
agcagaagtg taggacaggg ctccattcta ggggcttaac ttcagcttcc aagagcctgc  10560
cctggtgtgg gtggagctgg aggctggctc ctccctgtag caggggggatt gccttataag  10620
cccaagaatg cagccccacg ctgggatggc caacagtggc tgcggtctgc agagctgaaa  10680
agggctggcc taggcctggc cccctgaacc ccactggtgg gcctctcagc tggtcaccag  10740
gctgcagctc cagctgtatg gtccagttgt gagacacaac aaattgcctg cccagagtgg  10800
gtgaggccag cctgtcggct ggcatctctg actggcctgg gggtcaggag ggggtgggga  10860
cttcctgccc ctatatccgc ctgccccgag agacccaccc aggcgccggg tgggcaggca  10920
gctgttgtca ggaagcccaa ggcaagccca gcctggaggg gcccagaggg tcgtggcctg  10980
aggaggggct caagctggag tctgtctgta ggagctgggc gtgggggtta gggtgggcag  11040
gccagcagtg ctcttctcag gggtcctttg atggcattct cctggaacct gccccgccag  11100
cagggtagtg aggcagtggt tgccctatga cacacgtccc actacatagc cctcacacag  11160
ccctgaaacc tacctgacgt cctgctccct gggaaagtgc tggcccagtg tgtctgggga  11220
gcctgaacct cagtttcttc cctgatggag atgactttca gatatggcct gttgggggca  11280
ctccgggctc cagctccctg gtcagcatcc ctggcatgtg ggcggggcca ctagctgatc  11340
ccagccctgg agttggacct gggcccacat gggtgggtga ggtgggcttt tctgagttag  11400
gccagccccc tccccctccc ctgaccccag aatggaggga ggtgggaggg gcaagggctg  11460
```

```
gctgtgggcc caggcctggg agatgaggta acgtctggga ctggggggct gggctgctca  11520
ggctgactca cccccacctc atgcagggtc cagccccctg gctttttccc tccttggttc  11580
ctctggcctt accctgcccc tggcttgagc ccctccctgc ctctctccag ccacccgccc  11640
agcgctgtct tctgctctcc tgctgccctc cccacgctct gaacacccct catcctctgt  11700
gcttcctgcc ctcctcactc tgggaaggga agccgtcccc gccccccacc ccctctccag  11760
gagccagcta gctgcacccc aagaccccca cctcgggctc agcccacagc tcccaggagc  11820
cagccctgtg ggcagggagt ggctgggcca ggtttccctt ctactgactc accatgacct  11880
tgagtaagtc acttcccctc tggggtgtca cttccccata cacagtataa ggggttgatt  11940
tagttggatt gaactaaagg tgagggagtg gctcagggtg tctccaggtg ggctgacccc  12000
tcagttgggc ccccatgctc agcagaggtg gcccacagtg gtggagcctt agggtcagag  12060
acacttcctg gctctgcctc ttactagctg ggtgacttga ggcaagttgt ttaacctctc  12120
tgtgtacatt tgcaagtgca aaatgggtaa aatcccagat tactccacaa ggttgttgga  12180
agattcagtg tcaatatgta gcatagttgg tgctcaataa actgaagcaa gtcttcttat  12240
ttagcgagtg aggaaggggc cgccgagctc tcttagcctt ctgacctcct acgcaagcaa  12300
gaggtcatgt tgagcccagc tcgcctttct tttcccagtg ctgtcaagct ctgtgcctgg  12360
ctgccctgcc ctctgacatc tctctgaaac ctcttgcctc ccctctccct gcctcagctc  12420
agtctgtgca ctgacccacc tgaggagcct cctggggcca ctggcagcct ggaccccccc  12480
agatcccccc cacccagtga aattgtcttc cagcactgcc tcacaaaagc ctacttgatg  12540
cagtgccagg cctcttgcca gatggctggg tggtccctta ggcttggacc cagtcaagct  12600
gccctgcctg tgttgctggg gctgggctag aggcctggaa ggggtttatc agggtcaccc  12660
tctcagggcc tgggagatac ccaatcccag acattaaaac tgccagtagc ccctctacct  12720
tcaaagccaa gtcctggtcc cttcccctgg cattcaaagc catcgtaagt gaactctcac  12780
ccgctaggca gcacacgcca ttctccttta ccgaggccca ccgcttcctc aaagtcattc  12840
ctgatggtct cagctcatgc tggtggcagc catttctccc agcctactgt ctctactcat  12900
tgccacagga accagggact cccagctcaa gagcctgaag gattggggtc aggggaaatt  12960
ggcagtcgag ggcttgggag tgacagccat gtatggccta cgaagtccca gctgtcaact  13020
taggtcccat tcaggcagtg ttcacaggga accgggagat aacagggcct gttcctggct  13080
ctcaaagggt cccagcagac ccctatagat ggcccccgac agggtgctgg ggggtgagag  13140
gtccataaga gcccccggtg gtttcgggga ggaagctgcc ccctgcatgg gccagagggc  13200
atatctggta ggtggagtgg cctgggcagg aggccagcag gagcctcaaa aggcaatggt  13260
cctcctgaaa cacttgggct ttagcctgag cgtggctgtt tgtggacatc atagcaattt  13320
ctggactgtg ggggagggtg gtggcggtga atagataagc atcgtgactg gggaagctca  13380
ggtgagcacc acctgaggga gagggtctgg cagtgaataa ataagcagtg tgactgggaa  13440
attgtgaagc tcaggtgagc gccaccacct cctgggttgc tttagtgtcc agcagctgcc  13500
tagaactatg ttgaatgaag agctctctgg gttctggaag tgggacagct ttgggtgggg  13560
cagtgttacc accgtcagcc tggcttgggt ctgcagggtc cagggcctcg gtcactttgc  13620
ttctctctcc acagctcact cctgggggca aagcggcgca ggccggagtg gccgtgggtg  13680
actgggtgct gagcatcgat ggcgagaatg cgggtagcct cacacacatc gaagctcaga  13740
acaagatccg ggcctgcggg gagcgcctca gcctgggcct cagcaggtat gcgggtggac  13800
```

```
atggatgggt gcgcccgcgc tggcagtggg gatccctgcg gcccggcccg ctgtcacgct  13860
ttccttctcc tccagggccc agccggttca gagcaaaccg cagaaggtac gaggctggcc  13920
gggacatccg ggcggtgggc ggtgtgggct tggacggcca ggcctgctcg ccctcctggc  13980
acattctcgg taccccaatc cctggccggg agtggagggc agaaaccgga gctaaggcgg  14040
gtctagggcc ctggagttga gccaggggct gctgcacggt cctggcacca cgcatgtccg  14100
cctgtctgtc cgcctgtctg tccgcctgct gcctcccgcc gccggcgctg cgtgctcgcc  14160
cgcactcggt cagccctcgg tcctgcgtgg actgagatcg ccactcccaa atgggcccct  14220
tgaaacctga gtcgtcctct ccccgtagcc tccaaataga tgtagggggt ggggtggggg  14280
tggggggctg gagctgccgc tgtcctctgc tgcaggcgcc ccacttccac ccaggccccc  14340
accttaccct gcccgcccgc cctgcccggc tgtgtctctg cccaggcctc cgcccccgcc  14400
gcggaccctc cgcggtacac ctttgcaccc agcgtctccc tcaacaagac ggcccggcct  14460
ttgggcgccc ccgcccgctg acagcgcccc gcagcagaat gggtacgtcg gcccctgccc  14520
gcccgcgccc acgccatcag gcccactgtg gccccacgcc cgctgcccgc tgctgctcag  14580
tctgtgctgc gccccagccc ggcggaaccg tgcggcacgc cccctggcgg ccggggtggg  14640
gctgcaggca cagggcccct cccgaggctg tggcgccttg cagggcaccg cctggggagg  14700
ggtctctgaa tgacgccgcg ccccctgctg gcggctgggg gttgggttgt ggtgtcgggc  14760
cagctgagcc ccagacactc agtgccgcct tgtccccggc tgttctgacc cctccccgtc  14820
tttcttcctc tcctgtgtct gtccctttgt ccctttatct gtctgtctgt cttatttcct  14880
tcacaggtgc agacccctga caagtcagtg agccccccct tgcctgtgcc tttcttcttc  14940
cttttggcac tctgggtggc ggcccctccc caccctggct gccctcctct ccacttcgcc  15000
ctcctgtcct ctcacctacc cgcccagcag ggctcctggc ctcaccctta cccactccct  15060
cccatcactg taacccaaac ccacatgcac caaatcctgg gaggggctgc ccccaccgcc  15120
cacccccagt gtggggttct gagccacacc ctccccacag acagccgctc cgaccgctgg  15180
tcccagatgc cagcaagcag cggctgatgg agaacacaga ggactggcgg ccgcggccgg  15240
ggacaggcca gtcgcgttcc ttccgcatcc ttgcccacct cacaggcacc gagttcagta  15300
agtgccagcc cagggcaggg ggtactttcc tcgcccccag cccaggcgtg atccctgacc  15360
ctgtgtcttt tttggtcaat gcctgcctct gctctctcag tgcaagaccc ggatgaggag  15420
cacctgaaga aatcaaggta cagggacggg caccagcccc tctcccacct cctgcctctt  15480
ccattccagc tactgccctg tgtctactcc tgaggctccc agctggggct ctcaattctc  15540
ccttccttcc ttccttcctt ccttccttcc ttccttcctt ccttccttcc ttccttcctt  15600
cccttcctcc ttccttcctt ctttcatttc ttccctccct ccttccttcc ctcctccctc  15660
cctgcctccc ttccatctct ccttccttcc acttcttcct ccctctctct ctgcccctca  15720
gggaaaagta tgtcctggag ctgcagagcc cacgctacac ccgcctccgg gactggcacc  15780
accagcgctc tgcccacgtg ctcaacgtgc agtcgtagcc cggccctctc cagccggctg  15840
ccctctctgc ctccctcttt ctgttcctcc tgcccagggc accccccttag tgcctccagc  15900
ttctgcctac ctcacccccc ctttcgtgcc cctggcctga gcctcctgct ggcctggccc  15960
tggccgccca cctgggttca tctgacactg ccttccctct ttgccctgtg gtactgctgt  16020
ctgccaggtc tgtgctgcct tgggcatgga ataaacattc tcagccctgc ttgctctgcc  16080
tgtcttctat ctttgtggac ctggtttgca tttggggtgt gggggtgttt cgtggttcgg  16140
actgtttggg ccctgccgtc cttgttttca gtgggagggg gtacctggca aaggggccct  16200
```

```
gccctgccat cacagatggc ttcctggcat gaggggagcc ccaggagctg cctcagaagc  16260
gggagccctg cctcgtctcc cagctagaga ccgcacacca gctaactgga cattgctagg  16320
agaagctgcc cttcccatcc ctaccccagt gggacctgga atccaactcg gcagtttcca  16380
cgcccccagt catctcccgt ggggccagca ggacccaggt tggggggtgg ggccatgtca  16440
ggaagctcag ccatgcaggg ccttgaatgg cagatcttgc agccaggtgc ccaggacaga  16500
agccccagcc ccagcctcat ctacacccca ggagccctgg cctggtgaga gggagtgggc  16560
tcgggcctgg gcaagggtgg gcagcctcca ggggcatggg ggtggtgggc ttctctcagc  16620
tgcctggggc tccacccccg tcctttgggg tccctgggca cccctttaga gtcactttcc  16680
ccggcaggcc ctaccgcccc cagccctacc agccgcccgc cctgggctgt ggaccctgcg  16740
tttgccgagc gctatgcccc ggacaaaacg agcacagtgc tgacccggca cagccagccg  16800
gccacgccca cgccgctgca gagccgcacc tccattgtgc aggcagctgc cggaggggtg  16860
ccaggagggg gcagcaacaa cggcaagact cccgtgtgtc accagtgcca caaggtcatc  16920
cggtgggtgg cctgttcctg tccgaccctg gctttcccat cctgcagccc agccccacct  16980
gtctgcccac ctgtcttgcc tcagctgcga ctggggggaa taaggattca gttctcagct  17040
ggagtaggag tagggacctg ggctgggtcc tcccattctt aatcccacgc tacctacccc  17100
agcccaccca caacaactgc tagcagcatc tgccgtggcg aaatagccga agggccaacc  17160
ataggctgaa gctgcacccc tacctttgct gctctctggg caaagagggg cctgccccct  17220
cccagcgcgt ctgcccctcc ctcctgctct ctgtctccct ctgctctcag agcatacagg  17280
cctggagcca ctccctctgt gcactgcccc gtggggccaa gcagcatcaa acaccccccca  17340
gcatcagcgt gccggattct agagccttcc taattcgcag gcctggcctg ctctcatctc  17400
tgtcagctct tttttttttt tttttgaaac agagtctcac tgtgttgccc acgttggcgt  17460
gcagtggcgc gatctcggct cactgcaacc tctgcctcct gggttcaaga gattctcctg  17520
cctcagcctc ctgagtagct gggattacag gcacccgcca ccatgcctgg ctaattttgt  17580
atttttagta gagacggggt tttaccatgt tggccaggct ggtctcaaac tcctcacctc  17640
aggtgatctc aggcctgcct tggcctccca aagtgctggg actacaggtg tgagccactg  17700
tgcccagccg actctatcag ctcttgccag gtagaacagg caggccagca ggacagggca  17760
gctccagggt ttgcccaggg gcggctcagc ttttatgagg ctccagtcgt cagcccttcc  17820
tcccggggtc ctccctgctc taaagctgcc tctcctgtca ccagcagttc agtgtggcgg  17880
actggctctg taagcttcat ggctgccacg gtcacttccc aagcctgtct tctatcctat  17940
gtggaaaatg ggagagaatga actgtccctc ccaaggcctc ctggtgggtg gtcagtcaac  18000
ctgaaggggg ccaagacccc cacctctctg cgtgtgctcc ctctgaccgc tctcgcctcc  18060
ctgcaggggc cgctacctgg tggcgctggg ccacgcgtac cacccggagg agtttgtgtg  18120
tagccagtgt gggaaggtcc tggaagaggg tggcttcttt gaggagaagg gcgccatctt  18180
ctgcccacca tgctatgacg tgcgctatgc acccagctgt gccaagtgca agaagaagat  18240
tacaggcgtg agtagggctg gctggcgggg aggtggtccc aagcctgtca gtgggaacga  18300
gggctgctgg gaaacccaca gtccaggtct ctccccgagt gagcctccgg gtccttacca  18360
gcgtaataaa tgggctgctg tactggcctc accctgcatt agtcaggatg ctcttaacaa  18420
atgaccatgt tcctgctcag aaaccgccca aggctgcaaa gagcaggagg accaagccag  18480
gagaagccct gggccctcct gactcccact ttgggctctc cctgccctgg tgaaatgaca  18540
```

gaacggccaa cttgacacgc tgaagctgct ctgtctcatg cgtcctcctc atttctggat 18600
ccagagccag ggctgccagg agtagccaga gagctctgtg tggtgatgtt catattagtg 18660
aggtttacct tgaccacgag cagtgggaaa ctcaaaataa tggtggctta tttctcatct 18720
aaaaacatcc cggggtgggt ggtctgggac tgatctggtg gacccaggct ccgccttgtt 18780
gcttgactgt tggcagcacc tgcttactta ccactcatgg tgcaagatga cacttcagcc 18840
tccgccaaaa tgctcacctt ccagccagca ggaagtcgga aggagaagaa aggggacaga 18900
gccccatggc gtccatcctt agaggatgct gccacctgaa cctctgcttt catcctgttg 18960
gtcagaaccc agtcacatga ccacacccag tggcaacgga ggctgggaaa tatagtcttt 19020
attttgggca cccatgtgtc cagcaaaact gggggttcca tcagtcggca agaacgggag 19080
agtggccgat gcagtggctg atgcttgtat cccagcactt tgggaggtcg aggtgggcag 19140
atcacctgag gtcaggagtt caagaccagc ctggccaata tggtgaaacc ctgtctctac 19200
taaaaataaa aaaattagct gggtgtgctg gcgcacctgt agtcccagct acttgggagg 19260
ctgaggcagg agaatcgctt gatcttgaga ggtggaggtt gcagtgagcc aagattgtgc 19320
cactgccttc cagcctggga gacagcaaaa aaaaaaaaaa aaaaaaaaaa aaaaagggcc 19380
aggcacggtg gctcacacct gtaatcccag cactttggga ggccgagatg ggcggatcac 19440
gaggtcagga gattgagacc atcctggcta acacggtgaa accccatctc tactaaaaat 19500
acaaaaaaat tggccgggca tggtggagta gtcccagcta ctcgggaggc tgaggcagga 19560
gaatggcgtg aacctgggag gcagagcttg cagtgagccg agatcgcgcc actgcactcc 19620
agcctgggca acagagcgag actcttgtct caaaaagaaa aaaagaaaga gaaatctgcc 19680
tcccagcctt gggctcctgc cctaccagcc cacacccctg gtagagcctc ctctcccacc 19740
agctcaaagc ccaagttcct tcactgtgac cttgtctgct cctctaaaac aggcaacacc 19800
agacagtgag aagagccagc cagacatggg cagaaaacct atttctgtga tctactggct 19860
gtgtgagcag gggctagttg ctctctctgg gcctcactga agagaagggt ggcactatgc 19920
tagggccggc acggttgcaa ggtagatgta agatggggta caggtgttgt ggagggcaga 19980
aatgcaccat ccgaaggcta catgtccccc acacttatgt cttgcttggc ccacactgtt 20040
tcattttaaa atcagtagca aacaatttaa aaaatcagaa gatttgcctg catgatgcag 20100
tggctcatgc ctgtaatccc agcactttgg gaggccaagg tgggaggatt gcttgagccc 20160
aggagttcaa gaccagcatg ggcaccatag caagacccct gtttctacaa aaaaaaaaaa 20220
attagaaaat tagccaagtg tggtggcatg cacctgtggt cccagctact tgggaggcag 20280
agggaaagtg agatctcctg ctttttattt ctttatgtat aatgataggg tcttgctctg 20340
ttgcccaggc tggagtgcag tggcatgatc actgctcact gcagccttga tctcctgggc 20400
tcagaggatc ctcccacctc agcctcccaa atagctagga ctagaggtgc ccaccagcat 20460
gctcagcaga tttttaaatc tttttgtaga gatgaggttt tgctatgttg cccaggctgg 20520
tctcgaactc ctggcctcga gcgatcctcc caccttggcc tcccaaagca ctgggattac 20580
agacgtgagc cactgcgccc agcagatttc tctttaacac ctagatttca gcctgagcca 20640
ggcaggcatt cctgaatgaa ccagtagtac tgctcccaga agaagaggtc ctcctccgtg 20700
tgacacagtc cccacttggc ccttgcaggg attggatctg ggatccctgg atttaaactc 20760
agggccatcc tcataacagc ctcacaaggc tgggattagc ttcccagttc acaagggaag 20820
aaaccaagac ttgagaaggt caaggtctgg ccagacccac acatcttgga ccctcatacc 20880
gcctcgaggc cccatgctgc cctctgcctg ctccagatgt gaatactgct ggccctggct 20940

```
ggccccggct ggccccgagg gtcctaggga tgaacagccc agcccaggga gagctcagcc  21000
ccttgtgcct ctgccccttc ccacctcctg cggaggccag tcgactcacc cacaaagggc  21060
caggcactgt ggggatagat cagctaacaa aacagttgat gcttcctgcc cttctgggcc  21120
ttacattttg gctggaagaa gaggggagag gcagactgta agcaataagc gcaataagta  21180
ggttgcctgg aagtaatgtt agatcacgtt acggaaaaca ggaaagagca gagcgacaag  21240
tgctggggtg cgtggtgcag ggaaggcagc tggctgctgc tggtgtggtc agagtgggcc  21300
ctcatggaga agactgcatt cgagcagaaa cttgaagggg gtgaggggtg agcctagaga  21360
tatctggggc agagcagtcc aggcagaggg gacagccggt gtcaagccca ggacaggagt  21420
gtgcctggtg tgccagtttc aggcaagagg ccagtgtgca gaggcaaggt gagaacgcaa  21480
gggagagcag tggcggagac gggtgggaac gaggtcagac ctgctggcct ccagcctctg  21540
catggggctt ggctcttgct gggagcaatg ggaagcagta cacagtttca tgcaggggga  21600
gaaggcctgt cttgggttgc aggggcacgc tgtggcagct gggatcagag agaggagctt  21660
gtaggccagt tgttatgtgg tcccacgggc cagatggcca tggcttacct cacttcaggg  21720
aggctgtgag aagcactcag aatctggatg tgccttgggg gtgggcccca ctggatttcc  21780
tggtggacct ggtgtggggt gtgagaggag ggtgtgtttg gctgcagcag acaggagaat  21840
ggagttgcca tccgcgtgat ggggatggct gtgggaggag aggtttgggg tgagggaatc  21900
aggaactgag tgctggacat ggcaagtctg aaggcgcagt ggtcgtccac tcagagacct  21960
tggagttgga gatggaggtg tgggagtcct gaacagttag atgtagtgtt taccgcgaga  22020
aggaacaggg cttgcggcca gccctcctgt gttcccgtga cccagggcag ggcaggaggg  22080
gcctgagcct gccgagtgac tgggacctcc ttccaggaga tcatgcacgc cctgaagatg  22140
acctggcacg tgcactgctt tacctgtgct gcctgcaaga cgcccatccg gaacagggcc  22200
ttctacatgg aggagggcgt gccctattgc gagcgaggta cccactggcc agtgagggtg  22260
aggagggatg gtgcatgggg caggcatgaa tccaggtcct ctttctctct gcccccattc  22320
tcagactatg agaagatgtt tggcacgaaa tgccatggct gtgacttcaa gatcgacgct  22380
ggggaccgct tcctggaggc cctgggcttc agctggcatg acacctgctt cgtctgtgcg  22440
gtgagagccc cgcccctcga actgagcccc aagcccaccg gccctctgtt cattccccag  22500
gagatgcagg agaagttggg aaggggcctc tcctgctgcc cccaacccca tgtgactggg  22560
cctttgctgt ccttagatat gtcagatcaa cctggaagga aagaccttct actccaagaa  22620
ggacaggcct ctctgcaaga gccatgcctt ctctcatgtg tgagcccctt ctgcccacag  22680
ctgccgcggt ggcccctagc ctgaggggcc tggagtcgtg gccctgcatt tctgggtagg  22740
gctggcaatg gttgccttaa ccctggctcc tggcccgagc ctggggctcc ctgggccctg  22800
ccccacccac cttatcctcc caccccactc cctccaccac cacagcacac cgatgctggc  22860
cacaccagcc ccctttcacc tccagtgcca caataaacct gtacccagct gtgtcttgtg  22920
tgcccttccc ctgtgcatcc ggaggggcag aatttgaggc acgtggcagg gtggagagta  22980
agatggtttt cttgggctgg ccatctgggt ggtcctcgtg atgcagacat ggcgggctca  23040
tggttagtgg aggaggtaca ggcgagaccc catgtgccag gcccggtgcc cacagacatg  23100
aggggagcca ctggtctggc ctggcttgga ggttagagaa gggtagttag gaagggtagt  23160
tagcatggtg gctcatgcct gtgatcccag cactttggaa ggccaaggtg ggcagatcgc  23220
ttgaggtcag gagttcgaga cctcatggcc aacacggtga aacagcgtct ctagtaaaaa  23280
```

```
tacaaaaatt agccgagtgt ggtggggcat gcctgtaatc ccagccactc aggaggctga  23340

ggcgggaaaa tcacttgaac ctgggaagtg gaggttgcag tgagctgaga tcacaccact  23400

gcgcgcgagc ctgggtggca gatggcagag cgagaccctg cttcaaaaaa aaaaaaaaaa  23460

aaaaaaaaaa gaagggtagt tgtagttggg ggtggatctg cagagatatg gtgtggaaaa  23520

cagcaatggc cacagcaaag tcctggaggg gccagctgcc gtccaaacag aagaaggcag  23580

ggctggagag ggtagccctt aggtcctggg aagccacgag tgccaggcag tagagctggg  23640

gctgtctctt gaggttaggg cagggcaagg cacagcagag tttgaaatag gtttgtgttg  23700

tattgcagaa aagaggcccc agaacactga gggagtgcag gagggaggct gggaggagga  23760

gttgcagcag ggcctagggg cgggggccag gcaagggagg ggcagagagt aatatggcag  23820

agatgggacc cagtggcagg tccgggggat gagggatgga gagaaggaca ggagcgttgc  23880

caggcatctg gcctatacca gacatgctca cgctgtctcc cgcgaacctc ctagcaacct  23940

tgcgccgttg tctgcaatca cttatttcat tttttctttt ttaactttaa tttttttgt  24000

ttttaagaga caggatctcc ctaggttgcc cgggctggtt tcaaactcct gggctcaagc  24060

aattcttcct ccttagcccc aaagtgctgg cattacaggt gtgagccacc atgcctggcc  24120

cacttatttt ctagatgagg cacagaaaga ttgggagact tgaccaaggt cacgctgtca  24180

ttgagccatg agccagacta gaatccaggc ctgaagctgg gtgcgctgtc ccaggactgg  24240

ctggcactga gtaccatttg ccagcgagca tctctctggg aagctgactt ctgcccggta  24300

cctggaggac tgtagacctt ggtggtggcg ccgtcactct ggggcttcct gcctcccact  24360

gatgcccgca ccaccctaga gggactgtca tctctcctgt cccaagcctg gactggaaag  24420

actgaagaga agccttaagt aggccaggac agctcagtgt gccatggctg cccgtccttc  24480

agtggtccct ggcatgagga cctgcaacac atctgttagt cttctcaaca ggcccttggc  24540

ccggtcccct ttaagagacg agaagggctg ggcacggtga ctcacacctc taatcccagc  24600

actttggaag gctgaggctg gagaagggct ccagcttagg agttcaggac cagcctgggc  24660

aacatggtga gaccctgttt tgttttgttt tttgtttttt tgagatggag tcttgctctg  24720

tcgcccaggc tggagtgcag                                              24740
```

<210> SEQ ID NO 42
<211> LENGTH: 25
<212> TYPE: DNA
<213> ORGANISM: Rattus norvegicus

<400> SEQUENCE: 42

```
gcactacctt gaaggaatcc atggt                                           25
```

<210> SEQ ID NO 43
<211> LENGTH: 26
<212> TYPE: PRT
<213> ORGANISM: Artificial Sequence
<220> FEATURE:
<223> OTHER INFORMATION: Description of Artificial Sequence: Synthetic peptide

<400> SEQUENCE: 43

```
Ala Asp Pro Pro Arg Tyr Thr Phe Ala Pro Ser Val Ser Leu Asn Lys
  1               5                  10                  15

Thr Ala Arg Pro Phe Gly Ala Pro Pro Pro
             20                  25
```

<210> SEQ ID NO 44

<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 44

Gln Asp Pro Asp Glu Glu
1 5

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 45
aggatggctt ccaccagtgc 20

<210> SEQ ID NO 46
<211> LENGTH: 22
<212> TYPE: DNA
<213> ORGANISM: Artificial Sequence
<220> FEATURE:
<223> OTHER INFORMATION: Description of Artificial Sequence: Synthetic
primer

<400> SEQUENCE: 46
tgcgtaaaag acctcaccct cc 22

<210> SEQ ID NO 47
<211> LENGTH: 19
<212> TYPE: DNA
<213> ORGANISM: Artificial Sequence
<220> FEATURE:
<223> OTHER INFORMATION: Description of Artificial Sequence: Synthetic
primer

<400> SEQUENCE: 47
cacaagtcag tgggagagc 19

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 48
gcttccgctg tttgtgtttg 20

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 49
accacagtcc atgccatcac 20

<210> SEQ ID NO 50

<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 50
tccaccaccc tgttgctgta 20

<210> SEQ ID NO 51
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 51
aatacgactc actatagggc tcga 24

<210> SEQ ID NO 52
<211> LENGTH: 17
<212> TYPE: DNA
<213> ORGANISM: Artificial Sequence
<220> FEATURE:
<223> OTHER INFORMATION: Description of Artificial Sequence: Synthetic primer

<400> SEQUENCE: 52
ggaagcccca aggtgct 17

<210> SEQ ID NO 53
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 53
agccggcatc atggattcct tcaa 24

<210> SEQ ID NO 54
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 54

Tyr Ala Pro Ser Cys Ala Lys
1 5

<210> SEQ ID NO 55
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 55

Asp Leu Tyr Asp Asp Asp Asp Lys
1 5

<210> SEQ ID NO 56
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 56

Tyr Ala Pro Ser Cys Ala Lys Cys Lys
1 5

<210> SEQ ID NO 57
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 57

Ile Thr Gly Glu Ile Met His Ala Leu Lys
1 5 10

<210> SEQ ID NO 58
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 58

Asp Phe Asn Val Pro Leu Ser Ile Ser Arg
1 5 10

<210> SEQ ID NO 59
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 59

Tyr Thr Phe Ala Pro Ser Val Ser Leu Asn Lys
1 5 10

<210> SEQ ID NO 60
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 60

Val Leu Glu Glu Gly Gly Phe Phe Glu Glu Lys
1 5 10

<210> SEQ ID NO 61
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 61

Val Val Leu Glu Gly Pro Ala Pro Trp Gly Phe Arg
1 5 10

<210> SEQ ID NO 62
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 62

His Ser Gln Pro Ala Thr Pro Thr Pro Leu Gln Ser Arg
1 5 10

<210> SEQ ID NO 63
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 63

Thr Phe Tyr Ser Lys Lys Asp Arg Pro Leu Cys Lys
1 5 10

<210> SEQ ID NO 64
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 64

Asp Arg Pro Leu Cys Lys Ser His Ala Phe Ser His Val
1 5 10

<210> SEQ ID NO 65
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 65

Ile Arg Ala Cys Gly Glu Arg Leu Ser Leu Gly Leu Ser Arg
1 5 10

<210> SEQ ID NO 66
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 66

Leu Gln Gly Gly Lys Asp Phe Asn Val Pro Leu Ser Ile Ser Arg
1 5 10 15

<210> SEQ ID NO 67
<211> LENGTH: 13
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 67

Ala Phe Tyr Met Glu Glu Gly Val Pro Tyr Cys Glu Arg
  1               5                  10


<210> SEQ ID NO 68
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Thr Ser Ile Val Gln Ala Ala Ala Gly Gly Val Pro Gly Gly Gly Ser
  1               5                  10                  15

Asn Asn Gly Lys
             20


<210> SEQ ID NO 69
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Ile Leu Ala His Leu Thr Gly Thr Glu Phe Met Gln Asp Pro Asp Glu
  1               5                  10                  15

Glu His Leu Lys
             20


<210> SEQ ID NO 70
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Thr Pro Ile Arg Asn Arg Ala Phe Tyr Met Glu Glu Gly Val Pro Tyr
  1               5                  10                  15

Cys Glu Arg


<210> SEQ ID NO 71
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Gln Arg Leu Met Glu Asn Thr Glu Asp Asp Trp Arg Pro Arg Pro Gly
  1               5                  10                  15

Thr Gly Gln Ser Arg
             20


<210> SEQ ID NO 72
<211> LENGTH: 21
```

-continued

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Ile Leu Ala His Leu Thr Gly Thr Glu Phe Met Gln Asp Pro Asp Glu
  1             5                  10                  15

Glu His Leu Lys Lys
            20


<210> SEQ ID NO 73
<211> LENGTH: 31
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Ala Ala Gln Ala Gly Val Ala Val Gly Asp Trp Val Leu Ser Ile Asp
  1             5                  10                  15

Gly Glu Asn Ala Gly Ser Leu Thr His Ile Glu Ala Gln Asn Lys
            20                  25                  30


<210> SEQ ID NO 74
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Thr Glu Ala Pro Ala Pro Ala Ser Ser Thr Pro Gln Glu Pro Trp Pro
  1             5                  10                  15

Gly Pro Thr Ala Pro Ser Pro Thr Ser Arg Pro Pro Trp Ala Val Asp
            20                  25                  30

Pro Ala
```